US008790651B2

(12) United States Patent
Bammert et al.

(10) Patent No.: US 8,790,651 B2
(45) Date of Patent: Jul. 29, 2014

(54) INTERLEUKIN-31 MONOCLONAL ANTIBODY

(75) Inventors: Gary F. Bammert, Portage, MI (US); Steven A. Dunham, Kalamazoo, MI (US)

(73) Assignee: Zoetis LLC, Florham Park, NJ (US)

(*) Notice: Subject to any disclaimer, the term of this patent is extended or adjusted under 35 U.S.C. 154(b) by 0 days.

(21) Appl. No.: 13/536,081

(22) Filed: Jun. 28, 2012

(65) Prior Publication Data

US 2013/0022616 A1 Jan. 24, 2013

Related U.S. Application Data

(60) Provisional application No. 61/510,268, filed on Jul. 21, 2011.

(51) Int. Cl.
*A61K 39/395* (2006.01)
*G01N 33/53* (2006.01)
*C07K 16/00* (2006.01)
*C07K 16/18* (2006.01)
*C07K 16/24* (2006.01)

(52) U.S. Cl.
USPC ... 424/145.1; 424/158.1; 435/7.1; 530/387.1; 530/388.1; 530/388.23; 530/391.1; 530/391.3

(58) Field of Classification Search
None
See application file for complete search history.

(56) References Cited

U.S. PATENT DOCUMENTS

| 7,531,637 | B2 | 5/2009 | Siadak et al. |
| 2002/0052030 | A1* | 5/2002 | Wonderling et al. ......... 435/183 |
| 2006/0228329 | A1 | 10/2006 | Brady et al. |
| 2009/0208494 | A1 | 8/2009 | Bondensgaard et al. |
| 2010/0221244 | A1 | 9/2010 | Yao et al. |

FOREIGN PATENT DOCUMENTS

| WO | WO 2006/088855 A1 | 8/2006 |
| WO | WO 2006/088955 A2 | 8/2006 |
| WO | WO 2007/133816 A2 | 11/2007 |
| WO | WO 2008/028192 A2 | 3/2008 |
| WO | WO 2010/117448 A2 * | 10/2010 |
| WO | WO 2011/047262 A2 | 4/2011 |

OTHER PUBLICATIONS

Paul, Fundamental Immunology, 3rd edition, 1993, Raven Press, New York, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
Mizuno et al. (2009, Veterinary Immunology and Immunopathology 131: 140-143).*

Olivry, et al. "The ACVD Task Force on Canine Atopic Dermatitis: Forewords and Lexicon" Veterinary Immunology and Immunopathology 2001; 81: 143-146.
Olivry, et al. "Animal Models of Atopic Dermatitis" 2001 *supra*; Marsella & Olivry Clinics in Dermatology 2003; 21: 122-133.
Scott, et al. "Treatment of Canine Atopic Dermatitis with a Commercial Homeopathic Remedy: A Single-Blinded, Placebo-Controlled Study" Canadian Veterinary Journal 2002; 43: 601-603.
Hillier et al. "The ACVD Task Force on Canine Atopic Dermatitis (I): Incidence and Prevalence" Veterinary Immunology and Immunopathology 2001; 81: 147-151.
Picco, et al. "A Prospective Study on Canine Atopic Dermatitis and Food-Induced Allergic Dermatitis in Switzerland" Veterinary Dermatology 2008; 19: 150-155.
Sousa & Marsella "The ACVD Task Force on Canine Atopic Dermatitis (II): Genetic Factors" Veterinary Immunology and Immunopathology 2001; 81: 153-157.
Schwartzman, et al. "Canine Reaginic Antibody" "Characterization of the Spontaneous Anti-Ragweed and Induced Anti-Dinitrophenyl Reaginic Antibodies of the Atopic Dog" Clin. Exp. Immunol. 1971; 9: 549-569.
Dillon et al. "Interleukin31, a Cytokine Produced by Activated T Cells, Induces Dermatitis in Mice" Nature Immunology 2004; 5:752-760.
Bilsborough et al. "IL-31 is Associated with Cutaneous Lymphocyte Antigen-Positive Skin Homing T Cells in Patients with Atopic Dermatitis" J Allergy Clin Immunol. 2006 117(2):418-425.
Takaoka et al. "Expression of IL-31 Gene Transcripts in NC/Nga Mice with Atopic Dermatitis" European Journal of Pharmacology 2005; 516: 180-181.
Takaoka et al. "Involvement of IL-31 on Scratching Behavior in NC/Nga Mice with Atopic-Like Dermatitis" Experimental Dermatology 2006; 15, 161-167.
Raap et al. "Correlation of IL-31 Serum Levels with Severity of Atopic Dermatitis" Journal Allergy Clinical Immunology 2008;122(2):421-423.
Sonkoly et al. "IL-31: A New Link Between T Cells and Pruritus in Atopic Skin Inflammation" Journal Allergy Clinical Immunology 2006; 117:411-417.
Neis et al. "Enhanced Expression Levels of IL-31 Correlate with IL-4 and IL-13 in Atopic and Allergic Contact Dermatitis" Journal Allergy Clinical Immunology 2006; 118, 930-937.
Raap et al. "Increased Levels of Serum IL-31 in Chronic Spontaneous Urticaria" Experimental Dermatology 2010;19(5):464-466.
Yagi, et al. "Interleukin-31 Stimulates Production of Inflammatory Mediators from Human Colonic Subepithelial Myofibroblasts" International Journal of Molecular Medicine 2007; 19(6): 941-946.
Nuttall, et al. "T-helper 1, T-helper 2 and Immunosuppressive Cytokines in Canine Atopic Dermatitis" Veterinary Immunology Immunopathology 2002; 87, 379-384.
Maeda, et al. "Production of a Monoclonal Antibody to Canine Thymus and Activation-regulated Chemokine (TARC) and Detection of TARC in Lesional Skin from Dogs with Atopic Dermatitis" Veterinary Immunology Immunopathology 2005; 103, 83-92.

(Continued)

*Primary Examiner* — Elizabeth C Kemmerer
(74) *Attorney, Agent, or Firm* — Gloria K. Szakiel; Barbara L. Renda

(57) ABSTRACT

An isolated antibody that specifically binds to at least one of canine Interleukin-31 (IL-31) or feline IL-31 is provided. Such antibodies can be in the form of diagnostic and/or veterinary compositions useful for treating a pruritic and/or allergic condition in dogs or cats.

28 Claims, 19 Drawing Sheets

(56) References Cited

OTHER PUBLICATIONS

Maeda, et al. "Expression of CC Chemokine Receptor 4 (CCR4) mRNA in Canine Atopic Skin Lesion" Veterinary Immunology Immunopathology 2002b; 90, 145-154.

Maeda, et al. "Expression Analysis of CCL27 and CCL28 mRNA in Lesional and Non-Lesional Skin of Dogs with Atopic Dermatitis" Journal Veterinary Medical Science 2008; 70, 51-55.

Chattopadhyay, et al. "Interleukin-31 and Oncostatin-M Mediate Distince Signaling Reactions and Response Patterns in Lung Epithelial Cells" Journal of Biological Chemistry 2007; 282:3014-3026.

Wai K. Ip et al. "Interleukin-31 Induces Cytokine and Chemokine Production from Human Bronchial Epithelial Cells Through Activation of Mitogen-activated Protein Kinase Signalling Pathways: Implications for the Allergic Response" Immunology, 2007; 122, 532-541.

PCT International Search Report PCT/IP2012/053450 Priority Date Jul. 21, 2011.

Mizuno et al. "Molecular Cloning of Canine Interleukin-31 and its Expression in Various Tissues" Veterinary Immunology and Immunopathology 2009; 131, 140-143.

Grimstad et al. "Anti-interleukin-31Antibodies Ameliorate Scratching Behaviour in NC/Nga Mice: a Model of Atopic Dermatitis" Experimental Dermatology 2009;18: 35-43.

Le Saux S. et al. "Molecular Dissection of Human Interleukin-31-mediated Signal Transduction Through Site-directed Mutagenesis" The Journal of Biological Chemistry Jan. 29, 2010;285(5):3470-3477.

Grimstad et al. "The Effect of Anti-interleukin-31-Antibodies on Scratching Behaviour and Development of Dermatitis on NC/Nga Mice" Inflammation Research Supplement Jun. 3, 2007 S 396-397.

PCT International Preliminary Report on Patentability PCT/IB2012/053450 Mailed Jan. 30, 2014.

* cited by examiner

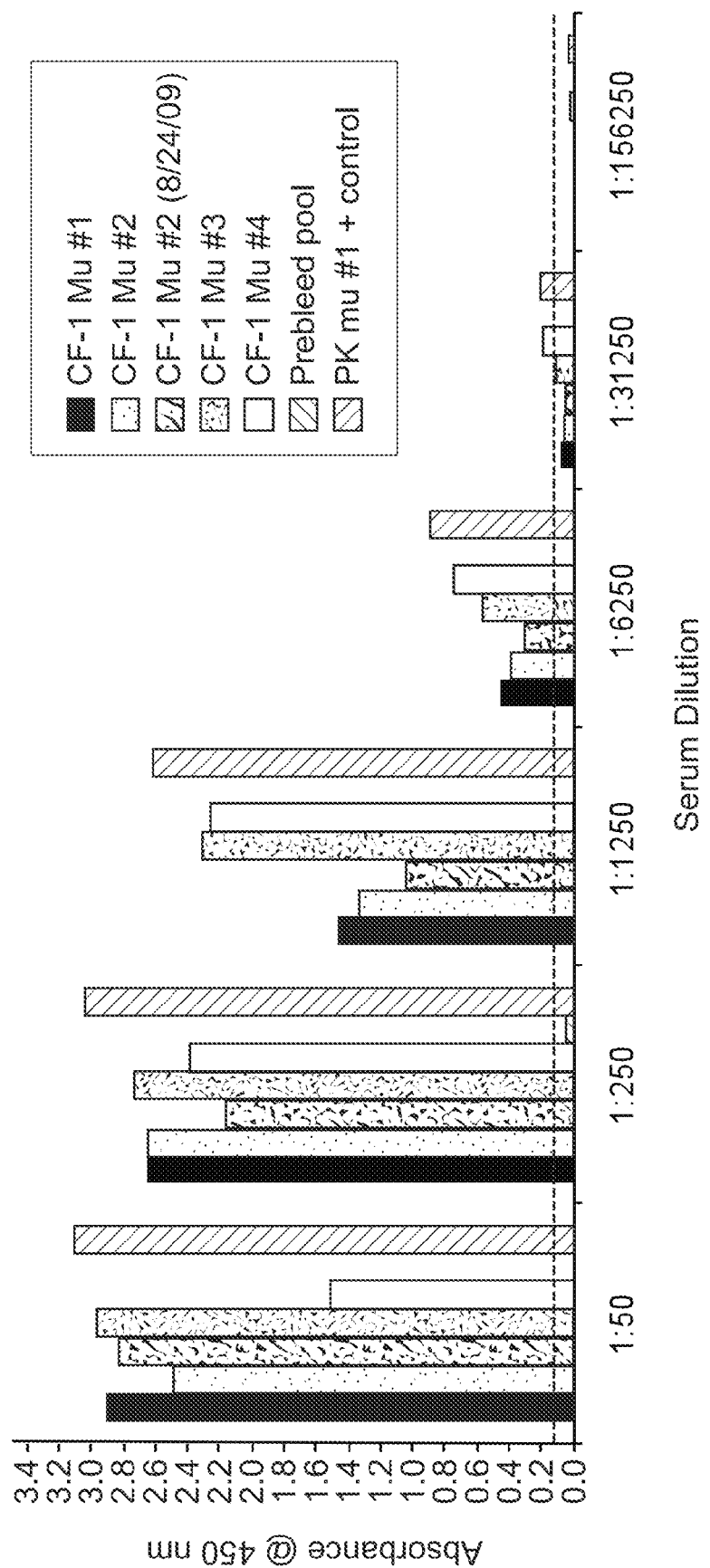

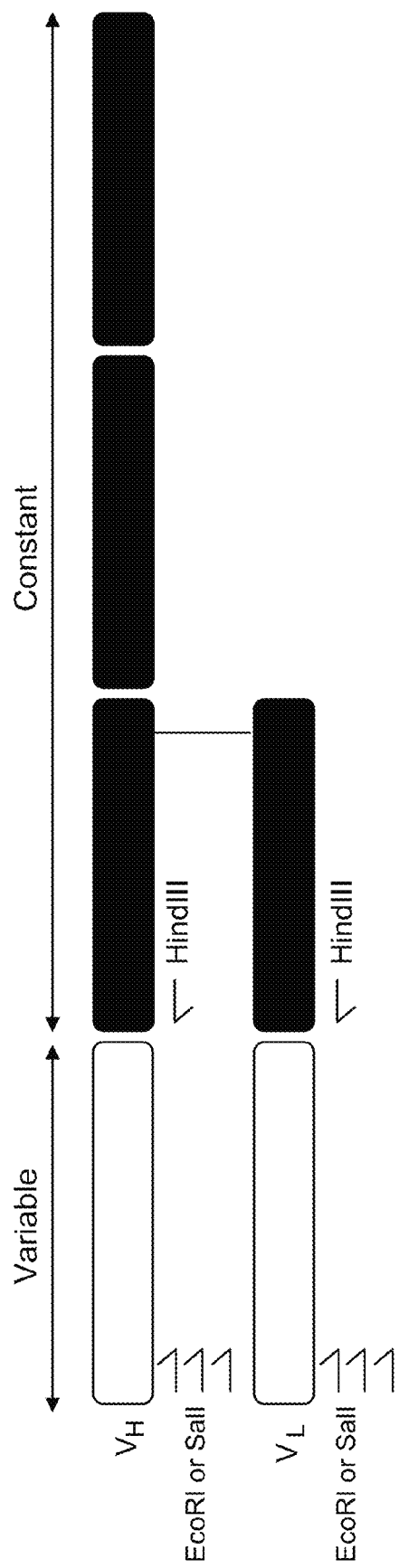

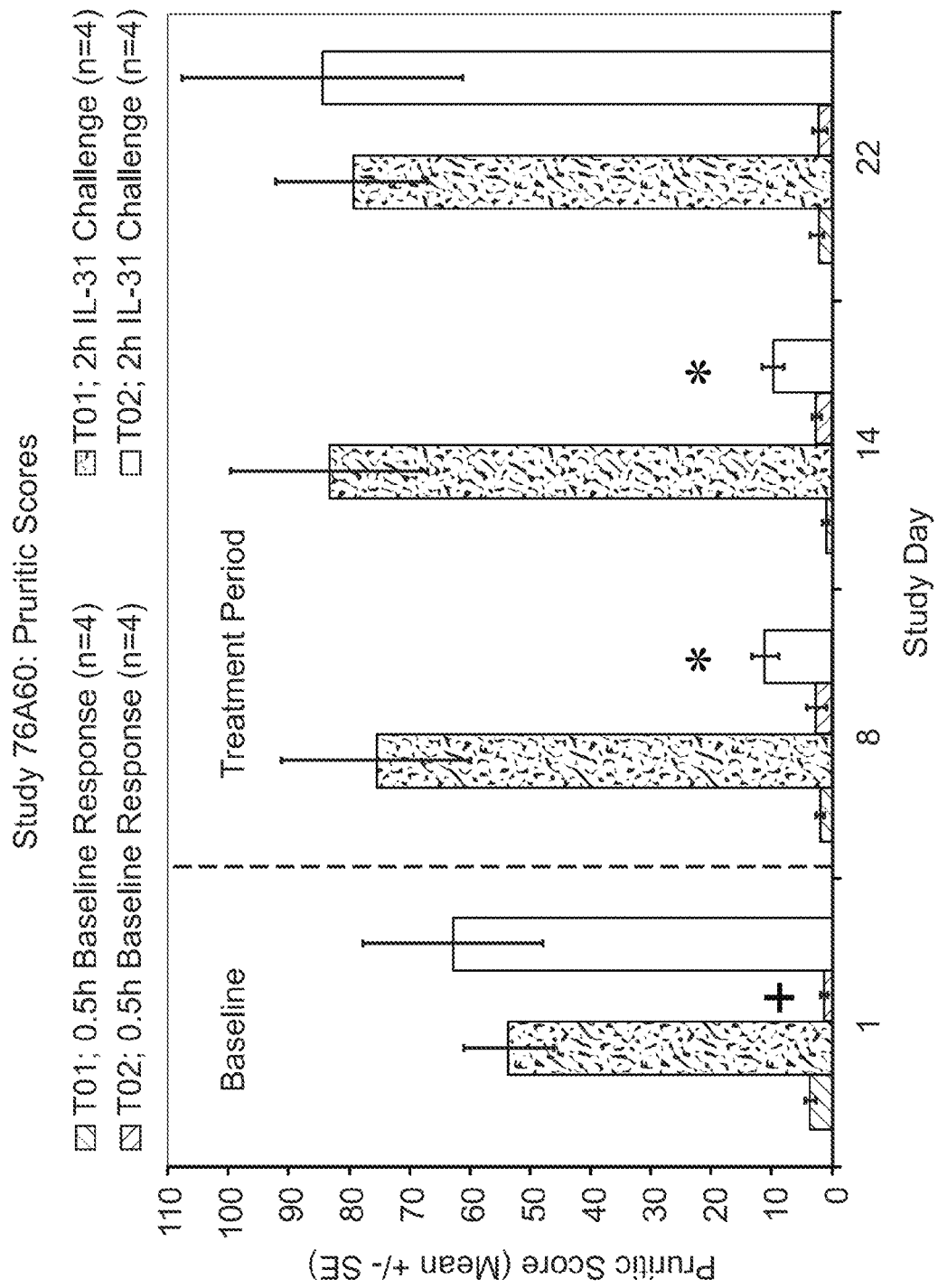

FIG. 9

T01-Placebo @ 1X/d, SC on d0 and d7 (n=4)

| Date | 26-Oct-10 | | 2-Nov-10 | | 8-Nov-10 | | 15-Nov-10 | | 2h IL-31 Challenge Response Comparisons | | |
|---|---|---|---|---|---|---|---|---|---|---|---|
| Day of Study | 1 | | 8 | | 14 | | 22 | | Day 8 vs. Day 1 | Day 14 vs. Day 1 | Day 21 vs. Day 1 |
| Dog ID | 30' BL | 2h IL-31 | 30' BL | 2h IL-31 | 30' BL | 2h IL-31 | 30' BL | 2h IL-31 | % Change | % Change | % Change |
| 4285068 | 4 | 58 | 0 | 77 | 0 | 102 | 0 | 82 | 32.8 | 75.86 | 41.4 |
| 4804228 | 5 | 71 | 3 | 114 | 2 | 114 | 4 | 112 | 60.6 | 60.56 | 57.7 |
| 4271963 | 4 | 37 | 2 | 39 | 0 | 41 | 3 | 52 | 5.4 | 10.81 | 40.5 |
| 4549040 | 1 | 48 | 3 | 72 | 2 | 76 | 3 | 72 | 50.0 | 58.33 | 50.0 |
| Mean | 3.5 | 54 | 2.0 | 76 | 1.0 | 83 | 2.5 | 80 | 37.2 | 51.4 | 47.4 |
| StError | 0.9 | 7 | 0.7 | 15 | 0.6 | 16 | 0.9 | 13 | 12.0 | 14.1 | 4.1 |

T02-Placebo @ 1X/d, SC on d0; Chim 11E12 @ 0.3mg/kg, SC on d7 (n=4)

| Date | 26-Oct-10 | | 2-Nov-10 | | 8-Nov-10 | | 15-Nov-10 | | 2h IL-31 Challenge Response Comparisons | | |
|---|---|---|---|---|---|---|---|---|---|---|---|
| Day of Study | 1 | | 8 | | 14 | | 22 | | Day 8 vs. Day 1 | Day 14 vs. Day 1 | Day 21 vs. Day 1 |
| Dog ID | 30' BL | 2h IL-31 | 30' BL | 2h IL-31 | 30' BL | 2h IL-31 | 30' BL | 2h IL-31 | % Change | % Change | % Change |
| 5427193 | 0 | 55 | 1 | 11 | 1 | 7 | 1 | 92 | (80.0) | (87.27) | 67.3 |
| 5853010 | 1 | 32 | 8 | 16 | 4 | 14 | 1 | 17 | (50.0) | (56.25) | (46.9) |
| 5353556 | 3 | 61 | 0 | 7 | 2 | 10 | 5 | 120 | (88.5) | (83.61) | 96.7 |
| 5044073 | 1 | 103 | 2 | 10 | 3 | 8 | 1 | 109 | (90.3) | (92.23) | 5.8 |
| Mean | 1.3 | 63 | 2.8 | 11 | 2.5 | 10 | 2.0 | 85 | (77.2) | (79.8) | 30.7 |
| StError | 0.6 | 15 | 1.8 | 2 | 0.6 | 2 | 1.0 | 23 | 9.3 | 8.1 | 32.1 |

11E12 Antibody
1. F40Y
2. S47P
3. Q49K
4. R50L
5. FW2

11E12 Antibody
1. Chimera
2. Caninized
3. Caninized light chain chimeric heavy chain
4. Chimeric light chain caninized heavy chain

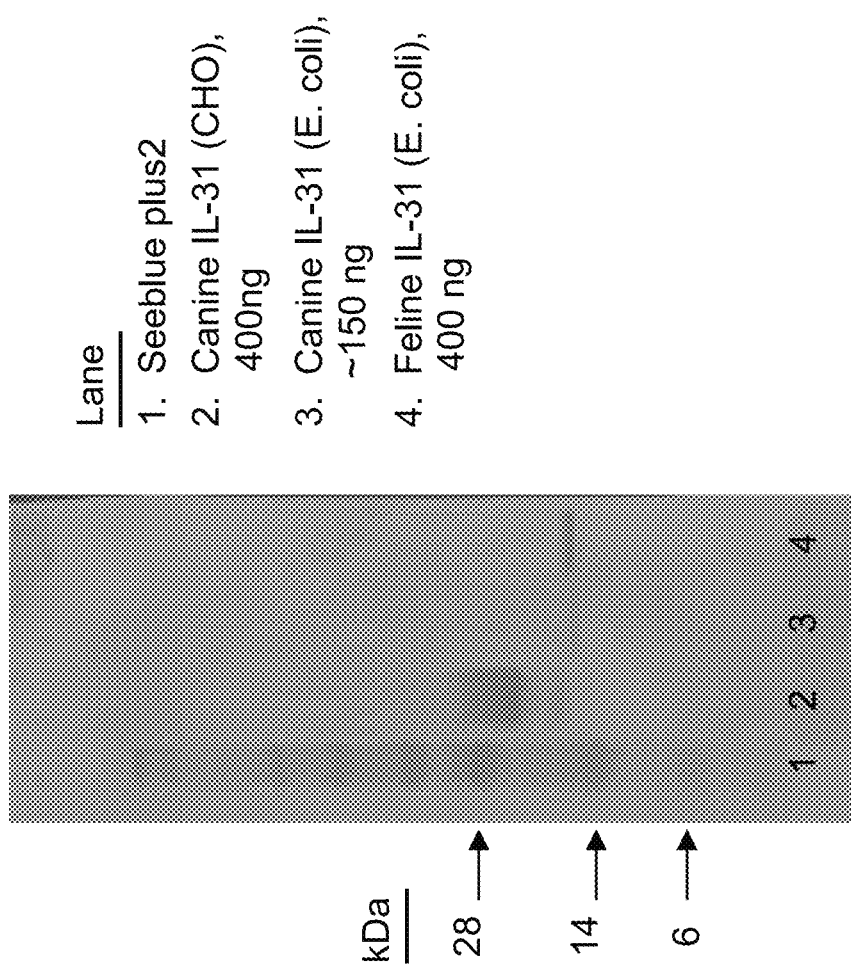

```
                         SEQUENCE LISTING

<160> NUMBER OF SEQ ID NOS: 80

<210> SEQ ID NO 1
<211> LENGTH: 5
<212> TYPE: PRT
<213> ORGANISM: Mus musculus

<400> SEQUENCE: 1

Tyr Tyr Asp Ile Asn
1               5

<210> SEQ ID NO 2
<211> LENGTH: 5
<212> TYPE: PRT
<213> ORGANISM: Mus musculus

<400> SEQUENCE: 2

Ser Tyr Asp Met Ser
1               5

<210> SEQ ID NO 3
<211> LENGTH: 5
<212> TYPE: PRT
<213> ORGANISM: Mus musculus

<400> SEQUENCE: 3

Asn Tyr Gly Met Ser
1               5

<210> SEQ ID NO 4
<211> LENGTH: 17
<212> TYPE: PRT
<213> ORGANISM: Mus musculus

<400> SEQUENCE: 4

Trp Ile Phe Pro Gly Asp Gly Gly Thr Lys Tyr Asn Glu Thr Phe Lys
1               5                   10                  15

Gly

<210> SEQ ID NO 5
<211> LENGTH: 17
<212> TYPE: PRT
<213> ORGANISM: Mus musculus

<400> SEQUENCE: 5

Thr Ile Thr Ser Gly Gly Gly Tyr Thr Tyr Ser Ala Asp Ser Val Lys
1               5                   10                  15

Gly

<210> SEQ ID NO 6
<211> LENGTH: 17
<212> TYPE: PRT
<213> ORGANISM: Mus musculus

<400> SEQUENCE: 6

Thr Ile Ser Tyr Gly Gly Ser Tyr Thr Tyr Tyr Pro Asp Asn Ile Lys
1               5                   10                  15

Gly
```

```
<210> SEQ ID NO 7
<211> LENGTH: 14
<212> TYPE: PRT
<213> ORGANISM: Mus musculus

<400> SEQUENCE: 7

Ala Arg Gly Gly Thr Ser Val Ile Arg Asp Ala Met Asp Tyr
1               5                   10

<210> SEQ ID NO 8
<211> LENGTH: 11
<212> TYPE: PRT
<213> ORGANISM: Mus musculus

<400> SEQUENCE: 8

Ala Arg Gln Asn Trp Val Val Gly Leu Ala Tyr
1               5                   10

<210> SEQ ID NO 9
<211> LENGTH: 11
<212> TYPE: PRT
<213> ORGANISM: Mus musculus

<400> SEQUENCE: 9

Val Arg Gly Tyr Gly Tyr Asp Thr Met Asp Tyr
1               5                   10

<210> SEQ ID NO 10
<211> LENGTH: 15
<212> TYPE: PRT
<213> ORGANISM: Mus musculus

<400> SEQUENCE: 10

Arg Ala Ser Glu Ser Val Asp Asn Tyr Gly Ile Ser Phe Met His
1               5                   10                  15

<210> SEQ ID NO 11
<211> LENGTH: 17
<212> TYPE: PRT
<213> ORGANISM: Mus musculus

<400> SEQUENCE: 11

Lys Ser Ser Gln Ser Leu Leu Asn Ser Gly Asn Gln Lys Asn Tyr Leu
1               5                   10                  15

Ala

<210> SEQ ID NO 12
<211> LENGTH: 15
<212> TYPE: PRT
<213> ORGANISM: Mus musculus

<400> SEQUENCE: 12

Lys Ala Ser Gln Ser Val Ser Phe Ala Gly Thr Gly Leu Met His
1               5                   10                  15

<210> SEQ ID NO 13
<211> LENGTH: 7
<212> TYPE: PRT
<213> ORGANISM: Mus musculus

<400> SEQUENCE: 13

Arg Ala Ser Asn Leu Glu Ser
1               5
```

```
<210> SEQ ID NO 14
<211> LENGTH: 7
<212> TYPE: PRT
<213> ORGANISM: Mus musculus

<400> SEQUENCE: 14

Gly Ala Ser Thr Arg Glu Ser
1               5

<210> SEQ ID NO 15
<211> LENGTH: 7
<212> TYPE: PRT
<213> ORGANISM: Mus musculus

<400> SEQUENCE: 15

Arg Ala Ser Asn Leu Glu Ala
1               5

<210> SEQ ID NO 16
<211> LENGTH: 9
<212> TYPE: PRT
<213> ORGANISM: Mus musculus

<400> SEQUENCE: 16

Gln Gln Ser Asn Lys Asp Pro Leu Thr
1               5

<210> SEQ ID NO 17
<211> LENGTH: 9
<212> TYPE: PRT
<213> ORGANISM: Mus musculus

<400> SEQUENCE: 17

Gln Asn Asp Tyr Ser Tyr Pro Tyr Thr
1               5

<210> SEQ ID NO 18
<211> LENGTH: 9
<212> TYPE: PRT
<213> ORGANISM: Mus musculus

<400> SEQUENCE: 18

Gln Gln Ser Arg Glu Tyr Pro Trp Thr
1               5

<210> SEQ ID NO 19
<211> LENGTH: 111
<212> TYPE: PRT
<213> ORGANISM: Mus musculus

<400> SEQUENCE: 19

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80
```

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Glu Leu Lys
            100                 105                 110

<210> SEQ ID NO 20
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 20

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110

<210> SEQ ID NO 21
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 21

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Phe Gln Gln Lys Pro Gly Gln Ser Pro
        35                  40                  45

Gln Leu Leu Ile Tyr Arg Ala Ser Asn Leu Glu Ser Gly Val Pro Asp
50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110

<210> SEQ ID NO 22
<211> LENGTH: 113
<212> TYPE: PRT
<213> ORGANISM: Mus musculus -continued

```
<400> SEQUENCE: 22

Asp Ile Val Met Ser Gln Ser Pro Ser Leu Ser Val Ser Ala Gly
1               5                   10                  15

Asp Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Trp Gln
            35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
                100                 105                 110

Lys

<210> SEQ ID NO 23
<211> LENGTH: 113
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 23

Glu Ile Val Met Thr Gln Ser Pro Ala Ser Leu Ser Leu Ser Gln Glu
1               5                   10                  15

Glu Lys Val Thr Ile Thr Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Ala Pro Lys Leu Leu Ile Tyr Gly Ala Ser Thr Arg Glu Ser Gly Val
    50                  55                  60

Pro Ser Arg Phe Ser Gly Ser Gly Ser Gly Thr Asp Phe Ser Phe Thr
65                  70                  75                  80

Ile Ser Ser Leu Glu Pro Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
                100                 105                 110

Lys

<210> SEQ ID NO 24
<211> LENGTH: 111
<212> TYPE: PRT
<213> ORGANISM: Mus musculus

<400> SEQUENCE: 24

Asp Ile Leu Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
                20                  25                  30

Gly Thr Gly Leu Met His Trp Tyr Gln Gln Lys Pro Gly Gln Gln Pro
            35                  40                  45

Lys Leu Leu Ile Tyr Arg Ala Ser Asn Leu Glu Ala Gly Val Pro Thr
    50                  55                  60
```

Arg Phe Ser Gly Ser Gly Ser Arg Thr Asp Phe Thr Leu Asn Ile His
65                  70                  75                  80

Pro Val Glu Glu Glu Asp Ala Ala Thr Tyr Phe Cys Gln Gln Ser Arg
                85                  90                  95

Glu Tyr Pro Trp Thr Phe Gly Gly Gly Thr Lys Leu Glu Ile Lys
            100                 105                 110

<210> SEQ ID NO 25
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 25

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Ser Val Ser Phe Ala
                20                  25                  30

Gly Thr Gly Leu Met His Trp Tyr Gln Gln Lys Pro Gly Gln Ala Pro
            35                  40                  45

Lys Leu Leu Ile Tyr Arg Ala Ser Asn Leu Glu Ala Gly Val Pro Ser
    50                  55                  60

Arg Phe Ser Gly Ser Gly Ser Gly Thr Asp Phe Ser Phe Thr Ile Ser
65                  70                  75                  80

Ser Leu Glu Pro Glu Asp Val Ala Val Tyr Tyr Cys Gln Gln Ser Arg
                85                  90                  95

Glu Tyr Pro Trp Thr Phe Gly Gln Gly Thr Lys Leu Glu Ile Lys
            100                 105                 110

<210> SEQ ID NO 26
<211> LENGTH: 121
<212> TYPE: PRT
<213> ORGANISM: Mus musculus

<400> SEQUENCE: 26

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Lys Tyr Tyr
                20                  25                  30

Asp Ile Asn Trp Val Arg Gln Arg Pro Glu Gln Gly Leu Glu Trp Ile
            35                  40                  45

Gly Trp Ile Phe Pro Gly Asp Gly Gly Thr Lys Tyr Asn Glu Thr Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gly Gly Thr Ser Val Ile Arg Asp Ala Met Asp Tyr Trp Gly
            100                 105                 110

Gln Gly Thr Ser Val Thr Val Ser Ser
        115                 120

<210> SEQ ID NO 27
<211> LENGTH: 121
<212> TYPE: PRT
<213> ORGANISM: Artificial

```
<220> FEATURE:
<223> OTHER INFORMATION: caninized variable heavy chain mAb sequence,
      from Mus musculus and Canis

<400> SEQUENCE: 27

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Lys Tyr Tyr
                20                  25                  30

Asp Ile Asn Trp Val Arg Gln Ala Pro Gly Ala Gly Leu Asp Trp Met
            35                  40                  45

Gly Trp Ile Phe Pro Gly Asp Gly Gly Thr Lys Tyr Asn Glu Thr Phe
50                  55                  60

Lys Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Gly Thr Ser Val Ile Arg Asp Ala Met Asp Tyr Trp Gly
            100                 105                 110

Gln Gly Thr Leu Val Thr Val Ser Ser
        115                 120

<210> SEQ ID NO 28
<211> LENGTH: 118
<212> TYPE: PRT
<213> ORGANISM: Mus musculus

<400> SEQUENCE: 28

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
                20                  25                  30

Asp Met Ser Trp Val Arg Gln Ile Pro Glu Lys Arg Leu Glu Trp Val
            35                  40                  45

Ala Thr Ile Thr Ser Gly Gly Gly Tyr Thr Tyr Ser Ala Asp Ser Val
50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Val Tyr Tyr Cys
                85                  90                  95

Ala Arg Gln Asn Trp Val Val Gly Leu Ala Tyr Trp Gly Gln Gly Thr
            100                 105                 110

Leu Val Thr Val Ser Ala
        115

<210> SEQ ID NO 29
<211> LENGTH: 118
<212> TYPE: PRT
<213> ORGANISM: Artificial
<220> FEATURE:
<223> OTHER INFORMATION: caninized variable heavy chain mAb sequence,
      from Mus musculus and Canis

<400> SEQUENCE: 29

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
                20                  25                  30
```

Asp Met Ser Trp Val Arg Gln Ala Pro Gly Lys Gly Leu Gln Trp Val
            35                  40                  45

Ala Thr Ile Thr Ser Gly Gly Gly Tyr Thr Tyr Ser Ala Asp Ser Val
 50                      55                  60

Lys Gly Arg Phe Thr Ile Ser Arg Asp Asn Ala Arg Asn Thr Leu Tyr
 65                  70                  75                  80

Leu Gln Met Asn Ser Leu Arg Ser Glu Asp Thr Ala Val Tyr Tyr Cys
                 85                  90                  95

Ala Arg Gln Asn Trp Val Val Gly Leu Ala Tyr Trp Gly Gln Gly Thr
             100                 105                 110

Leu Val Thr Val Ser Ser
         115

<210> SEQ ID NO 30
<211> LENGTH: 118
<212> TYPE: PRT
<213> ORGANISM: Mus musculus

<400> SEQUENCE: 30

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Ser Phe Ser Asn Tyr
                 20                  25                  30

Gly Met Ser Trp Val Arg Gln Thr Pro Asp Lys Arg Leu Glu Trp Val
            35                  40                  45

Ala Thr Ile Ser Tyr Gly Gly Ser Tyr Thr Tyr Tyr Pro Asp Asn Ile
 50                      55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Val Arg Gly Tyr Gly Tyr Asp Ser Met Asp Tyr Trp Gly Gln Gly Thr
             100                 105                 110

Ser Val Thr Val Ser Ser
         115

<210> SEQ ID NO 31
<211> LENGTH: 118
<212> TYPE: PRT
<213> ORGANISM: Artificial
<220> FEATURE:
<223> OTHER INFORMATION: caninized variable heavy chain mAb sequence,
      from Mus musculus and Canis

<400> SEQUENCE: 31

Glu Val Gln Leu Val Glu Ser Gly Gly Asp Leu Val Lys Pro Gly Gly
 1               5                  10                  15

Ser Leu Arg Leu Ser Cys Val Ala Ser Gly Phe Thr Phe Ser Asn Tyr
                 20                  25                  30

Gly Met Ser Trp Val Arg Gln Ala Pro Gly Lys Gly Leu Gln Trp Val
            35                  40                  45

Ala Thr Ile Ser Tyr Gly Gly Ser Tyr Thr Tyr Tyr Pro Asp Asn Ile
 50                      55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Val Arg Gly Tyr Gly Tyr Asp Thr Met Asp Tyr Trp Gly Gln Gly Thr
            100                 105                 110

Leu Val Thr Val Ser Ser
        115

<210> SEQ ID NO 32
<211> LENGTH: 159
<212> TYPE: PRT
<213> ORGANISM: Canis familiaris

<400> SEQUENCE: 32

Met Leu Ser His Thr Gly Pro Ser Arg Phe Ala Leu Phe Leu Leu Cys
1               5                   10                  15

Ser Met Glu Thr Leu Leu Ser Ser His Met Ala Pro Thr His Gln Leu
            20                  25                  30

Pro Pro Ser Asp Val Arg Lys Ile Ile Leu Glu Leu Gln Pro Leu Ser
        35                  40                  45

Arg Gly Leu Leu Glu Asp Tyr Gln Lys Lys Glu Thr Gly Val Pro Glu
    50                  55                  60

Ser Asn Arg Thr Leu Leu Leu Cys Leu Thr Ser Asp Ser Gln Pro Pro
65                  70                  75                  80

Arg Leu Asn Ser Ser Ala Ile Leu Pro Tyr Phe Arg Ala Ile Arg Pro
                85                  90                  95

Leu Ser Asp Lys Asn Ile Ile Asp Lys Ile Glu Gln Leu Asp Lys
            100                 105                 110

Leu Lys Phe Gln His Glu Pro Glu Thr Glu Ile Ser Val Pro Ala Asp
        115                 120                 125

Thr Phe Glu Cys Lys Ser Phe Ile Leu Thr Ile Leu Gln Gln Phe Ser
    130                 135                 140

Ala Cys Leu Glu Ser Val Phe Lys Ser Leu Asn Ser Gly Pro Gln
145                 150                 155

<210> SEQ ID NO 33
<211> LENGTH: 477
<212> TYPE: DNA
<213> ORGANISM: Canis familiaris

<400> SEQUENCE: 33
atgctctccc acacaggacc atccaggttt gccctgttcc tgctctgctc tatggaaacc      60
ttgctgtcct cccatatggc acccacccat cagctaccac caagtgatgt acgaaaaatc     120
atcttggaat tacagcccct gtcgagggga cttttggaag actatcagaa gaaagagaca     180
ggggtgccag aatccaaccg taccttgctg ctgtgtctca cctctgattc ccaaccacca     240
cgcctcaaca gctcagccat cttgccttat ttcagggcaa tcagaccatt atcagataag     300
aacattattg ataaaatcat agaacagctt gacaaactca aatttcaaca tgaaccagaa     360
acagaaattt ctgtgcctgc agatactttt gaatgtaaaa gcttcatctt gacgatttta     420
cagcagttct cggcgtgcct ggaaagtgtg tttaagtcac taaactctgg acctcag        477

<210> SEQ ID NO 34
<211> LENGTH: 333
<212> TYPE: DNA
<213> ORGANISM: Mus musculus

<400> SEQUENCE: 34
gacattgtgc tgacccaatc tccagcttct ttggctgtgt ctctagggca gagggccacc      60
atctcctgca gagccagcga aagtgttgat aattatggca ttagttttat gcactggtac     120

```
cagcagaaac caggacagcc acccaaactc ctcatctatc gtgcatccaa cctagaatct    180
gggatccctg ccaggttcag tggcagtggg tctaggacag acttcaccct caccattaat    240
cctgtggaga ctgatgatgt tgcaacctat tactgtcagc aaagtaataa ggatccgctc    300
acgttcggtg ctgggaccaa gctggagctg aaa                                 333
```

<210> SEQ ID NO 35
<211> LENGTH: 363
<212> TYPE: DNA
<213> ORGANISM: Mus musculus

<400> SEQUENCE: 35

```
caggttcagc tgcagcagtc tggagctgaa ctggtaaagc ctggggcttc agtgaagttg     60
tcctgcaagg cttctggcta caccttcaaa tactatgata aaactgggt gaggcagagg    120 cctgaacagg gacttgagtg gattggatgg atttttcctg agatggtgg tactaagtac    180 aatgagacgt tcaagggcaa ggccacactg actacagaca atcctccag cacagcctac    240 atgcagctca gcaggctgac atctgaggac tctgctgtct atttctgtgc aagaggggg    300 acttcggtga taagggatgc tatggactac tggggtcaag aacctcagt caccgtctcc    360 tca                                                                 363
```

<210> SEQ ID NO 36
<211> LENGTH: 339
<212> TYPE: DNA
<213> ORGANISM: Mus musculus

<400> SEQUENCE: 36

```
gacattgtga tgtcacagtc tccatcctcc ctgagtgtgt cagcaggaga taaggtcact     60
atgagctgca gtccagtca gagtctgtta acagtggaa atcaaaagaa ctacttggcc    120
tggtaccagc agaaaccatg gcagcctcct aaactgctga tctacggggc atccactagg    180
gaatctgggg tccctgatcg cttcacaggc agtggatctg gaacagattt cactctcacc    240
atcagcagtg tgcaggctga agacctggca gtttattact gtcagaatga ttatagttat    300
ccgtacacgt tcggaggggg gaccaagctg gaaataaaa                           339
```

<210> SEQ ID NO 37
<211> LENGTH: 354
<212> TYPE: DNA
<213> ORGANISM: Mus musculus

<400> SEQUENCE: 37

```
gaagtgaagc tggtggagtc tgggggaggc ttagtgaagc ctggagggtc cctgaaactc     60
tcctgtgcag cctctggatt cgctttcagc agctatgaca tgtcttgggt tcgccagatt    120
ccggaaaaga ggctggagtg gtcgcaacc attactagtg gtggtggtta cacctactct    180
gcagacagtg tgaagggccg attcaccatc tccagagaca tgccaggaa cacctgtac    240 ctgcaaatga gcagtctgag gtctgaggac acggccgtgt attattgtgc aagacaaaac    300
tgggtcgtgg ggttagctta ttggggccaa gggactctgg tcactgtctc tgca          354
```

<210> SEQ ID NO 38
<211> LENGTH: 333
<212> TYPE: DNA
<213> ORGANISM: Mus musculus

<400> SEQUENCE: 38

```
gacattttgc tgacccaatc tccagcttct ttggctgtgt ctctagggca gagggccatc      60
atctcctgca aggccagcca agtgtcagt  tttgctggta ctggtttaat gcactggtac     120
caacagaaac caggacagca acccaaactc ctcatctatc gtgcatccaa cctagaagct     180
ggggttccta ccaggtttag tggcagtggg tctaggacag acttcaccct caatatccat     240
cctgtggagg aggaggatgc tgcaacctat ttctgtcagc aaagcaggga atatccgtgg     300
acgttcggtg gaggcaccaa gctggaaatc aaa                                  333
```

<210> SEQ ID NO 39
<211> LENGTH: 353
<212> TYPE: DNA
<213> ORGANISM: Mus musculus

<400> SEQUENCE: 39

```
gaggtgcagt tggtggagtc tgggggagac ttagtgaagc ctggagggtc cctgaaactc      60
tcctgtgcag cctctggatt ctctttcagt aactatggca tgtcttgggt tcgccagact     120
ccagacaaga ggctggagtg ggtcgcaacc attagttatg gtggtagtta cacctactat     180
ccagacaata taaaggggcg attcaccatc tccagagaca atgccaagaa cacccctgtac    240
ctgcaaatga gcagtctgaa gtctgaggac acagccatgt attactgtgt aaggggggtat    300
ggttacgata ctatggacta ctggggtcaa ggaacctcag tcaccgtctc gag            353
```

<210> SEQ ID NO 40
<211> LENGTH: 331
<212> TYPE: PRT
<213> ORGANISM: Canis familiaris

<400> SEQUENCE: 40

```
Ala Ser Thr Thr Ala Pro Ser Val Phe Pro Leu Ala Pro Ser Cys Gly
 1               5                  10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu His Ser
    50                  55                  60

Leu Ser Ser Met Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Phe Asn Glu Cys Arg Cys Thr Asp Thr Pro Pro Cys Pro Val
            100                 105                 110

Pro Glu Pro Leu Gly Gly Pro Ser Val Leu Ile Phe Pro Pro Lys Pro
        115                 120                 125

Lys Asp Ile Leu Arg Ile Thr Arg Thr Pro Glu Val Thr Cys Val Val
    130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Ser Arg Glu Gln Gln
                165                 170                 175

Phe Asn Gly Thr Tyr Arg Val Val Ser Val Leu Pro Ile Glu His Gln
            180                 185                 190
```

Asp Trp Leu Thr Gly Lys Glu Phe Lys Cys Arg Val Asn His Ile Asp
            195                 200                 205

Leu Pro Ser Pro Ile Glu Arg Thr Ile Ser Lys Ala Arg Gly Arg Ala
        210                 215                 220

His Lys Pro Ser Val Tyr Val Leu Pro Pro Ser Pro Lys Glu Leu Ser
225                 230                 235                 240

Ser Ser Asp Thr Val Ser Ile Thr Cys Leu Ile Lys Asp Phe Tyr Pro
                245                 250                 255

Pro Asp Ile Asp Val Glu Trp Gln Ser Asn Gly Gln Gln Glu Pro Glu
            260                 265                 270

Arg Lys His Arg Met Thr Pro Pro Gln Leu Asp Glu Asp Gly Ser Tyr
        275                 280                 285

Phe Leu Tyr Ser Lys Leu Ser Val Asp Lys Ser Arg Trp Gln Gln Gly
    290                 295                 300

Asp Pro Phe Thr Cys Ala Val Met His Glu Thr Leu Gln Asn His Tyr
305                 310                 315                 320

Thr Asp Leu Ser Leu Ser His Ser Pro Gly Lys
                325                 330

<210> SEQ ID NO 41
<211> LENGTH: 993
<212> TYPE: DNA
<213> ORGANISM: Canis familiaris

<400> SEQUENCE: 41
gcctccacca cggcgccctc ggttttccca ctggccccca gctgcgggtc cacttccggc       60
tccacggtgg ccctggcctg cctggtgtca ggctacttcc ccgagcctgt aactgtgtcc      120
tggaactccg gctccttgac cagcggtgtg cacaccttcc cgtccgtcct gcagtcctca      180
gggcttcact ccctcagcag catggtgaca gtgccctcca gcaggtggcc cagcgagacc      240
ttcacctgca acgtggtcca cccagccagc aacactaaag tagacaagcc agtgttcaat      300
gaatgcagat gcactgatac ccccccatgc ccagtccctg aacctctggg agggccttcg      360
gtcctcatct ttcccccgaa acccaaggac atcctcagga ttacccgaac acccgaggtc      420
acctgtgtgg tgttagatct gggccgtgag gaccctgagg tgcagatcag ctggttcgtg      480
gatggtaagg aggtgcacac agccaagacc cagtctcgtg agcagcagtt caacggcacc      540
taccgtgtgg tcagcgtcct ccccattgag caccaggact ggctcacagg gaaggagttc      600
aagtgcagag tcaaccacat agacctcccg tctcccatcg agaggaccat ctctaaggcc      660
agagggaggg cccataagcc cagtgtgtat gtcctgccgc catccccaaa ggagttgtca      720
tccagtgaca cagtcagcat cacctgcctg ataaaagact tctacccacc tgacattgat      780
gtggagtggc agagcaatgg acagcaggag cccgagagga gcaccgcat gaccccgccc      840 cagctggacg aggacgggtc ctacttcctg tacagcaagc tctctgtgga caagagccgc      900
tggcagcagg gagaccccttc acatgtgcg gtgatgcatg aaactctaca gaaccactac      960
acagatctat ccctctccca ttctccgggt aaa                                   993

<210> SEQ ID NO 42
<211> LENGTH: 335
<212> TYPE: PRT
<213> ORGANISM: Canis familiaris

<400> SEQUENCE: 42

| | | | | | | | | | | | | | | | |
|---|---|---|---|---|---|---|---|---|---|---|---|---|---|---|---|
|Ala|Ser|Thr|Thr|Ala|Pro|Ser|Val|Phe|Pro|Leu|Ala|Pro|Ser|Cys|Gly|
|1| | | |5| | | | |10| | | | |15| |

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335

<210> SEQ ID NO 43
<211> LENGTH: 1005
<212> TYPE: DNA
<213> ORGANISM: Canis familiaris

<400> SEQUENCE: 43
gcctcaacaa ctgctcctag cgtgtttccc ctggccccta gctgcggaag tacctcaggc      60
agcacagtgg ccctggcttg tctggtgtct ggatatttcc ctgagccagt gaccgtgagt     120
tggaacagcg gctctctgac ctccggggtg cacacatttc catctgtgct gcagtctagt     180

```
ggcctgtact ccctgtcaag catggtgact gtgccttcct ctaggtggcc atcagaaact    240
ttcacctgca acgtggccca tcccgccagc aagaccaaag tggacaagcc cgtgcctaaa    300
agggagaatg aagggtgcc aagaccacct gattgcccta agtgtccagc tccagaaatg     360 ctggaggac caagcgtgtt catctttcca cccaagccca agacacact gctgattgct      420 agaactcccg aggtgacctg cgtggtggtg gacctggatc agaggaccc cgaagtgcag     480 atctcctggt tcgtggatgg gaagcagatg cagacagcca aaactcagcc tcggaggaa     540 cagtttaacg gaacctatag agtggtgtct gtgctgccaa ttggacacca ggactggctg    600
aagggcaaac agtttacatg caaggtgaac aacaaggccc tgcctagtcc aatcgagagg    660
actatttcaa aagctagggg acaggctcat cagccttccg tgtatgtgct gcctccatcc    720
cgggaggaac tgtctaagaa cacagtgagt ctgacttgtc tgatcaaaga tttctttccc    780
cctgacattg atgtggagtg gcagagcaat gggcagcagg agccagaatc caagtacaga    840
accacaccac cccagctgga cgaagatggc tcctatttcc tgtacagtaa gctgtcagtg    900
gacaaatcta ggtggcagcg cggggatacc tttatctgcg ccgtgatgca cgaggctctg    960
cacaatcatt acacacaaga aagtctgtca catagccccg gcaag                   1005

<210> SEQ ID NO 44
<211> LENGTH: 106
<212> TYPE: PRT
<213> ORGANISM: Canis familiaris

<400> SEQUENCE: 44

Arg Asn Asp Ala Gln Pro Ala Val Tyr Leu Phe Gln Pro Ser Pro Asp
 1               5                  10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105

<210> SEQ ID NO 45
<211> LENGTH: 318
<212> TYPE: DNA
<213> ORGANISM: Canis familiaris

<400> SEQUENCE: 45
aggaacgacg cccagcctgc tgtgtatctg tttcagccct cccctgatca gctgcacact     60
ggctctgcta gtgtggtgtg tctgctgaac agcttctacc caaaggatat caatgtgaag    120
tggaaagtgg acggcgtgat ccaggatact gggattcagg agtccgtgac cgaacaggac    180
aaagattcaa catatagcct gagctccact ctgaccatgt ctagtaccga gtacctgagc    240
cacgaactgt attcctgcga gatcactcat aagtccctgc cctctaccct gatcaagagc    300
ttccagagat cagagtgt                                                   318
```

<210> SEQ ID NO 46
<211> LENGTH: 339
<212> TYPE: DNA
<213> ORGANISM: Artificial
<220> FEATURE:
<223> OTHER INFORMATION: nucleotide sequence encoding a caninized
     variable light chain mAb sequence, from Mus musculus and Canis

<400> SEQUENCE: 46

```
gagatcgtga tgacccagag ccccgccagc ctgagcctga gccaggaaga gaaagtcacc    60
atcacatgca agagcagcca gagcctgctg aacagcggca accagaagaa ctacctggcc   120
tggtatcagc agaagcccgg ccaggccccc aagctgctga tctacggcgc cagcacccgc   180
gagagcggcg tgccaagcag attttccggc agcggctccg gcaccgactt cagcttcacc   240
atcagcagcc tggaacccga ggacgtggcc gtgtactact gccagaacga ctacagctac   300
ccctacacct tcggccaggg taccaagctg gagatcaag                          339
```

<210> SEQ ID NO 47
<211> LENGTH: 354
<212> TYPE: DNA
<213> ORGANISM: Artificial
<220> FEATURE:
<223> OTHER INFORMATION: nucleotide sequence encoding a caninized
     variable heavy chain mAb sequence, from Mus musculus and Canis

<400> SEQUENCE: 47

```
gaggtgcagc tggtggaatc tggcggcgac ctggtcaagc ctggcggcag cctgagactg    60
agctgtgtgg ccagcggctt caccttcagc agctacgaca tgagctgggt ccgacaggcc   120
cctggcaagg gactgcagtg ggtggccacc atcaccagcg gcggaggcta cacctacagc   180
gccgacagcg tgaagggccg gttcaccatc agccgggaca cgcccggaa caccctgtac   240 ctgcagatga acagcctgcg gagcgaggac accgccgtgt actactgcgc cagacagaac   300
tgggtcgtgg gcctggccta ctggggccag ggaacactcg tgaccgtctc gagc         354
```

<210> SEQ ID NO 48
<211> LENGTH: 333
<212> TYPE: DNA
<213> ORGANISM: Artificial
<220> FEATURE:
<223> OTHER INFORMATION: nucleotide sequence encoding a caninized
     variable light chain mAb sequence, from Mus musculus and Canis

<400> SEQUENCE: 48

```
gagatcgtga tgacccagag ccccgccagc ctgagcctga gccaggaaga gaaagtcacc    60
atcacatgca aggccagcca gagcgtgtcc ttcgccggca caggcctgat gcactggtat   120
cagcagaagc ccggccaggc ccccaagctg ctgatctacc gggccagcaa cctggaagcc   180
ggcgtgccaa gcagattcag cggcagcggc tccggcaccg acttcagctt caccatcagc   240
agcctcgaac ccgaggacgt ggccgtgtac tactgccagc agagcagaga gtacccctgg   300
accttcggcc agggtaccaa gctggagatc aag                                333
```

<210> SEQ ID NO 49
<211> LENGTH: 354
<212> TYPE: DNA
<213> ORGANISM: Artificial
<220> FEATURE:
<223> OTHER INFORMATION: nucleotide sequence encoding a caninized
     variable heavy chain mAb sequence, from Mus musculus and Canis

<400> SEQUENCE: 49

```
gaggtgcagc tggtggaatc tggcggcgac ctggtcaagc ctggcggcag cctgagactg    60
agctgtgtgg ccagcggctt caccttcagc aactacggca tgagctgggt ccgacaggcc   120
cctggcaagg gactgcagtg ggtggccacc atcagctacg gcggcagcta cacctactac   180
cccgacaaca tcaagggccg gttcaccatc agccgggaca cgccaagaa caccctgtac    240 ctgcagatga acagcctgcg ggccgaggac accgccatgt actactgcgt gcggggctac   300
ggctacgaca caatggacta ctggggccag ggcaccctcg tgaccgtctc gagc          354
```

<210> SEQ ID NO 50
<211> LENGTH: 333
<212> TYPE: DNA
<213> ORGANISM: Artificial
<220> FEATURE:
<223> OTHER INFORMATION: nucleotide sequence encoding a caninized
      variable light chain mAb sequence, from Mus musculus and Canis

<400> SEQUENCE: 50

```
gatatagtga tgacacaaac tcctctcagt ctttccgtat caccgggaga accggcttcc    60
atttcctgtc gggcctcaga gtctgtggac aactacggga tatccttcat gcactggtat   120
cagcagaaac ccggccagcc ccctaaactc cttatttaca gggccagtaa tctggaaagc   180
ggtgtgcccg atcgattag cggttccggg agcggcacag atttcaccct gcgaatctct    240
agagttgaag cggatgatgc aggagtatat tactgccagc aatccaataa ggatccccctt   300 acattcggcg cgggtaccaa gctggagatc aag                                 333
```

<210> SEQ ID NO 51
<211> LENGTH: 363
<212> TYPE: DNA
<213> ORGANISM: Artificial
<220> FEATURE:
<223> OTHER INFORMATION: nucleotide sequence encoding a caninized
      variable heavy chain mAb sequence, from Mus musculus and Canis

<400> SEQUENCE: 51

```
gaggtgcagc tggtgcagtc tggcgccgaa gtgaagaaac tggcgccag cgtgaaggtg     60 tcctgcaaga ccagcggcta caccttcaag tactacgaca tcaactgggt ccgacaggcc   120
cctggcgccg gactggattg gatgggctgg atcttccccg gcgacggcgg caccaagtac   180
aacgagacat tcaagggcag agtgaccctg accgccgaca ccagcaccag caccgcctac   240
atggaactga gcagcctgag agccggcgat atcgctgtgt actactgcgc cagaggcggc   300
accagcgtga tccgggacgc tatggactac tggggccagg gcaccctcgt gaccgtctcg   360
agc                                                                 363
```

<210> SEQ ID NO 52
<211> LENGTH: 333
<212> TYPE: DNA
<213> ORGANISM: Artificial
<220> FEATURE:
<223> OTHER INFORMATION: nucleotide sequence encoding a caninized
      variable light chain mAb sequence, from Mus musculus and Canis

<400> SEQUENCE: 52

```
gacattgtta tgactcagac gcccctgagc ctgagcgtct cccccggcga gcccgctagt    60
attagttgcc gggcatccga gtcagtggac aattatggca tcagctttat gcattggttt   120
cagcagaaac caggtcagtc ccctcaactc ctgatttaca gagcttccaa tctggaatca   180
```

```
ggcgttcctg acagatttag cggatcaggc tccgggacag atttcaccct gcgcatcagt    240
cgcgtggaag ccgatgacgc aggcgtctat tattgtcaac agtccaacaa ggatcccctt    300
acattcggag ccggtaccaa gctggagatc aag                                 333
```

<210> SEQ ID NO 53
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 53

```
Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Phe Gln Gln Lys Pro Gly Gln Ser Pro
        35                  40                  45

Gln Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110
```

<210> SEQ ID NO 54
<211> LENGTH: 333
<212> TYPE: DNA
<213> ORGANISM: Artificial
<220> FEATURE:
<223> OTHER INFORMATION: nucleotide sequence encoding a caninized
      variable light chain mAb sequence, from Mus musculus and Canis

<400> SEQUENCE: 54

```
gacatcgtga tgacccagac cccccctgagc ctgagcgtgt cccctggcga gcctgccagc    60
atcagctgca gagccagcga gagcgtggac aactacggca tcagcttcat gcactggttc    120
cagcagaagc ccggccagag ccccagcgg ctgatctaca gagccagcaa cctggaaagc    180
ggcgtgcccg atcggtttag cggctctggc agcggcaccg acttcaccct gcggatctct    240
cgggtggaag ccgatgacgc cggagtgtac tactgccagc agagcaacaa ggaccccctg    300
acctttggcg ccggtaccaa gctggagatc aag                                 333
```

<210> SEQ ID NO 55
<211> LENGTH: 148
<212> TYPE: PRT
<213> ORGANISM: Artificial
<220> FEATURE:
<223> OTHER INFORMATION: canine IL-31 full length protein encoded by
      codon-optimized nucleotide sequence

<400> SEQUENCE: 55

```
Met Arg Gly Ser His His His His His His Gly Ser Ser His Met Ala
1               5                   10                  15

Pro Thr His Gln Leu Pro Pro Ser Asp Val Arg Lys Ile Ile Leu Glu
            20                  25                  30
```

Leu Gln Pro Leu Ser Arg Gly Leu Leu Glu Asp Tyr Gln Lys Lys Glu
        35                  40                  45

Thr Gly Val Pro Glu Ser Asn Arg Thr Leu Leu Leu Cys Leu Thr Ser
 50                  55                  60

Asp Ser Gln Pro Pro Arg Leu Asn Ser Ser Ala Ile Leu Pro Tyr Phe
65                  70                  75                  80

Arg Ala Ile Arg Pro Leu Ser Asp Lys Asn Ile Ile Asp Lys Ile Ile
                85                  90                  95

Glu Gln Leu Asp Lys Leu Lys Phe Gln His Glu Pro Glu Thr Glu Ile
            100                 105                 110

Ser Val Pro Ala Asp Thr Phe Glu Cys Lys Ser Phe Ile Leu Thr Ile
            115                 120                 125

Leu Gln Gln Phe Ser Ala Cys Leu Glu Ser Val Phe Lys Ser Leu Asn
    130                 135                 140

Ser Gly Pro Gln
145

<210> SEQ ID NO 56
<211> LENGTH: 444
<212> TYPE: DNA
<213> ORGANISM: Artificial
<220> FEATURE:
<223> OTHER INFORMATION: codon-optimized nucleotide sequence encoding
      canine IL-31 full-length protein

<400> SEQUENCE: 56
atgagaggat cccatcacca tcaccaccac ggctcatctc atatggctcc tactcaccaa      60
ttaccaccct ccgatgtccg taaaattatt ctcgaattac aacctttatc ccgcggtctg     120
ctcgaagatt accaaaaaaa agaaacaggc gtcccagaaa gcaaccgtac attactcctt     180
tgccttacct ccgattccca accacctcgt cttaactcat cagccattct cccttatttc     240
cgtgccattc gccctctttc tgataaaaat attattgaca aaattattga acaactcgac     300
aaattaaaat tccaacacga acccgaaacc gaaatctccg tacctgccga tacctttgaa     360
tgcaaatcct ttatcctcac tattttacaa caattctccg catgtctcga atccgtcttc     420
aaatctctca attccggtcc acag                                             444

<210> SEQ ID NO 57
<211> LENGTH: 151
<212> TYPE: PRT
<213> ORGANISM: Artificial
<220> FEATURE:
<223> OTHER INFORMATION: amino acid sequence corresponding to canine
      IL-31 protein with N-terminal truncation (-20N)

<400> SEQUENCE: 57

Met Leu Glu Leu Gln Pro Leu Ser Arg Gly Leu Leu Glu Asp Tyr Gln
 1               5                  10                  15

Lys Lys Glu Thr Gly Val Pro Glu Ser Asn Arg Thr Leu Leu Leu Cys
                20                  25                  30

Leu Thr Ser Asp Ser Gln Pro Pro Arg Leu Asn Ser Ser Ala Ile Leu
            35                  40                  45

Pro Tyr Phe Arg Ala Ile Arg Pro Leu Ser Asp Lys Asn Ile Ile Asp
    50                  55                  60

Lys Ile Ile Glu Gln Leu Asp Lys Leu Lys Phe Gln His Glu Pro Glu
65                  70                  75                  80

Thr Glu Ile Ser Val Pro Ala Asp Thr Phe Glu Cys Lys Ser Phe Ile
                85                  90                  95

```
Leu Thr Ile Leu Gln Gln Phe Ser Ala Cys Leu Glu Ser Val Phe Lys
                100                 105                 110
Ser Leu Asn Ser Gly Pro Gln Lys Gly Glu Leu Asn Ser Lys Leu Glu
            115                 120                 125
Gly Lys Pro Ile Pro Asn Pro Leu Leu Gly Leu Asp Ser Thr Arg Thr
        130                 135                 140
Gly His His His His His
145                 150
```

<210> SEQ ID NO 58
<211> LENGTH: 456
<212> TYPE: DNA
<213> ORGANISM: Artificial
<220> FEATURE:
<223> OTHER INFORMATION: nucleotide sequence encoding canine IL-31
      protein with N-terminal truncation (-20N)

<400> SEQUENCE: 58

```
atgctcgaat acaacctttt atcccgcggt ctgctcgaag attaccaaaa aaaagaaaca     60
ggcgtcccag aaagcaaccg tacattactc ctttgcctta cctccgattc caaccacct    120
cgtcttaact catcagccat tctcccttat ttccgtgcca ttcgccctct ttctgataaa    180
aatattattg acaaaattat tgaacaactc gacaaattaa aattccaaca cgaacccgaa    240
accgaaatct ccgtacctgc cgatacctttt gaatgcaaat cctttatcct cactatttta    300
caacaattct ccgcatgtct cgaatccgtc ttcaaatctc tcaattccgg tccacagaag    360
ggcgagctca attcgaagct tgaaggtaag cctatcccta accctctcct cggtctcgat    420
tctacgcgta ccggtcatca tcaccatcac cattga                              456
```

<210> SEQ ID NO 59
<211> LENGTH: 131
<212> TYPE: PRT
<213> ORGANISM: Artificial
<220> FEATURE:
<223> OTHER INFORMATION: amino acid sequence corresponding to canine
      IL-31 protein with N-terminal truncation (-40N)

<400> SEQUENCE: 59

```
Met Val Pro Glu Ser Asn Arg Thr Leu Leu Leu Cys Leu Thr Ser Asp
1               5                   10                  15
Ser Gln Pro Pro Arg Leu Asn Ser Ala Ile Leu Pro Tyr Phe Arg
            20                  25                  30
Ala Ile Arg Pro Leu Ser Asp Lys Asn Ile Ile Asp Lys Ile Ile Glu
        35                  40                  45
Gln Leu Asp Lys Leu Lys Phe Gln His Glu Pro Glu Thr Glu Ile Ser
    50                  55                  60
Val Pro Ala Asp Thr Phe Glu Cys Lys Ser Phe Ile Leu Thr Ile Leu
65                  70                  75                  80
Gln Gln Phe Ser Ala Cys Leu Glu Ser Val Phe Lys Ser Leu Asn Ser
                85                  90                  95
Gly Pro Gln Lys Gly Glu Leu Asn Ser Lys Leu Glu Gly Lys Pro Ile
            100                 105                 110
Pro Asn Pro Leu Leu Gly Leu Asp Ser Thr Arg Thr Gly His His His
        115                 120                 125
His His His
    130
```

<210> SEQ ID NO 60
<211> LENGTH: 393
<212> TYPE: DNA
<213> ORGANISM: Artificial
<220> FEATURE:
<223> OTHER INFORMATION: nucleotide sequence encoding canine IL-31 protein with N-terminal truncation (-40N)

<400> SEQUENCE: 60

```
atggtcccag aaagcaaccg tacattactc ctttgcctta cctccgattc ccaaccacct      60
cgtcttaact catcagccat tctcccttat ttccgtgcca ttcgccctct ttctgataaa     120
aatattattg acaaaattat tgaacaactc gacaaattaa aattccaaca cgaacccgaa     180
accgaaatct ccgtacctgc cgataccttt gaatgcaaat cctttatcct cactatttta     240
caacaattct ccgcatgtct cgaatccgtc ttcaaatctc tcaattccgg tccacagaag     300
ggcgagctca attcgaagct tgaaggtaag cctatcccta accctctcct cggtcwcgat     360
tctacgcgta ccggtcatca tcaccatcac cat                                  393
```

<210> SEQ ID NO 61
<211> LENGTH: 111
<212> TYPE: PRT
<213> ORGANISM: Artificial
<220> FEATURE:
<223> OTHER INFORMATION: amino acid sequence corresponding to canine IL-31 protein with N-terminal truncation (-60N)

<400> SEQUENCE: 61

```
Met Leu Asn Ser Ser Ala Ile Leu Pro Tyr Phe Arg Ala Ile Arg Pro
1               5                   10                  15
Leu Ser Asp Lys Asn Ile Ile Asp Lys Ile Ile Glu Gln Leu Asp Lys
            20                  25                  30
Leu Lys Phe Gln His Glu Pro Glu Thr Glu Ile Ser Val Pro Ala Asp
        35                  40                  45
Thr Phe Glu Cys Lys Ser Phe Ile Leu Thr Ile Leu Gln Gln Phe Ser
    50                  55                  60
Ala Cys Leu Glu Ser Val Phe Lys Ser Leu Asn Ser Gly Pro Gln Lys
65                  70                  75                  80
Gly Glu Leu Asn Ser Lys Leu Glu Gly Lys Pro Ile Pro Asn Pro Leu
                85                  90                  95
Leu Gly Leu Asp Ser Thr Arg Thr Gly His His His His His His
            100                 105                 110
```

<210> SEQ ID NO 62
<211> LENGTH: 333
<212> TYPE: DNA
<213> ORGANISM: Artificial
<220> FEATURE:
<223> OTHER INFORMATION: nucleotide sequence encoding canine IL-31 protein with N-terminal truncation (-60N)

<400> SEQUENCE: 62

```
atgcttaact catcagccat tctcccttat ttccgtgcca ttcgccctct ttctgataaa      60
aatattattg acaaaattat tgaacaactc gacaaattaa aattccaaca cgaacccgaa     120
accgaaatct ccgtacctgc cgataccttt gaatgcaaat cctttatcct cactatttta     180
caacaattct ccgcatgtct cgaatccgtc ttcaaatctc tcaattccgg tccacagaag     240
ggcgagctca attcgaagct tgaaggtaag cctatcccta accctctcct cggtctcgat     300
tctacgcgta ccggtcatca tcaccatcac cat                                  333
```

<210> SEQ ID NO 63
<211> LENGTH: 136
<212> TYPE: PRT
<213> ORGANISM: Artificial
<220> FEATURE:
<223> OTHER INFORMATION: amino acid sequence corresponding to canine
      IL-31 protein with C-terminal truncation at position 20-122

<400> SEQUENCE: 63

Met Leu Glu Leu Gln Pro Leu Ser Arg Gly Leu Leu Glu Asp Tyr Gln
1               5                   10                  15

Lys Lys Glu Thr Gly Val Pro Glu Ser Asn Arg Thr Leu Leu Leu Cys
            20                  25                  30

Leu Thr Ser Asp Ser Gln Pro Pro Arg Leu Asn Ser Ser Ala Ile Leu
        35                  40                  45

Pro Tyr Phe Arg Ala Ile Arg Pro Leu Ser Asp Lys Asn Ile Ile Asp
    50                  55                  60

Lys Ile Ile Glu Gln Leu Asp Lys Leu Lys Phe Gln His Glu Pro Glu
65                  70                  75                  80

Thr Glu Ile Ser Val Pro Ala Asp Thr Phe Glu Cys Lys Ser Phe Ile
                85                  90                  95

Leu Thr Ile Leu Gln Gln Phe Ser Lys Gly Leu Asn Ser Lys Leu
            100                 105                 110

Glu Gly Lys Pro Ile Pro Asn Pro Leu Leu Gly Leu Asp Ser Thr Arg
        115                 120                 125

Thr Gly His His His His His His
        130                 135

<210> SEQ ID NO 64
<211> LENGTH: 411
<212> TYPE: DNA
<213> ORGANISM: Artificial
<220> FEATURE:
<223> OTHER INFORMATION: nucleotide sequence encoding canine IL-31
      protein with C-terminal truncation at position 20-122

<400> SEQUENCE: 64
atgctcgaat tcaaccttt  atcccgcggt ctgctcgaag attaccaaaa aaaagaaaca      60
ggcgtcccag aaagcaaccg tacattactc ctttgcctta cctccgattc ccaaccacct     120
cgtcttaact catcagccat tctcccttat ttccgtgcca ttcgccctct ttctgataaa     180
aatattattg acaaaattat tgaacaactc gacaaattaa aattccaaca cgaacccgaa     240
accgaaatct ccgtacctgc cgataccttt gaatgcaaat cctttatcct cactattta      300 caacaattct ccaagggcga gctcaattcg aagcttgaag gtaagcctat ccctaaccct     360
ctcctcggtc tcgattctac gcgtaccggt catcatcacc atcaccattg a              411

<210> SEQ ID NO 65
<211> LENGTH: 114
<212> TYPE: PRT
<213> ORGANISM: Artificial
<220> FEATURE:
<223> OTHER INFORMATION: amino acid sequence corresponding to canine
      IL-31 protein with C-terminal truncation at position 20-100

<400> SEQUENCE: 65

Met Leu Glu Leu Gln Pro Leu Ser Arg Gly Leu Leu Glu Asp Tyr Gln
1               5                   10                  15

Lys Lys Glu Thr Gly Val Pro Glu Ser Asn Arg Thr Leu Leu Leu Cys
            20                  25                  30

```
Leu Thr Ser Asp Ser Gln Pro Pro Arg Leu Asn Ser Ser Ala Ile Leu
            35                  40                  45

Pro Tyr Phe Arg Ala Ile Arg Pro Leu Ser Asp Lys Asn Ile Ile Asp
 50                  55                  60

Lys Ile Ile Glu Gln Leu Asp Lys Leu Lys Phe Gln His Glu Pro Glu
 65                  70                  75                  80

Thr Glu Lys Gly Glu Leu Asn Ser Lys Leu Glu Gly Lys Pro Ile Pro
                 85                  90                  95

Asn Pro Leu Leu Gly Leu Asp Ser Thr Arg Thr Gly His His His His
            100                 105                 110

His His

<210> SEQ ID NO 66
<211> LENGTH: 345
<212> TYPE: DNA
<213> ORGANISM: Artificial
<220> FEATURE:
<223> OTHER INFORMATION: nucleotide sequence encoding canine IL-31
      protein with C-terminal truncation at position 20-100

<400> SEQUENCE: 66
atgctcgaat tacaaccttt atcccgcggt ctgctcgaag attaccaaaa aaagaaaaca      60
ggcgtcccag aaagcaaccg tacattactc ctttgcctta cctccgattc ccaaccacct    120
cgtcttaact catcagccat tctcccttat ttccgtgcca ttcgccctct ttctgataaa    180
aatattattg acaaaattat tgaacaactc gacaaattaa aattccaaca cgaacccgaa    240
accgaaaagg gcgagctcaa ttcgaagctt gaaggtaagc ctatccctaa ccctctcctc    300
ggtctcgatt ctacgcgtac cggtcatcat caccatcacc attga                    345

<210> SEQ ID NO 67
<211> LENGTH: 94
<212> TYPE: PRT
<213> ORGANISM: Artificial
<220> FEATURE:
<223> OTHER INFORMATION: amino acid sequence corresponding to canine
      IL-31 protein with C-terminal truncation at position 20-80

<400> SEQUENCE: 67

Met Leu Glu Leu Gln Pro Leu Ser Arg Gly Leu Leu Glu Asp Tyr Gln
 1               5                  10                  15

Lys Lys Glu Thr Gly Val Pro Glu Ser Asn Arg Thr Leu Leu Leu Cys
             20                  25                  30

Leu Thr Ser Asp Ser Gln Pro Pro Arg Leu Asn Ser Ser Ala Ile Leu
            35                  40                  45

Pro Tyr Phe Arg Ala Ile Arg Pro Leu Ser Asp Lys Asn Ile Lys Gly
 50                  55                  60

Glu Leu Asn Ser Lys Leu Glu Gly Lys Pro Ile Pro Asn Pro Leu Leu
 65                  70                  75                  80

Gly Leu Asp Ser Thr Arg Thr Gly His His His His His
             85                  90

<210> SEQ ID NO 68
<211> LENGTH: 285
<212> TYPE: DNA
<213> ORGANISM: Artificial
<220> FEATURE:
<223> OTHER INFORMATION: nucleotide sequence encoding canine IL-31
      protein with C-terminal truncation at position 20-80
```

<400> SEQUENCE: 68

```
atgctcgaat tcaaccttt atcccgcggt ctgctcgaag attaccaaaa aaaagaaaca    60
ggcgtcccag aaagcaaccg tacattactc ctttgcctta cctccgattc ccaaccacct   120
cgtcttaact catcagccat tctcccttat ttccgtgcca ttcgccctct ttctgataaa   180
aatattaagg gcgagctcaa ttcgaagctt gaaggtaagc ctatccctaa ccctctcctc   240
ggtctcgatt ctacgcgtac cggtcatcat caccatcacc attga                  285
```

<210> SEQ ID NO 69
<211> LENGTH: 444
<212> TYPE: DNA
<213> ORGANISM: Felis catus

<400> SEQUENCE: 69

```
atgagaggat cccatcacca tcaccaccac ggctcatctc atatgccccc cgcacatcgc    60
ctgcagccga gtgacattcg taaaattatc ttggagctgc gcccgatgtc caagggctta   120
ctgcaggatt atctgaagaa agagatcggg ctgcctgaaa gcaaccatag tagcctgccg   180
tgtttatcgt ctgatagcca gttaccacac atcaatggct ctgcgatttt gccctacttt   240
cgcgccatcc gtccgctgtc cgataaaaat accatcgaca aaattatcga caactggat   300
aaattgaagt tcagcgcga gcctgaagcg aaagtttcga tgccagcmga taacttcgaa   360
cgcaaaaact ttatttttagc ggtgttgcag cagttttctg cctgtctgga acacgtgctc   420
cagtcactca atagtgggcc acaa                                         444
```

<210> SEQ ID NO 70
<211> LENGTH: 148
<212> TYPE: PRT
<213> ORGANISM: Felis catus

<400> SEQUENCE: 70

```
Met Arg Gly Ser His His His His His Gly Ser Ser His Met Ala
1               5                   10                  15

Pro Ala His Arg Leu Gln Pro Ser Asp Ile Arg Lys Ile Ile Leu Glu
            20                  25                  30

Leu Arg Pro Met Ser Lys Gly Leu Leu Gln Asp Tyr Leu Lys Lys Glu
        35                  40                  45

Ile Gly Leu Pro Glu Ser Asn His Ser Ser Leu Pro Cys Leu Ser Ser
    50                  55                  60

Asp Ser Gln Leu Pro His Ile Asn Gly Ser Ala Ile Leu Pro Tyr Phe
65                  70                  75                  80

Arg Ala Ile Arg Pro Leu Ser Asp Lys Asn Thr Ile Asp Lys Ile Ile
                85                  90                  95

Glu Gln Leu Asp Lys Leu Lys Phe Gln Arg Glu Pro Glu Ala Lys Val
            100                 105                 110

Ser Met Pro Ala Asp Asn Phe Glu Arg Lys Asn Phe Ile Leu Ala Val
        115                 120                 125

Leu Gln Gln Phe Ser Ala Cys Leu Glu His Val Leu Gln Ser Leu Asn
    130                 135                 140

Ser Gly Pro Gln
145
```

<210> SEQ ID NO 71
<211> LENGTH: 111
<212> TYPE: PRT
<213> ORGANISM: Artificial

<220> FEATURE:
<223> OTHER INFORMATION: felinized variable light chain mAb sequence,
      from Mus musculus and Felis catus

<400> SEQUENCE: 71

Glu Ile Gln Met Thr Gln Ser Pro Ser Ser Leu Ser Ala Ser Pro Gly
1               5                   10                  15

Asp Arg Val Thr Ile Thr Cys Lys Ala Ser Gln Ser Val Ser Phe Ala
            20                  25                  30

Gly Thr Gly Leu Met His Trp Tyr Gln Gln Lys Pro Gly Lys Val Pro
        35                  40                  45

Lys Leu Leu Ile Tyr Arg Ala Ser Asn Leu Glu Ala Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Arg
                85                  90                  95

Glu Tyr Pro Trp Thr Phe Gly Gln Gly Thr Lys Leu Glu Ile Lys
            100                 105                 110

<210> SEQ ID NO 72
<211> LENGTH: 333
<212> TYPE: DNA
<213> ORGANISM: Artificial
<220> FEATURE:
<223> OTHER INFORMATION: nucleotide sequence encoding a felinized
      variable light chain mAb sequence, from Mus musculus and Felis
      catus

<400> SEQUENCE: 72
gagattcaaa tgacccagag tcctagctca ctgagcgcat cacccgggga ccgcgtgacc      60
atcacgtgca aggcatctca gtccgtgtca ttcgctggaa ccggtctgat gcactggtat     120
cagcaaaaac cagggaaagt ccctaaactg ctgatctatc gcgcctccaa tcttgaggcc     180
ggggtgccat ctcggttctc tggtagcggc agcggaactg actttaccct gacaatctcc     240
tcactcgagc ctgaagacgc cgccacctac tactgtcaac agtccagaga atacccatgg     300
acctttggac agggtaccaa gctggagatc aaa                                  333

<210> SEQ ID NO 73
<211> LENGTH: 118
<212> TYPE: PRT
<213> ORGANISM: Artificial
<220> FEATURE:
<223> OTHER INFORMATION: felinized variable heavy chain mAb sequence,
      from Mus musculus and Felis catus

<400> SEQUENCE: 73

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Asn Tyr
            20                  25                  30

Gly Met Ser Trp Val Arg Gln Ala Pro Gly Lys Gly Leu Gln Trp Val
        35                  40                  45

Ala Thr Ile Ser Tyr Gly Gly Ser Tyr Thr Tyr Tyr Pro Asp Asn Ile
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Tyr Tyr Cys
                85                  90                  95

Val Arg Gly Tyr Gly Tyr Asp Thr Met Asp Tyr Trp Gly Gln Gly Thr
            100                 105                 110

Leu Val Thr Val Ser Ser
        115

<210> SEQ ID NO 74
<211> LENGTH: 354
<212> TYPE: DNA
<213> ORGANISM: Artificial
<220> FEATURE:
<223> OTHER INFORMATION: nucleotide sequence encoding a felinized
      variable heavy chain mAb sequence, from Mus musculus and Felis
      catus

<400> SEQUENCE: 74
gacgtgcaac tggtcgaaag cggaggcgat cttgtgaagc caggtgggag tctccggctc      60
acatgcgtgg cctctggctt tacctacagc aactacggga tgagttgggt tcgccaggca     120
ccaggaaagg gcctgcaatg ggtggccact ataagctatg gtgggtccta tacctactac     180
cctgataata tcaaggggag attcactatt tcccgcgaca tgctaagaa tactctctac     240 ctccagatga atagcctgaa gactgaggat accgctacct actattgcgt gcgcggctac     300
ggctacgata ccatggacta ctggggacag gaacccttg tcactgtctc gagc            354

<210> SEQ ID NO 75
<211> LENGTH: 335
<212> TYPE: PRT
<213> ORGANISM: Felis catus

<400> SEQUENCE: 75

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
            245                 250                 255

Ser Phe His Pro Pro Asp Ile Ala Val Glu Trp Glu Ile Thr Gly Gln
        260                 265                 270

Pro Glu Pro Glu Asn Asn Tyr Arg Thr Thr Pro Pro Gln Leu Asp Ser
    275                 280                 285

Asp Gly Thr Tyr Phe Val Tyr Ser Lys Leu Ser Val Asp Arg Ser His
290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335

<210> SEQ ID NO 76
<211> LENGTH: 1005
<212> TYPE: DNA
<213> ORGANISM: Felis catus

<400> SEQUENCE: 76
gcctccacca cggcccatc ggtgttccca ctggccccca gctgcgggac cacatctggc      60
gccaccgtgg ccctggcctg cctggtgtta ggctacttcc ctgagccggt gaccgtgtcc    120
tggaactccg gcgccctgac cagcggtgtg cacaccttcc cggccgtcct gcaggcctcg    180
gggctgtact ctctcagcag catggtgaca gtgccctcca gcaggtggct cagtgacacc    240
ttcacctgca acgtggccca cccgcccagc aacaccaagg tggacaagac cgtgcgcaaa    300
acagaccacc caccgggacc caaaccctgc gactgtccca atgcccaccc cctgagatg     360 cttggaggac cgtccatctt catcttcccc ccaaaaccca aggacaccct ctcgatttcc    420
cggacgcccg aggtcacatg cttggtggtg gacttgggcc agatgactc cgatgtccag     480 atcacatggt ttgtggataa cacccaggtg tacacagcca agacgagtcc gcgtgaggag    540
cagttcaaca gcacctaccg tgtggtcagt gtcctcccca tcctacacca ggactggctc    600
aaggggaagg agttcaagtg caaggtcaac agcaaatccc tcccctcccc catcgagagg    660
accatctcca aggccaaagg acagccccac gagcccagg tgtacgtcct gcctccagcc     720
caggaggagc tcagcaggaa caaagtcagt gtgacctgcc tgatcaaatc cttccacccg    780
cctgacattg ccgtcgagtg ggagatcacc ggacagccgg agccagagaa caactaccgg    840
acgaccccgc cccagctgga cagcgacggg acctacttcg tgtacagcaa gctctcggtg    900
gacaggtccc actggcagag gggaaacacc tacacctgct cggtgtcaca cgaagctctg    960
cacagccacc acacacagaa atccctcacc cagtctccgg gtaaa                   1005

<210> SEQ ID NO 77
<211> LENGTH: 110
<212> TYPE: PRT
<213> ORGANISM: Felis catus

<400> SEQUENCE: 77

Arg Ser Asp Ala Gln Pro Ser Val Phe Leu Phe Gln Pro Ser Leu Asp
1               5                   10                  15

Glu Leu His Thr Gly Ser Ala Ser Ile Val Cys Ile Leu Asn Asp Phe
            20                  25                  30

Tyr Pro Lys Glu Val Asn Val Lys Trp Lys Val Asp Gly Val Val Gln
        35                  40                  45

Asn Lys Gly Ile Gln Glu Ser Thr Thr Glu Gln Asn Ser Lys Asp Ser
 50                  55                  60

Thr Tyr Ser Leu Ser Ser Thr Leu Thr Met Ser Ser Thr Glu Tyr Gln
65                  70                  75                  80

Ser His Glu Lys Phe Ser Cys Glu Val Thr His Lys Ser Leu Ala Ser
                85                  90                  95

Thr Leu Val Lys Ser Phe Asn Arg Ser Glu Cys Gln Arg Glu
                100                 105                 110

<210> SEQ ID NO 78
<211> LENGTH: 330
<212> TYPE: DNA
<213> ORGANISM: Felis catus

<400> SEQUENCE: 78
cggagtgatg ctcagccatc tgtctttctc ttccaaccat ctctggacga gttacataca      60
ggaagtgcct ctatcgtgtg catattgaat gacttctacc ccaaagaggt caatgtcaag     120
tggaaagtgg atggcgtagt ccaaaacaaa ggcatccagg agagcaccac agagcagaac     180
agcaaggaca gcacctacag cctcagcagc accctgacga tgtccagtac ggagtaccaa     240
agtcatgaaa agttctcctg cgaggtcact cacaagagcc tggcctccac cctcgtcaag     300
agcttcaaca ggagcgagtg tcagagagag                                      330

<210> SEQ ID NO 79
<211> LENGTH: 106
<212> TYPE: PRT
<213> ORGANISM: Artificial
<220> FEATURE:
<223> OTHER INFORMATION: Caninized variable light chain mAb sequence,
      from Mus musculus and Canis

<400> SEQUENCE: 79

Asp Ile Val Met Thr Gln Thr Pro Leu Ser Leu Ser Val Ser Pro Gly
 1               5                  10                  15

Glu Pro Ala Ser Ile Ser Cys Arg Ala Ser Glu Ser Val Asp Asn Tyr
                20                  25                  30

Gly Ile Ser Phe Met His Trp Phe Gln Gln Lys Pro Gly Gln Ser Pro
            35                  40                  45

Gln Arg Leu Ile Tyr Arg Ala Ser Asn Leu Glu Ser Gly Val Pro Asp
 50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr
                100                 105

<210> SEQ ID NO 80
<211> LENGTH: 111
<212> TYPE: PRT
<213> ORGANISM: Artificial
<220> FEATURE:
<223> OTHER INFORMATION: Consensus sequence of caninized variable light
      chain mAb sequence, from Mus musculus and Canis

```
<400> SEQUENCE: 80

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Ile Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Glu Leu Lys
                100                 105                 110
```

INTERLEUKIN-31 MONOCLONAL ANTIBODY

CROSS-REFERENCE TO RELATED APPLICATIONS

This application claims the benefit of U.S. Provisional Application No. 61/510,268 filed Jul. 21, 2011, the contents of which are incorporated herein by reference in their entirety.

FIELD OF THE INVENTION

The present invention relates to the field of recombinant monoclonal antibodies and their uses in clinical and scientific procedures, including diagnostic procedures. The present invention also provides isolated anti-IL31 antibodies in the form of veterinary compositions useful for treating a pruritic condition or an allergic condition in dogs or cats.

BACKGROUND OF THE INVENTION

Atopic dermatitis has been defined by the American College of Veterinary Dermatology task force as "a genetically-predisposed inflammatory and pruritic allergic skin disease with characteristic clinical features" (Olivry, et al. Veterinary Immunology and Immunopathology 2001; 81: 143-146). The task force also recognized that the disease in canines has been associated with allergen-specific IgE (Olivry, et al. 2001 supra; Marsella & Olivry Clinics in Dermatology 2003; 21: 122-133). Severe pruritus, along with secondary alopecia and erythema, are the most noticeable and concerning symptoms to pet owners.

The prevalence of atopic dermatitis is not known with precision due to poor and inconsistent epidemiological data, but is estimated to be 10% of the total canine population (Marsella & Olivry 2003 supra; Scott, et al. Canadian Veterinary Journal 2002; 43: 601-603; Hillier Veterinary Immunology and Immunopathology 2001; 81: 147-151). Globally, about 4.5 million dogs are affected with this chronic and lifelong condition. Incidence appears to be increasing. Breed and sex predilections have been suspected, but may vary greatly depending on geographical region (Hillier, 2001 supra; Picco, et al. Vet Dermatol. 2008; 19: 150-155).

The potential factors involved in allergic dermatitis are numerous and poorly understood. Components in food may trigger atopic dermatitis (Picco, 2008 supra), as well as environmental allergens such as fleas, dust mites, ragweed, plant extracts, etc. Genetic factors also play an important role. Although there is no confirmed breed predilection, some mode of inheritance is thought to increase predisposition to atopic dermatitis (Sousa & Marsella Veterinary Immunology and Immunopathology 2001; 81: 153-157; Schwartzman, et al. Clin. Exp. Immunol. 1971; 9: 549-569.

Interleukin-31 (IL-31) is a cytokine that was cloned in 2004. It is mainly produced by activated T helper (Th)2 cells (Dillon et al. Nat Immunol 2004; 5:752-60), but is also produced in mast cells and macrophages. IL-31 binds a co-receptor composed of IL-31 receptor A (IL-31RA) and the oncostatin M receptor (OSMR) (Dillon et al. 2004 supra and Bilsborough et al. J Allergy Clin Immunol. 2006 117(2):418-25). Receptor activation results in phosphorylation of STAT through JAK receptor(s). Expression of the co-receptor has been shown in macrophages, keratinocytes and in dorsal root ganglia. Recently, it has been found that IL-31 is involved in dermatitis, pruritic skin lesions, allergy and airway hypersensitivity. See FIG. 1.

Stimulation of T cells with anti-CD3 and anti-CD28 antibodies immediately upregulates IL-31 mRNA expression (Dillon et al. 2004 supra). Microarray analysis has shown that IL-31 induces certain chemotactic genes, such as CXCL1, CLL17 (thymus and activation-regulated chemokine [TARC]), CCL19 (macrophage inflammatory protein [MIP] 3β), CCL22 (monocyte-derived chemokine [MDC], CCL23 (MIP3), and CCL4 (MIPβ) (Dillon et al. 2004 supra).

Transgenic mice that over-express IL-31 show skin inflammation, pruritis, severe dermatitis, and alopecia (Dillon et al. 2004 supra). Subcutaneous injection of IL-31 into mice triggers infiltration by the inflammatory cells, neutrophils, eosinophils, lymphocytes, and macrophages, and results in epidermal thickening and dermal acanthosis. In NC/Nga mice, with atopic dermatitis (AD) due to natural causes, IL-31 is overexpressed in skin lesions and correlates with pruritus (Takaoka et al. Eur J. Pharmacol. 2005; 516, 180-181; Takaoka et al. Exp. Dermatol. 2006; 15, 161-167). Also, in murine models, IL-31 has been shown to induce rapid onset pruritus (Raap et al. J Allergy Clin Immunol. 2008; 122(2): 421-3)

Further studies have indicated that IL-31 is associated with atopic-dermatitis-induced skin inflammation and pruritus in humans. In human AD patients, the expression of IL-31 mRNA is considerably higher in skin lesions than in non-lesional skin, and the expression in non-lesional skin is greater than that in normal skin from healthy patients (Sonkoly et al. J Allergy Clin Immunol 2006; 117:411-7). Another study has reported that CD45RO+ (memory) cutaneous lymphocyte antigen (CLA)-positive T cells in the skin of AD patients express IL-31 mRNA and protein (Bilsborough et al. 2006 supra). It has also been reported that IL-31 mRNA overexpression in the skin of patients or allergic contact dermatitis is correlated with IL-4 and IL-13 mRNA expression, but not with interferon (IFN)-γ mRNA expression (Neis et al. J. Allergy Clin. Immunol. 2006; 118, 930-937). Furthermore, IL-31 serum levels have been shown to be elevated in human patients with chronic spontaneous urticaria and even more so in patients with AD (Raap et al. Exp Dermatol. 2010; 19(5):464-6). Also, a correlation of the severity of AD with serum IL-31 levels has been observed in humans (Rapp et al. 2008 supra). IL-31 secretion has also been shown to be enhanced in mast cells following IgE cross-linking and as a response to Staphylococcal superantigen in atopic individuals. In addition, IL-31 has been shown to stimulate the production of several pro-inflammatory mediators including IL-6, IL-8, CXCL1, CC17 and multiple metalloproteinases in human colonic myofibroblasts (Yagi, et al. International Journal of Molecular Medicine 2007; 19(6): 941-946.

Type I hypersensitivity against environmental allergens is considered to be the main mechanism of canine AD, and the levels of Th2-mediated cytokines, such as IL-4 are increased in the skin lesions of dogs with AD (Nuttall, et al. Vet. Immunol. Immunopathol. 2002; 87, 379-384). Moreover, infiltration by inflammatory cells, lymphocytes and neutrophils, is an important mechanism underlying the aggravation of the skin lesions; the overexpression of chemotactic genes such as CCL17/TARC, CCR4, and CCL28/mucosae-associated epithelial chemokine (MEC) contributes to the aggravation of skin lesions in the dogs with AD (see, Maeda, et al. Vet. Immunol. Immunopathol. 2005; 103, 83-92; Maeda, et al. Vet. Immunol. Immunopathol. 2002b; 90, 145-154; and Maeda, et al. J. Vet. Med. Sci. 2008; 70, 51-55).

Recent evidence has suggested that IL-31 might be involved in promoting allergic inflammation and an airway epithelial response characteristic of allergic asthma (Chattopadhyay, et al. J Biol Chem 2007; 282:3014-26; and Wai, et al. Immunology, 2007; 122, 532-541).

These observations support the hypothesis that IL-31 plays a significant role in both pruritic and allergic conditions. It would be desirable to provide a therapeutic antibody against IL-31 useful for treating a pruritic condition and/or an allergic condition in dogs or cats.

SUMMARY OF THE INVENTION

In one embodiment, the present invention provides an isolated antibody that specifically binds to at least one of a canine IL-31 or a feline IL-31. In some embodiments, the antibody is a monoclonal antibody. In one embodiment, the monoclonal antibody is chimeric. In another embodiment, the antibody is caninized or felinized.

In some embodiments, the antibody reduces, inhibits, or neutralizes IL-31 activity in a dog or cat. In preferred embodiments, the antibody reduces, inhibits, or neutralizes a pruritic condition or an allergic condition. Pruritic conditions include, for example, atopic dermatitis, eczema, psoriasis, scleroderma, and pruritus.pruritus. Allergic conditions include, for example, allergic dermatitis, summer eczema, urticaria, heaves, inflammatory airway disease, recurrent airway obstruction, airway hyper-responsiveness, chronic obstructive pulmonary disease, and inflammatory processes resulting from autoimmunity, such as Irritable bowel syndrome (IBS).

In one embodiment, the present invention provides an isolated antibody or antigen-binding portion thereof including at least one of the following:
- a variable heavy ($V_H$) chain complementary determining region (CDR)1 having the amino acid sequence YYDIN (SEQ ID NO: 1; 11E12-VH-CDR1), SYDMS (SEQ ID NO: 2; 19D07-VH-CDR1), or NYGMS (SEQ ID NO: 3; 34D03-VH-CDR1);
- a variable heavy chain CDR2 having the amino acid sequence WIFPGDGGTKYNETFKG (SEQ ID NO: 4; 11E12-VH-CDR2), TITSGGGYTYSADSVKG (SEQ ID NO: 5; 19D07-VH-CDR2), or TISYGGSYTYYPD-NIKG (SEQ ID NO: 6; 34D03-VH-CDR2);
- a variable heavy chain CDR3 having the amino acid sequence ARGGTSVIRDAMDY (SEQ ID NO: 7; 11E12-VH-CDR3), ARQNWVVGLAY (SEQ ID NO: 8; 19D07-VH-CDR3), or VRGYGYDTMDY (SEQ ID NO: 9; 34D03-VH-CDR3); and
- a variant thereof having one or more conservative amino acid substitutions in at least one of CDR1, CDR2, or CDR3.

In another embodiment, the invention provides an isolated antibody or antigen-binding portion thereof including at least one of the following group:
- a variable light ($V_L$) chain comprising a complementary determining region (CDR) 1 having the amino acid sequence RASESVDNYGISFMH (SEQ ID NO: 10; 11E12-VL-CDR1), KSSQSLLNSGNQKNYLA (SEQ ID NO: 11; 19D07-VL-CDR1), or KASQSVSFAGT-GLMH (SEQ ID NO: 12; 34D03-VL-CDR1);
- a variable light chain CDR2 having the amino acid sequence RASNLES (SEQ ID NO: 13; 11E12-VL-CDR2), GASTRES (SEQ ID NO: 14; 19D07-VL-CDR2), or RASNLEA (SEQ ID NO: 15; 34D03-VL-CDR2);
- a variable light chain CDR3 having the amino acid sequence QQSNKDPLT (SEQ ID NO: 16; 11E12-VL-CDR3), QNDYSYPYT (SEQ ID NO: 17; 19D07-VL-CDR3), or QQSREYPWT (SEQ ID NO: 18; 34D03-VL-CDR3); and
- a variant thereof having one or more conservative amino acid substitutions in at least one of CDR1, CDR2, or CDR3.

In still other embodiments, an antibody having at least one of the variable light chain CDRs described above, can further include at least one of the following variable heavy chain CDRs:
- a variable heavy chain complementary determining region (CDR)1 having the amino acid sequence YYDIN (SEQ ID NO: 1; 11E12-VH-CDR1), SYDMS (SEQ ID NO: 2; 19D07-VH-CDR1), or NYGMS (SEQ ID NO: 3; 34D03-VH-CDR1);
- a variable heavy chain CDR2 having the amino acid sequence WIFPGDGGTKYNETFKG (SEQ ID NO: 4; 11E12-VH-CDR2), TITSGGGYTYSADSVKG (SEQ ID NO: 5; 19D07-VH-CDR2), or TISYGGSYTYYPD-NIKG (SEQ ID NO: 6; 34D03-VH-CDR2);
- a variable heavy chain CDR3 having the amino acid sequence ARGGTSVIRDAMDY (SEQ ID NO: 7; 11E12-VH-CDR3), ARQNWVVGLAY (SEQ ID NO: 8; 19D07-VH-CDR3), or VRGYGYDTMDY (SEQ ID NO: 9; 34D03-VH-CDR3); and
- a variant thereof having one or more conservative amino acid substitutions in at least one of CDR1, CDR2, or CDR3.

In some embodiments, the antibody can include at least one of the following:
a) a variable light chain comprising

```
                              (SEQ ID NO: 19; MU-11E12-VL)
DIVLTQSPASLAVSLGQRATISCRASESVDNYGISFMHWYQQKPGQPPK

LLIYRASNLESGIPARFSGSGSRTDFTLTINPVETDDVATYYCQQSNKDP

LTFGAGTKLELK, (SEQ ID NO: 20; CAN-11E12-VL-cUn-FW2)
DIVMTQTPLSLSVSPGEPASISCRASESVDNYGISFMHWYQQKPGQPPK

LLIYRASNLESGVPDRFSGSGSGTDFTLRISRVEADDAGVYYCQQSNKDP

LTFGAGTKLEIK, (SEQ ID NO: 21; CAN-11E12-VL-cUn-13)
DIVMTQTPLSLSVSPGEPASISCRASESVDNYGISFMHWFQQKPGQSPQL

LIYRASNLESGVPDRFSGSGSGTDFTLRISRVEADDAGVYYCQQSNKDPL

TFGAGTKLEIK, (SEQ ID NO: 22; MU-19D07-VL)
DIVMSQSPSSLSVSAGDKVTMSCKSSQSLLNSGNQKNYLAWYQQKPWQPP

KLLIYGASTRESGVPDRFTGSGSGTDFTLTISSVQAEDLAVYYCQNDYSY

PYTFGGGTKLEIK, (SEQ ID NO: 23; CAN-19D07-VL-998-1)
EIVMTQSPASLSLSQEEKVTITCKSSQSLLNSGNQKNYLAWYQQKPGQA

PKLLIYGASTRESGVPSRFSGSGSGTDFSFTISSLEPEDVAVYYCQNDYS

YPYTFGQGTKLEIK, (SEQ ID NO: 24; MU-34D03-VL)
DILLTQSPASLAVSLGQRAIISCKASQSVSFAGTGLMHWYQQKPGQQPKL

LIYRASNLEAGVPTRFSGSGSRTDFTLNIHPVEEEDAATYFCQQSREYPW

TFGGGTKLEIK,
or
                              (SEQ ID NO: 25; CAN-34D03-VL-998-1)
EIVMTQSPASLSLSQEEKVTITCKASQSVSFAGTGLMHWYQQKPGQAPKL

LIYRASNLEAGVPSRFSGSGSGTDFSFTISSLEPEDVAVYYCQQSREYPW

TFGQGTKLEIK;
``` b) a variable heavy chain comprising

```
                              (SEQ ID NO: 26; MU-11E12-VH)
QVQLQQSGAELVKPGASVKLSCKASGYTFKYYDINWVRQRPEQGLEWIGW

IFPGDGGTKYNETFKGKATLTTDKSSSTAYMQLSRLTSEDSAVYFCARGG

TSVIRDAMDYWGQGTSVIVSS, (SEQ ID NO: 27; CAN-11E12-VH-415-1)
EVQLVQSGAEVKKPGASVKVSCKTSGYTFKYYDINWVRQAPGAGLDWMGW

IFPGDGGTKYNETFKGRVTLTADTSTSTAYMELSSLRAGDIAVYYCARGG

TSVIRDAMDYWGQGTLVIVSS, (SEQ ID NO: 28; MU-19D07-VH)
EVKLVESGGGLVKPGGSLKLSCAASGFAFSSYDMSWVRQIPEKRLEWVAT

ITSGGGYTYSADSVKGRFTISRDNARNTLYLQMSSLRSEDTAVYYCARQN

WVVGLAYWGQGTLVTVSA, (SEQ ID NO: 29; CAN-19D07-VH-400-1)
EVQLVESGGDLVKPGGSLRLSCVASGFTFSSYDMSWVRQAPGKGLQWVAT

ITSGGGYTYSADSVKGRFTISRDNARNTLYLQMNSLRSEDTAVYYCARQN

WVVGLAYWGQGTLVTVSS, (SEQ ID NO: 30; MU-34D03-VH)
EVQLVESGGDLVKPGGSLKLSCAASGFSFSNYGMSWVRQTPDKRLEWVAT

ISYGGSYTYYPDNIKGRFTISRDNAKNTLYLQMSSLKSEDTAMYYCVRGY

GYDTMDYWGQGTSVTVSS,
or (SEQ ID NO: 31; CAN-34D03-VH-568-1)
EVQLVESGGDLVKPGGSLRLSCVASGFTFSNYGMSWVRQAPGKGLQWVAT

ISYGGSYTYYPDNIKGRFTISRDNAKNTLYLQMNSLRAEDTAMYYCVRGY

GYDTMDYWGQGTLVTVSS;
``` and
c) variants thereof having one or more conservative amino acid substitutions.

In one embodiment, the present invention provides a monoclonal antibody that specifically binds to a region between about amino acid residues 95 and 125 of the canine IL-31 amino acid sequence of SEQ ID NO: 32 or to a corresponding region in feline IL-31. In some embodiments, the antibody specifically binds to a region between about amino acid residues 102 and 122 of the canine IL-31 amino acid sequence of SEQ ID NO: 32 or to a corresponding region in feline IL-31.

The present invention also provides a veterinary composition including a therapeutically effective amount of at least one antibody described above.

In other embodiments, the invention provides a host cell that produces an antibody described above.

In still further embodiments, the invention provides an isolated nucleic acid including a nucleic acid sequence encoding at least one of the following:
  a variable heavy ($V_H$) chain complementary determining region (CDR)1 having the amino acid sequence YYDIN (SEQ ID NO: 1; 11E12-VH-CDR1), SYDMS (SEQ ID NO: 2; 19D07-VH-CDR1), or NYGMS (SEQ ID NO: 3; 34D03-VH-CDR1);
  a variable heavy chain CDR2 having the amino acid sequence WIFPGDGGTKYNETFKG (SEQ ID NO: 4; 11E12-VH-CDR2), TITSGGGYTYSADSVKG (SEQ ID NO: 5; 19D07-VH-CDR2), or TISYGGSYTYYPD-NIKG (SEQ ID NO: 6; 34D03-VH-CDR2);
  a variable heavy chain CDR3 having the amino acid sequence ARGGTSVIRDAMDY (SEQ ID NO: 7; 11E12-VH-CDR3), ARQNWVVGLAY (SEQ ID NO: 8; 19D07-VH-CDR3), or VRGYGYDTMDY (SEQ ID NO: 9; 34D03-VH-CDR3); and
  a variant thereof having one or more conservative amino acid substitutions in at least one of CDR1, CDR2, or CDR3.

In further embodiments, the isolated nucleic acid described above may further include a nucleic acid sequence encoding at least one of the following:
  a variable light ($V_L$) chain comprising a complementary determining (CDR) 1 having the amino acid sequence RASESVDNYGISFMH (SEQ ID NO: 10; 11E12-VL-CDR1), KSSQSLLNSGNQKNYLA (SEQ ID NO: 11; 19D07-VL-CDR1), or KASQSVSFAGTGLMH (SEQ ID NO: 12; 34D03-VL-CDR1);
  a variable light chain CDR2 having the amino acid sequence RASNLES (SEQ ID NO: 13; 11E12-VL-CDR2), GASTRES (SEQ ID NO 14; 19D07-VL-CDR2), or RASNLEA (SEQ ID NO: 15; 34D03-VL-CDR2);
  a variable light chain CDR3 having the amino acid sequence QQSNKDPLT (SEQ ID NO: 16; 11E12-VL-CDR3), QNDYSYPYT (SEQ ID NO: 17; 19D07-VL-CDR3), or QQSREYPWT (SEQ ID NO: 18; 34D03-VL-CDR3); and
  a variant thereof having one or more conservative amino acid substitutions in at least one of CDR1, CDR2, or CDR3.

The present invention further provides a vector including at least one of the nucleic acids described above.

In other embodiments, the present invention provides a method of producing an antibody comprising culturing a host cell described above under conditions that result in production of the antibody, and isolating the antibody from the host cell or culture medium of the host cell.

Also provided is a method of treating a condition or disorder selected from a pruritic condition or an allergic condition, including administering a therapeutically effective amount of an antibody described above. In some embodiments, the pruritic condition is selected from atopic dermatitis, eczema, psoriasis, scleroderma, and pruritus. In other embodiments, the allergic condition to be treated is selected from allergic dermatitis, summer eczema, urticaria, heaves, inflammatory airway disease, recurrent airway obstruction, airway hyperresponsiveness, chronic obstructive pulmonary disease, and inflammatory processes resulting from autoimmunity, such as Irritable bowel syndrome (IBS).

Further provided is a method of inhibiting IL-31 activity in a dog or cat by administering an antibody described above.

Also provided is a method of detecting or quantitating IL-31 in a sample, the method including incubating a clinical or biological sample containing IL-31 in the presence of an antibody described above; and detecting the antibody which is bound to IL-31 in the sample. In one embodiment, the antibody is detectably labeled. In another embodiment, the antibody is unlabeled and is used in combination with a second antibody which is labeled.

BRIEF DESCRIPTION OF THE DRAWINGS

FIG. 6 ELISA Titers from IL-31 Immunized Mice (CF-1 MU#1-4) relative to pre-bleed and positive control mice.

FIG. 7 is an illustration of antibody variable chains showing primers to constant regions and degenerate primers directed at mouse variable regions.

FIG. 8 is a graph of the pilot efficacy of chimeric 11E12 in a placebo controlled, single dose, SC study (76A60).

FIG. 9 is of a table showing the individual pruritic scores from dogs enrolled in study 76A60.

FIG. 23 is a Western blot of feline and canine IL-31 under reducing conditions probed with felinized antibody 34D03.

BRIEF DESCRIPTION OF THE SEQUENCES

Figure 1:
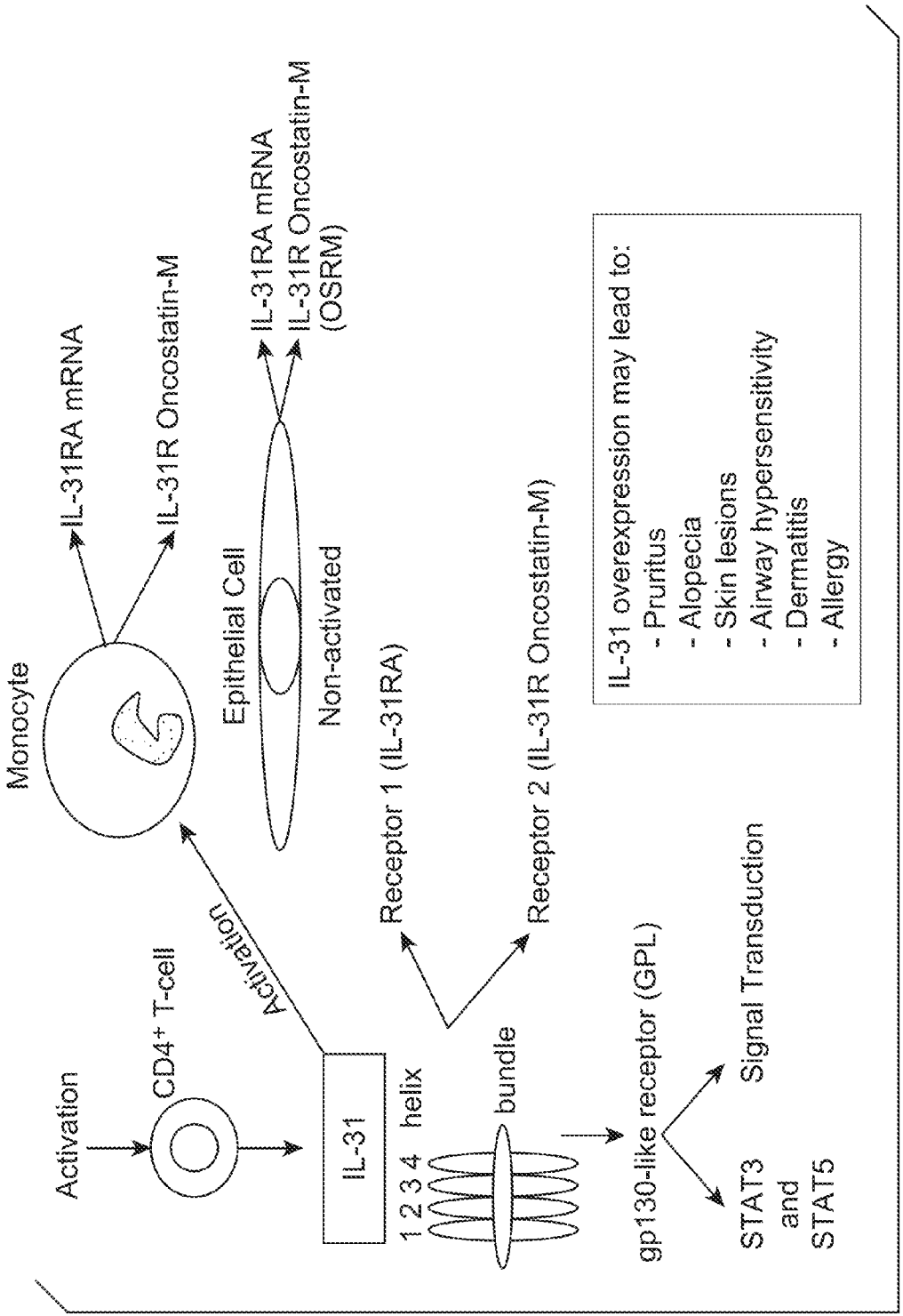
FIG. 1 is a schematic representation of the IL-31 pathway.
Figure 11:
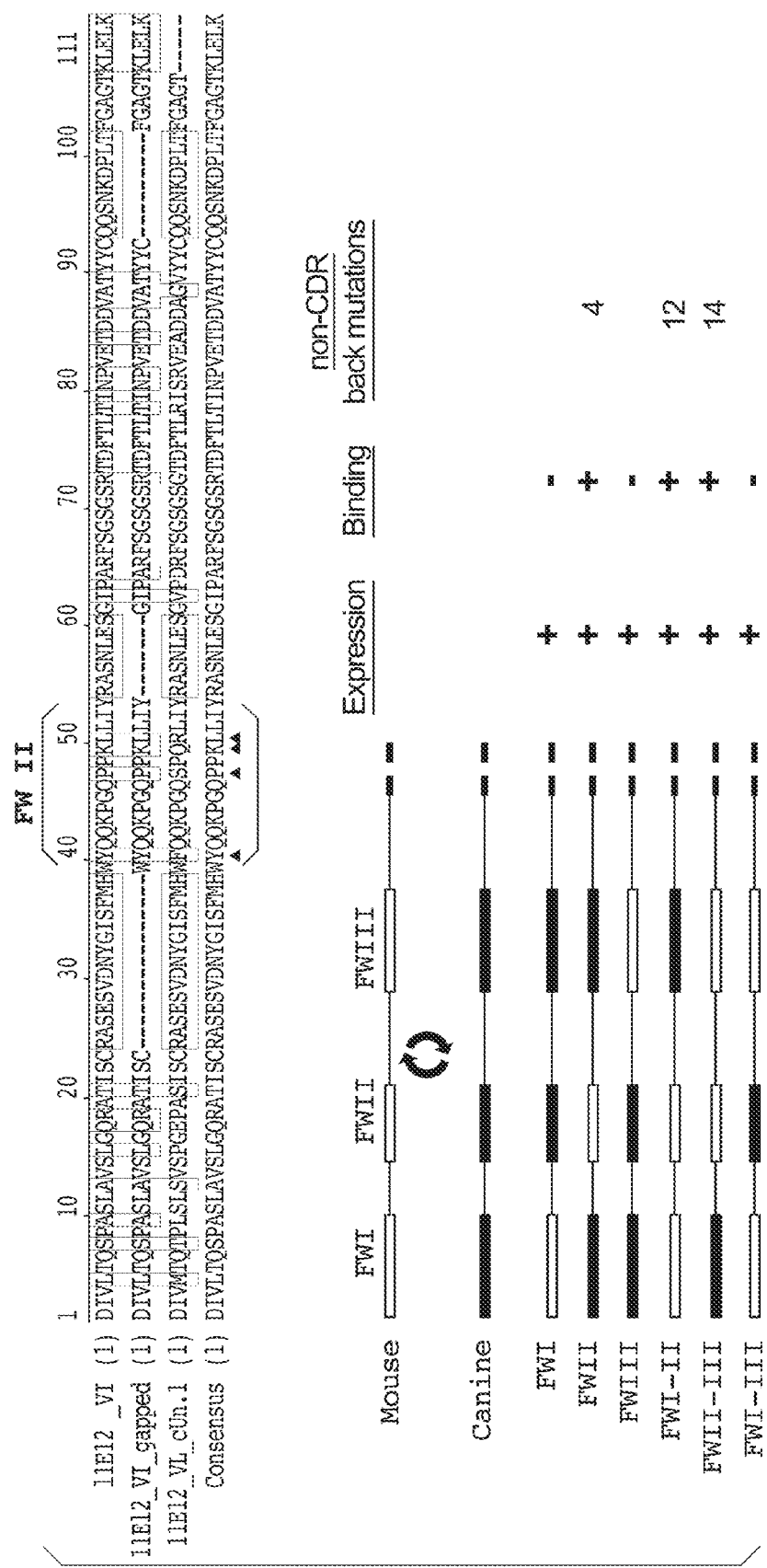
FIG. 11 is a schematic overview of canonized 11E12 light chain framework substitution work. The sequence designated as "11E12 VI" corresponds to SEQ ID NO: 19: the sequence designated as "11E12 VI gapped" corresponds to SEQ ID NO: 19 except that it is missing the CDR sequences corresponding to RASES (SEQ ID NO: 10), RASNLES (SEQ ID NO: 13) and QQSNKDPLT (SEQ ID NO: 16); the sequence designated as "11E12VL cUn.1" corresponds to SEQ ID NO: 79; and the sequence designated as "Consensus" corresponds to SEQ ID NO: 80.

SEQ ID NO: 1 is a variable heavy chain CDR1 referred to herein as 11E12-VH-CDR1;
SEQ ID NO: 2 is a variable heavy chain CDR1 referred to herein as 19D07-VH-CDR1;
SEQ ID NO: 3 is a variable heavy chain CDR1 referred to herein as 34D03-VH-CDR1;
SEQ ID NO: 4 is a variable heavy chain CDR2 referred to herein as 11E12-VH-CDR2;
SEQ ID NO: 5 is a variable heavy chain CDR2 referred to herein as 19D07-VH-CDR2;
SEQ ID NO: 6 is a variable heavy chain CDR2 referred to herein as 34D03-VH-CDR2;
SEQ ID NO: 7 is a variable heavy chain CDR3 referred to herein as 11E12-VH-CDR3;
SEQ ID NO: 8 is a variable heavy chain CDR3 referred to herein as 19D07-VH-CDR3;
SEQ ID NO: 9 is a variable heavy chain CDR3 referred to herein as 34D03-VH-CDR3;
SEQ ID NO: 10 is a variable light chain CDR1 referred to herein as 11E12-VL-CDR1;
SEQ ID NO: 11 is a variable light chain CDR1 referred to herein as 19D07-VL-CDR1;

SEQ ID NO: 12 is a variable light chain CDR1 referred to herein as 34D03-VL-CDR1;

SEQ ID NO: 13 is a variable light chain CDR2 referred to herein as 11E12-VL-CDR2;

SEQ ID NO: 14 is a variable light chain CDR2 referred to herein as 19D07-VL-CDR2;

SEQ ID NO: 15 is a variable light chain CDR2 referred to herein as 34D03-VL-CDR2;

SEQ ID NO: 16 is a variable light chain CDR2 referred to herein as 11E12-VL-CDR3;

SEQ ID NO: 17 is a variable light chain CDR3 referred to herein as 19D07-VL-CDR3;

SEQ ID NO: 18 is a variable light chain CDR3 referred to herein as 34D03-VL-CDR3;

SEQ ID NO: 19 is a variable light chain sequence referred to herein as MU-11E12-VL;

SEQ ID NO: 20 is a variable light chain sequence referred to herein as CAN-11E12-VL-cUn-FW2;

SEQ ID NO: 21 is a variable light chain sequence referred to herein as CAN-11E12-VL-cUn-13;

SEQ ID NO: 22 is a variable light chain sequence referred to herein as MU-19D07-VL;

SEQ ID NO: 23 is a variable light chain sequence referred to herein as CAN-19D07-VL-998-1;

SEQ ID NO: 24 is a variable light chain sequence referred to herein as MU-34D03-VL;

SEQ ID NO: 25 is a variable light chain sequence referred to herein as CAN-34D03-VL-998-1;

SEQ ID NO: 26 is a variable heavy chain sequence referred to herein as MU-11E12-VH;

SEQ ID NO: 27 is a variable heavy chain sequence referred to herein as CAN-11E12-VH-415-1;

SEQ ID NO: 28 is a variable heavy chain sequence referred to herein as MU-19D07-VH;

SEQ ID NO: 29 is a variable heavy chain sequence referred to herein as CAN-19D07-VH-400-1;

SEQ ID NO: 30 is a variable heavy chain sequence referred to herein as MU-34D03-VH;

SEQ ID NO: 31 is a variable heavy chain sequence referred to herein as CAN-34D03-VH-568-1;

SEQ ID NO: 32 is the amino acid sequence corresponding to GenBank Accession No. C7G0W1 and corresponds to Canine IL-31 full-length protein;

SEQ ID NO: 33 is the nucleotide sequence corresponding to GenBank Accession No. C7G0W1 and corresponds to the nucleotide sequence encoding Canine IL-31 full-length protein;

SEQ ID NO: 34 is the nucleotide sequence encoding the variable light chain sequence referred to herein as MU-11E12-VL;

SEQ ID NO: 35 is the nucleotide sequence encoding the variable heavy chain sequence referred to herein as MU-11E12-VH;

SEQ ID NO: 36 is the nucleotide sequence encoding the variable light chain sequence referred to herein as MU-19D07-VL;

SEQ ID NO: 37 is the nucleotide sequence encoding the variable heavy chain sequence referred to herein as MU-19D07-VH;

SEQ ID NO: 38 is the nucleotide sequence encoding the variable light chain sequence referred to herein as MU-34D03-VL;

SEQ ID NO: 39 is the nucleotide sequence encoding the variable heavy chain sequence referred to herein as MU-34D03-VH;

SEQ ID NO: 40 is the amino acid sequence for the canine heavy chain constant region referred to herein as HC-64 (GenBank accession no. AF354264);

SEQ ID NO: 41 is the nucleotide sequence encoding the canine heavy chain constant region referred to herein as HC-64 (GenBank accession no. AF354264);

SEQ ID NO: 42 is the amino acid sequence for the canine heavy chain constant region referred to herein as HC-65 (GenBank accession no. AF354265);

SEQ ID NO: 43 is the nucleotide sequence encoding the canine heavy chain constant region referred to herein as HC-65 (GenBank accession no. AF354265);

SEQ ID NO: 44 is the amino acid sequence for the canine light chain constant region referred to herein as kappa (GenBank Accession No. XP_532962);

SEQ ID NO: 45 is the nucleotide sequence encoding the canine light chain constant region referred to as kappa (GenBank Accession No. XP_532962);

SEQ ID NO: 46 is the nucleotide sequence encoding the variable light chain sequence referred to herein as CAN-19D07-VL-998-1;

SEQ ID NO: 47 is the nucleotide sequence encoding the variable heavy chain sequence referred to herein as CAN-19D07-VH-998-1;

SEQ ID NO: 48 is the nucleotide sequence encoding the variable light chain sequence referred to herein as CAN-34D03-VL-998-1;

SEQ ID NO: 49 is the nucleotide sequence encoding the variable heavy chain sequence referred to herein as CAN-34D03-VH-568-1;

SEQ ID NO: 50 is the nucleotide sequence encoding the variable light chain sequence referred to herein as CAN-11E12-VL-cUn-FW2;

SEQ ID NO: 51 is the nucleotide sequence encoding the variable heavy chain sequence referred to herein as CAN-11E12-VH-415-1;

SEQ ID NO: 52 is the nucleotide sequence encoding the variable light chain sequence referred to herein as CAN-11E12-VL-cUn-13;

SEQ ID NO: 53 is a variable light chain sequence referred to herein as CAN-11E12_VL_cUn_1;

SEQ ID NO: 54 is the nucleotide sequence encoding the variable light chain sequence referred to herein as CAN-11E12-VL-cUn-1;

SEQ ID NO: 55 corresponds to the amino acid sequence of the canine IL-31 full-length construct used herein for *E. coli* expression;

SEQ ID NO: 56 is the nucleotide sequence corresponding to the canine IL-31 full-length construct used herein for *E. coli* expression;

SEQ ID NO: 57 is the amino acid sequence of the canine IL-31 −20N construct for *E. coli* expression;

SEQ ID NO: 58 is the nucleotide sequence corresponding to the canine IL-31 −20N construct for *E. coli* expression;

SEQ ID NO: 59 is the amino acid sequence of the canine IL-31 −40N construct for *E. coli* expression;

SEQ ID NO: 60 is the nucleotide sequence corresponding to the canine IL-31 −40N construct for *E. coli* expression;

SEQ ID NO: 61 is the amino acid sequence of the canine IL-31 −60N construct for *E. coli* expression;

SEQ ID NO: 62 is the nucleotide sequence corresponding to the canine IL-31 −60N construct for *E. coli* expression;

SEQ ID NO: 63 is the amino acid sequence of the canine IL-31 20-122 construct for *E. coli* expression;

SEQ ID NO: 64 is the nucleotide sequence corresponding to the canine IL-31 20-122 construct for *E. coli* expression;

SEQ ID NO: 65 is the amino acid sequence of the canine IL-31 20-100 construct for *E. coli* expression;

SEQ ID NO: 66 is the nucleotide sequence corresponding to the canine IL-31 20-100 construct for *E. coli* expression;

SEQ ID NO: 67 is the is the amino acid sequence of the canine IL-31 20-80 construct for *E. coli* expression;

SEQ ID NO: 68 is the nucleotide sequence corresponding to the canine IL-31 20-80 construct for *E. coli* expression;

SEQ ID NO: 69 is the nucleotide sequence corresponding to the feline IL-31 full-length construct for *E. coli* expression;

SEQ ID NO: 70 is the amino acid sequence corresponding to the feline IL-31 full-length construct for *E. coli* expression;

SEQ ID NO: 71 is a variable light chain sequence referred to herein as FEL-34D03-VL-021-1;

SEQ ID NO: 72 is the nucleotide sequence encoding the variable light chain sequence referred to herein as FEL-34D03-VL-021-1;

SEQ ID NO: 73 is a variable heavy chain sequence referred to herein as FEL-34D03-VH-035-1;

SEQ ID NO: 74 is the nucleotide sequence encoding the variable heavy chain sequence referred to herein as FEL-34D03-VH-035-1;

SEQ ID NO: 75 is the amino acid sequence for the feline heavy chain constant region referred to herein as HC-A Feline (GenBank accession no. AB016710.1);

SEQ ID NO: 76 is the nucleotide sequence encoding the feline heavy chain constant region referred to herein as HC-A Feline (GenBank accession no. AB016710.1);

SEQ ID NO: 77 is the amino acid sequence for the feline light chain constant region referred to herein as LC-Kappa Feline (GenBank accession no. AF198257.1);

SEQ ID NO: 78 is the nucleotide sequence encoding the feline light chain constant region referred to herein as LC-Kappa Feline (GenBank accession no. AF198257.1);

SEQ ID NO: 79 is a variable light chain sequence referred to as 11E12 VL cUn.1 in FIG. 11.

SEQ ID NO: 80 is a variable light chain sequence referred to as Consensus in FIG. 11.

Definitions

Before describing the present invention in detail, several terms used in the context of the present invention will be defined. In addition to these terms, others are defined elsewhere in the specification, as necessary. Unless otherwise expressly defined herein, terms of art used in this specification will have their art-recognized meanings.

As used in the specification and claims, the singular form "a", "an" and "the" include plural references unless the context clearly dictates otherwise. For example, reference to "an antibody" includes a plurality of such antibodies.

As used herein, the term "comprising" is intended to mean that the compositions and methods include the recited elements, but not excluding others.

Epitope, as used herein, refers to the antigenic determinant recognized by the CDRs of the antibody. In other words, epitope refers to that portion of any molecule capable of being recognized by, and bound by, an antibody. Unless indicated otherwise, the term "epitope" as used herein, refers to the region of IL-31 to which an anti-IL-31 agent is reactive to.

An "antigen" is a molecule or a portion of a molecule capable of being bound by an antibody which is additionally capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics.

The term "specifically" in the context of antibody binding, refers to high avidity and/or high affinity binding of an antibody to a specific antigen, i.e., a polypeptide, or epitope. In many embodiments, the specific antigen is an antigen (or a fragment or subfraction of an antigen) used to immunize the animal host from which the antibody-producing cells were isolated. Antibody specifically binding an antigen is stronger than binding of the same antibody to other antigens. Antibodies which bind specifically to a polypeptide may be capable of binding other polypeptides at a weak, yet detectable level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_D$ of $10^{-7}$ M or less, e.g., $10^{-8}$ M or less (e.g., $10^{-9}$ M or less, $10^{-10}$ or less, $10^{-11}$ or less, $10^{-12}$ or less, or $10^{-13}$ or less, etc.).

As used herein, the term "antibody" refers to an intact immunoglobulin having two light and two heavy chains. Thus a single isolated antibody or fragment may be a polyclonal antibody, a monoclonal antibody, a synthetic antibody, a recombinant antibody, a chimeric antibody, a heterochimeric antibody, a caninized antibody, or a felinized antibody. The term "antibody" preferably refers to monoclonal antibodies and fragments thereof, and immunologic binding equivalents thereof that can bind to the IL-31 protein and fragments thereof. The term antibody is used both to refer to a homogeneous molecular, or a mixture such as a serum product made up of a plurality of different molecular entities.

Figure 2:
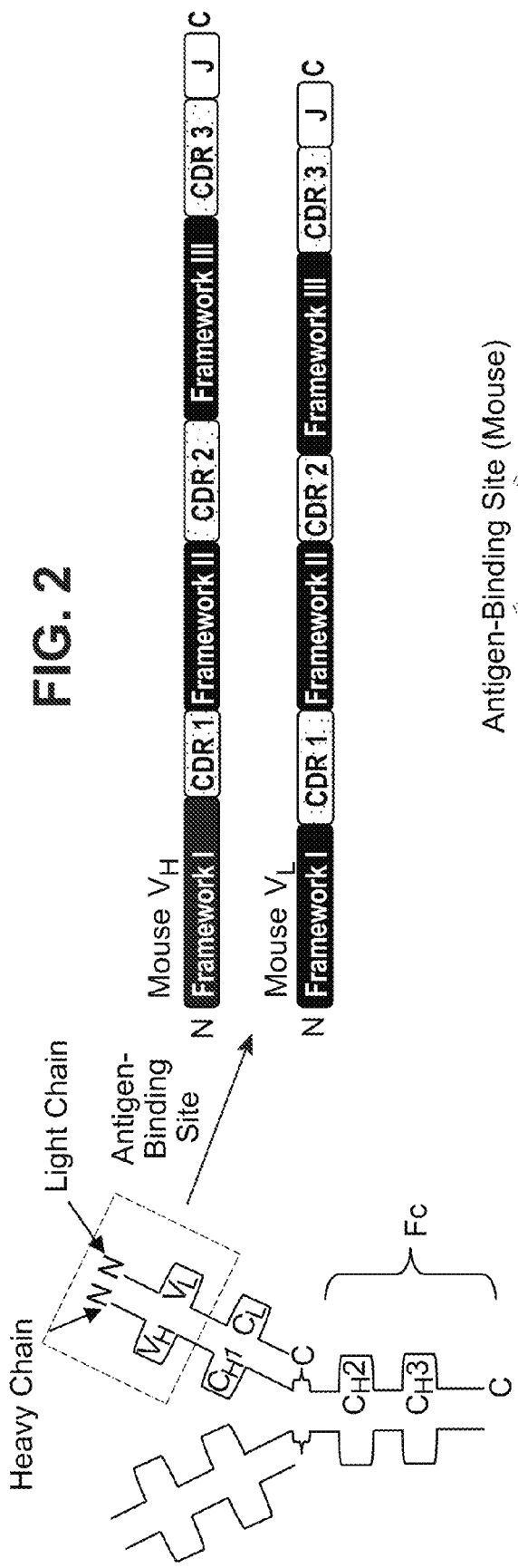
FIG. 2 is a schematic representation of the general structure of a mouse immunoglobulin G (IgG) molecule highlighting the antigen binding site.

"Native antibodies" and "native immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. FIG. 2 is an example of the general structure of a native mouse immunoglobulin G (IgG) highlighting the antigen binding site.

The term "antibody fragment" refers to less than an intact antibody structure, including, without limitation, an isolated single antibody chain, an Fv construct, a Fab construct, an Fc construct, a light chain variable or complementarity determining region (CDR) sequence, etc.

The term "variable" region comprises framework and CDRs (otherwise known as hypervariables) and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise multiple FRs, largely adopting a β-sheet configuration, connected by three hypervariable regions, which form loops connecting, and in some cases forming part of, the α-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (Kabat, et al. (1991), above) and/or those residues from a "hypervariable loop" (Chothia and Lesk J. Mol. Biol. 196:901-917 (1987). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Presently there are five major classes of immunoglobulins: IgA, IgD, IgE, IgG, and IgM, and several of these may be further divided into subclasses (isotypes), e.g., IgG1, IgG2, IgG3, IgG4, IgA, and IgA2 (as defined by mouse and human designation). The heavy-chain constant domains that correspond to the different classes of immunoglobulins are called alpha, delta, epsilon, gamma, and mu, respectively. The subunit structures and three-dimensional configurations of different classes of immunoglobulins are well known in multiple species. The prevalence of individual isotypes and functional activities associated with these constant domains are species-specific and must be experimentally defined.

"Monoclonal antibody" as defined herein is an antibody produced by a single clone of cells (specifically, a single clone of hybridoma cells) and therefore a single pure homogeneous type of antibody. All monoclonal antibodies produced from the same clone are identical and have the same antigen specificity. The term "monoclonal" pertains to a single clone of cells, a single cell, and the progeny of that cell.

Figure 3:
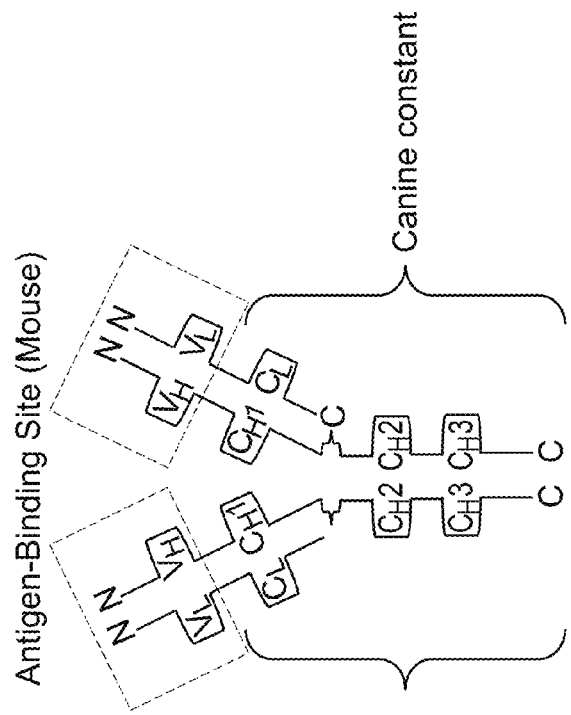
FIG. 3 is a schematic representation of the general structure of a mouse:canine chimeric IgG

The monoclonal antibodies herein specifically include "chimeric" antibodies (immunoglobulins) in which a portion of the heavy and/or light chain is identical with or homologous, to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to canine constant segments. FIG. 3 is a schematic representation of the general structure of one embodiment of a mouse:canine IgG. In this embodiment, the antigen binding site is derived from mouse while the $F_c$ portion is canine.

Figure 4:
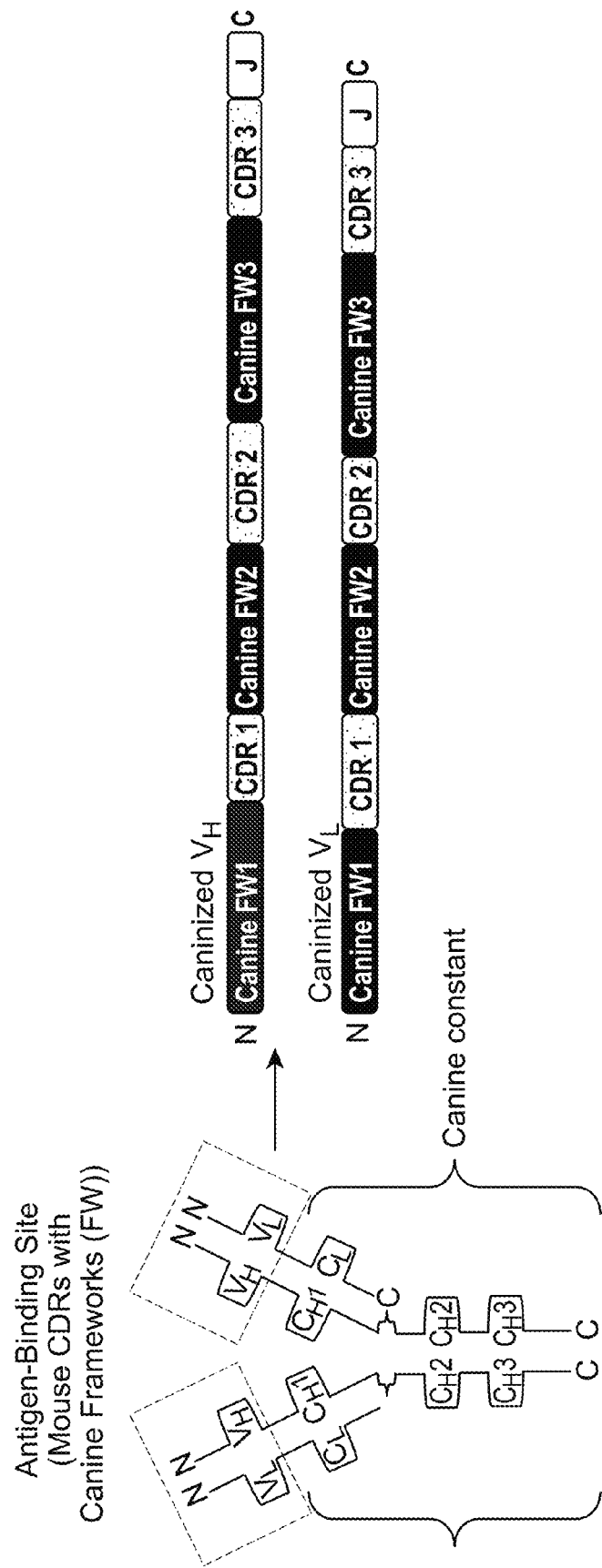
FIG. 4 is an illustration showing speciation or "caninization" of a mouse IgG, mouse CDRs are grafted onto canine frameworks identified from sequence databases

"Caninized" forms of non-canine (e.g., murine) antibodies are genetically engineered antibodies that contain minimal sequence derived from non-canine immunoglobulin. Caninized antibodies are canine immunoglobulin sequences (recipient antibody) in which hypervariable region residues of the recipient are replaced by hypervariable region residues from a non-canine species (donor antibody) such as mouse having the desired specificity, affinity, and capacity. In some instances, framework region (FR) residues of the canine immunoglobulin sequences are replaced by corresponding non-canine residues. Furthermore, caninized antibodies may include residues that are not found in the recipient antibody or in the donor antibody. These modifications are made to further refine antibody performance. In general, the caninized antibody will include substantially all of at least one, and typically two, variable domains, in which all or substantially all of the hypervariable regions correspond to those of a non-canine immunoglobulin sequence and all or substantially all of the FRs are those of a canine immunoglobulin sequence. The caninized antibody optionally also will comprise a complete, or at least a portion of an immunoglobulin constant region (Fc), typically that of a canine immunoglobulin sequence. FIG. 4 is an illustration of one embodiment showing speciation or caninization of a mouse IgG. In this embodiment, mouse CDRs are grafted onto canine frameworks.

"Felinized" forms of non-feline (e.g., murine) antibodies are genetically engineered antibodies that contain minimal sequence derived from non-feline immunoglobulin. Felinized antibodies are feline immunoglobulin sequences (recipient antibody) in which hypervariable region residues of the recipient are replaced by hypervariable region residues from a non-feline species (donor antibody) such as mouse having the desired specificity, affinity, and capacity. In some instances, framework region (FR) residues of the feline immunoglobulin sequences are replaced by corresponding non-feline residues. Furthermore, felinized antibodies may include residues that are not found in the recipient antibody or in the donor antibody. These modifications are made to further refine antibody performance. In general, the felinized antibody will include substantially all of at least one, and typically two, variable domains, in which all or substantially all of the hypervariable regions correspond to those of a non-feline immunoglobulin sequence and all or substantially all of the FRs are those of a feline immunoglobulin sequence. The felinized antibody optionally also will comprise a complete, or at least a portion of an immunoglobulin constant region (Fc), typically that of a feline immunoglobulin sequence.

Figure 5:
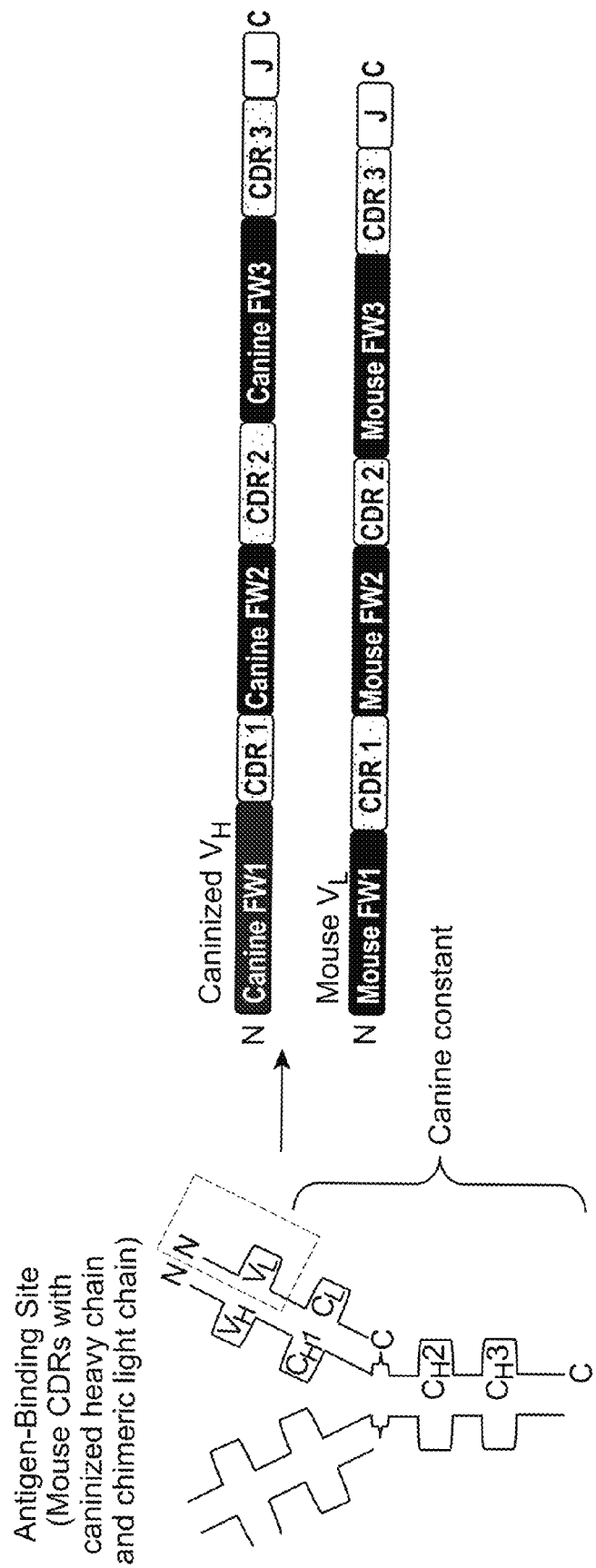
FIG. 5 is an illustration of a "heterochimeric" monoclonal antibody pairing the chimeric light chain with a fully caninized heavy chain.

The term "heterochimeric" as defined herein, refers to an antibody in which one of the antibody chains (heavy or light) is caninized while the other is chimeric. FIG. 5 depicts one embodiment of a heterochimeric molecule. In this embodiment, a caninized variable heavy chain (where all of the CDRs are mouse and all FRs are canine) is paired with a chimeric variable light chain (where all of the CDRs are mouse and all FRs are mouse. In this embodiment, both the variable heavy and variable light chains are fused to a canine constant region.

A "variant" anti-IL-31 antibody, refers herein to a molecule which differs in amino acid sequence from a "parent" anti-IL-31 antibody amino acid sequence by virtue of addition, deletion, and/or substitution of one or more amino acid residue(s) in the parent antibody sequence and retains at least one desired activity of the parent anti-IL-31-antibody. Desired activities can include the ability to bind the antigen specifically, the ability to reduce, inhibit or neutralize IL-31 activity in an animal, and the ability to inhibit IL-31-mediated pSTAT signaling in a cell-based assay. In one embodiment, the variant comprises one or more amino acid substitution(s) in one or more hypervariable and/or framework region(s) of the parent antibody. For example, the variant may comprise at least one, e.g. from about one to about ten, and preferably from about two to about five, substitutions in one or more hypervariable and/or framework regions of the parent antibody. Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind an IL-31 and preferably has desired activities which are superior to those of the parent antibody. For example, the variant may have a stronger binding affinity, enhanced ability to reduce, inhibit or neutralize IL-31 activity in an animal, and/or enhanced ability to inhibit IL-31-mediated pSTAT signaling in a cell-based assay.

A "variant" nucleic acid, refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The "parent" antibody herein is one that is encoded by an amino acid sequence used for the preparation of the variant. Preferably, the parent antibody has a canine framework region and, if present, has canine antibody constant region(s). For example, the parent antibody may be a caninized or canine antibody. As another example, the parent antibody may be a felinized or feline antibody. As yet another example, the parent antibody is a murine monoclonal antibody.

The term "isolated" means that the material (e.g., antibody or nucleic acid) is separated and/or recovered from a component of its natural environment. Contaminant components of its natural environment are materials that would interfere with diagnostic or therapeutic uses for the material, and may include enzymes, hormones, and other proteinaceous or non-proteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification step.

The word "label" when used herein refers to a detectable compound or composition that is conjugated directly or indirectly to the antibody or nucleic acid. The label may itself be detectable by itself (e.g., radioisotope labels or fluorescent labels) or, in the case of an enzymatic label, may catalyze chemical alteration of a substrate compound or composition that is detectable.

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (e.g., cDNA), an RNA molecule (e.g., mRNA), recombinant nucleic acids, plasmids, and other vectors, primers and probes. Both 5' to 3' (sense) and 3' to 5' (antisense) polynucleotides are included.

A "subject" or "patient" refers to an animal in need of treatment that can be affected by molecules of the invention. Animals that can be treated in accordance with the invention include vertebrates, with mammals such as canine, feline, and equine animals being particularly preferred examples.

A "therapeutically effective amount" (or "effective amount") refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated with treatment of a pruritic condition or an allergic condition including clinical improvement in symptoms. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art.

As used herein, the term "therapeutic" encompasses the full spectrum of treatments for a disease or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

"Treatment", "treating", and the like refers to both therapeutic treatment and prophylactic or preventative measures. Animals in need of treatment include those already with the disorder as well as those in which the disorder is to be prevented. The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "allergic condition" is defined herein as a disorder or disease caused by an interaction between the immune system and a substance foreign to the body. This foreign substance is termed "an allergen". Common allergens include aeroallergens, such as pollens, dust, molds, dust mite proteins, injected saliva from insect bites, etc. Examples of allergic conditions include, but are not limited to, the following: allergic dermatitis, summer eczema, urticaria, heaves, inflammatory airway disease, recurrent airway obstruction, airway hyper-responsiveness, chronic obstructive pulmonary disease, and inflammatory processes resulting from autoimmunity, such as Irritable bowel syndrome (IBS).

The term "pruritic condition" is defined herein as a disease or disorder characterized by an intense itching sensation that produces the urge to rub or scratch the skin to obtain relief. Examples of pruritic conditions include, but are not limited to the following: atopic dermatitis, eczema, psoriasis, scleroderma, and pruritus.

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

A "composition" is intended to mean a combination of active agent and another compound or composition which can be inert (e.g., a label), or active, such as an adjuvant.

As defined herein, pharmaceutically acceptable carriers suitable for use in the invention are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-HCl, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, 4.sup.th edit., eds. R. C. Rowe et al, APhA Publications, 2003.

The term "conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790, 639, 6,774,107, 6,194,167, or 5,350,576. In a preferred embodiment, a conservative amino acid substitution will be any one that occurs within one of the following six groups 1. Small aliphatic, substantially non-polar residues: Ala, Gly, Pro, Ser, and Thr;
2. Large aliphatic, non-polar residues: Ile, Leu, and Val; Met;
3. Polar, negatively charged residues and their amides: Asp and Glu;
4. Amides of polar, negatively charged residues: Asn and Gln; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gln; His); Asp (Glu); Gln (Asn); Glu (Asp); Gly (Pro); His (Asn; Gln); Ile (Leu; Val); Leu (Ile; Val); Lys (Arg; Gln; Glu); Met (Leu; Ile); Phe (Met; Leu; Tyr); Ser (Thr); Thr (Ser); Trp (Tyr); Tyr (Trp; Phe); and Val (Ile; Leu).

Just as a polypeptide may contain conservative amino acid substitution(s), a polynucleotide hereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

DETAILED DESCRIPTION OF THE INVENTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the antibodies described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transfection (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification, See e.g., Sambrook et al. MOLECULAR CLONING: LAB. MANUAL (3rd ed., Cold Spring Harbor Lab. Press, Cold Spring Harbor, N.Y., 2001) and Ausubel et al. Current Protocols in Molecular Biology (New York: Greene Publishing Association/Wiley Interscience), 1993. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

The present invention provides for recombinant monoclonal antibodies and peptides and their uses in clinical and scientific procedures, including diagnostic procedures.

With the advent of methods of molecular biology and recombinant technology, it is possible to produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as $H_2L_2$ and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues.

Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others.

In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope).

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The term "antibody" is meant to include both intact immunoglobulin molecules as well as portions, fragments, peptides and derivatives thereof such as, for example, Fab, Fab', F(ab')$_2$, Fv, Fse, CDR regions, paratopes, or any portion or peptide sequence of the antibody that is capable of binding an antigen or epitope. An antibody is said to be "capable of binding" a molecule if it is capable of specifically reacting with the molecule to thereby bind the molecule to the antibody.

Antibody also includes chimeric antibodies, heterochimeric antibodies, caninized antibodies, or felinized antibodies, as well as fragments, portions, regions, peptides or derivatives thereof, provided by any known technique, such as, but not limited to, enzymatic cleavage, peptide synthesis, or recombinant techniques. Such antibodies of the present invention are capable of specifically binding at least one of canine IL-31 or feline IL-31. Antibody fragments or portions may lack the Fc fragment of intact antibody, clear more rapidly from the circulation, and may have less non-specific tissue binding than an intact antibody. Examples of antibody fragments may be produced from intact antibodies using methods well known in the art, for example by proteolytic cleavage with enzymes such as papain (to produce Fab fragments) or pepsin (to produce F(ab')$_2$ fragments). See, e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

Clones 11E12, 34D03 and 19D07 Nucleotide and Amino Acid Sequences

In some embodiments, the present invention provides for novel monoclonal antibodies that specifically bind to at least one of canine IL-31 or feline IL-31. In one embodiment, a monoclonal antibody of the invention binds to canine IL-31 or feline IL-31 and prevents its binding to, and activation of, its co-receptor complex comprising IL-31 receptor A (IL-31 Ra) and Oncostatin-M-specific receptor (OsmR or IL-31 Rb). The monoclonal antibodies of the present invention are identified herein as "11E12", "34D03" and "19D07", which refers to the number assigned to its hybridoma clone. Herein, "11E12", "34D03", or "19D07" also refers to the portion of the monoclonal antibody, the paratope or CDRs, that bind specifically with an IL-31 epitope identified as 11E12, 34D03, or 19D07 because of its ability to bind the 11E12, 34D03, or 19D07 antibodies, respectively. The several recombinant, chimeric, heterochimeric, caninized and/or felinized forms of 11E12, 34D03 and 19D07 described herein may be referred to by the same name.

In one embodiment, the present invention provides an isolated antibody or antigen-binding portion thereof including at least one of the following:
  a variable heavy (V$_H$) chain complementary determining region (CDR)1 having the amino acid sequence YYDIN (SEQ ID NO: 1; 11E12-VH-CDR1), SYDMS (SEQ ID NO: 2; 19D07-VH-CDR1), or NYGMS (SEQ ID NO: 3; 34D03-VH-CDR1);
  a variable heavy chain CDR2 having the amino acid sequence WIFPGDGGTKYNETFKG (SEQ ID NO: 4; 11E12-VH-CDR2), TITSGGGYTYSADSVKG (SEQ ID NO: 5; 19D07-VH-CDR2), or TISYGGSYTYYPD-NIKG (SEQ ID NO: 6; 34D03-VH-CDR2);
  a variable heavy chain CDR3 having the amino acid sequence ARGGTSVIRDAMDY (SEQ ID NO: 7; 11E12-VH-CDR3), ARQNWVVGLAY (SEQ ID NO: 8; 19D07-VH-CDR3), or VRGYGYDTMDY (SEQ ID NO: 9; 34D03-VH-CDR3); and
  a variant thereof having one or more conservative amino acid substitutions in at least one of CDR1, CDR2, or CDR3.

In another embodiment, the invention provides an isolated antibody or antigen-binding portion thereof including at least one of the following group:
  a variable light (V$_L$) chain comprising a complementary determining region (CDR) 1 having the amino acid sequence RASESVDNYGISFMH (SEQ ID NO: 10; 11E12-VL-CDR1), KSSQSLLNSGNQKNYLA (SEQ ID NO: 11; 19D07-VL-CDR1), or KASQSVSFAGT-GLMH (SEQ ID NO: 12; 34D03-VL-CDR1);
  a variable light chain CDR2 having the amino acid sequence RASNLES (SEQ ID NO: 13; 11E12-VL-CDR2), GASTRES (SEQ ID NO: 14; 19D07-VL-CDR2), or RASNLEA (SEQ ID NO: 15; 34D03-VL-CDR2);
  a variable light chain CDR3 having the amino acid sequence QQSNKDPLT (SEQ ID NO: 16; 11E12-VL-CDR3), QNDYSYPYT (SEQ ID NO: 17; 19D07-VL-CDR3), or QQSREYPWT (SEQ ID NO: 18; 34D03-VL-CDR3); and
  a variant thereof having one or more conservative amino acid substitutions in at least one of CDR1, CDR2, or CDR3.

In still other embodiments, an antibody having at least one of the variable light chain CDRs described above, can further include at least one of the following variable heavy chain CDRs:
  a variable heavy chain complementary determining region (CDR)1 having the amino acid sequence YYDIN (SEQ ID NO: 1; 11E12-VH-CDR1), SYDMS (SEQ ID NO: 2; 19D07-VH-CDR1), or NYGMS (SEQ ID NO: 3; 34D03-VH-CDR1);
  a variable heavy chain CDR2 having the amino acid sequence WIFPGDGGTKYNETFKG (SEQ ID NO: 4; 11E12-VH-CDR2), TITSGGGYTYSADSVKG (SEQ ID NO: 5; 19D07-VH-CDR2), or TISYGGSYTYYPD-NIKG (SEQ ID NO: 6; 34D03-VH-CDR2);
  a variable heavy chain CDR3 having the amino acid sequence ARGGTSVIRDAMDY (SEQ ID NO: 7; 11E12-VH-CDR3), ARQNWVVGLAY (SEQ ID NO: 8; 19D07-VH-CDR3), or VRGYGYDTMDY (SEQ ID NO: 9; 34D03-VH-CDR3); and
  a variant thereof having one or more conservative amino acid substitutions in at least one of CDR1, CDR2, or CDR3.

In some embodiments, the antibody can include at least one of the following:
  a) a variable light chain comprising

```
                          (SEQ ID NO: 19; MU-11E12-VL)
DIVLTQSPASLAVSLGQRATISCRASESVDNYGISFMHWYQQKPGQPPKL

LIYRASNLESGIPARFSGSGSRTDFTLTINPVETDDVATYYCQQSNKDPL

TFGAGTKLELK, (SEQ ID NO: 20; CAN-11E12-VL-cUn-FW2)
DIVMTQTPLSLSVSPGEPASISCRASESVDNYGISFMHWYQQKPGQPPKL

LIYRASNLESGVPDRFSGSGSGTDFTLRISRVEADDAGVYYCQQSNKDPL

TFGAGTKLEIK, (SEQ ID NO: 21; CAN-11E12-VL-cUn-13)
DIVMTQTPLSLSVSPGEPASISCRASESVDNYGISFMHWFQQKPGQSPQL

LIYRASNLESGVPDRFSGSGSGTDFTLRISRVEADDAGVYYCQQSNKDPL

TFGAGTKLEIK, (SEQ ID NO: 22; MU-19D07-VL)
DIVMSQSPSSLSVSAGDKVTMSCKSSQSLLNSGNQKNYLAWYQQKPWQPP

KLLIYGASTRESGVPDRFTGSGSGTDFTLTISSVQAEDLAVYYCQNDYSY

PYTFGGGTKLEIK,
```

```
                    (SEQ ID NO: 23; CAN-19D07-VL-998-1)
EIVMTQSPASLSLSQEEKVTITCKSSQSLLNSGNQKNYLAWYQQKPGQAP

KLLIYGASTRESGVPSRFSGSGSGTDFSFTISSLEPEDVAVYYCQNDYSY

PYTFGQGTKLEIK, (SEQ ID NO: 24; MU-34D03-VL)
DILLTQSPASLAVSLGQRAIISCKASQSVSFAGTGLMHWYQQKPGQQPKL

LIYRASNLEAGVPTRFSGSGSRTDFTLNIHPVEEEDAATYFCQQSREYPW

TFGGGTKLEIK,
or
                    (SEQ ID NO: 25; CAN-34D03-VL-998-1)
EIVMTQSPASLSLSQEEKVTITCKASQSVSFAGTGLMHWYQQKPGQAPK

LLIYRASNLEAGVPSRFSGSGSGTDFSFTISSLEPEDVAVYYCQQSREYP

WTFGQGTKLEIK;
``` b) a variable heavy chain comprising

```
                             (SEQ ID NO: 26; MU-11E12-VH)
QVQLQQSGAELVKPGASVKLSCKASGYTFKYYDINWVRQRPEQGLEWIGW

IFPGDGGTKYNETFKGKATLTTDKSSSTAYMQLSRLTSEDSAVYFCARGG

TSVIRDAMDYWGQGTSVTVSS, (SEQ ID NO: 27; CAN-11E12-VH-415-1)
EVQLVQSGAEVKKPGASVKVSCKTSGYTFKYYDINWVRQAPGAGLDWMGW

IFPGDGGTKYNETFKGRVILTADTSTSTAYMELSSLRAGDIAVYYCARGG

TSVIRDAMDYWGQGTLVTVSS, (SEQ ID NO: 28; MU-19D07-VH)
EVKLVESGGGLVKPGGSLKLSCAASGFAFSSYDMSWVRQIPEKRLEWVAT

ITSGGGYTYSADSVKGRFTISRDNARNTLYLQMSSLRSEDTAVYYCARQN

WVVGLAYWGQGTLVTVSA, (SEQ ID NO: 29; CAN-19D07-VH-400-1)
EVQLVESGGDLVKPGGSLRLSCVASGFTFSSYDMSWVRQAPGKGLQWVAT

ITSGGGYTYSADSVKGRFTISRDNARNTLYLQMNSLRSEDTAVYYCARQN

WVVGLAYWGQGTLVTVSS, (SEQ ID NO: 30; MU-34D03-VH)
EVQLVESGGDLVKPGGSLKLSCAASGFSFSNYGMSWVRQTPDKRLEWVAT

ISYGGSYTYYPDNIKGRFTISRDNAKNTLYLQMSSLKSEDTAMYYCVRGY

GYDTMDYWGQGTSVTVSS,
or
                         (SEQ ID NO: 31; CAN-34D03-VH-568-1)
EVQLVESGGDLVKPGGSLRLSCVASGFTFSNYGMSWVRQAPGKGLQWVAT

ISYGGSYTYYPDNIKGRFTISRDNAKNTLYLQMNSLRAEDTAMYYCVRGY

GYDTMDYWGQGTLVTVSS;
``` and c) variants thereof having one or more conservative amino acid substitutions.

In other embodiments, the invention provides a host cell that produces an antibody described above.

The present invention also includes, within its scope, nucleotide sequences encoding the variable regions of the light and heavy chains of the anti-IL-31 antibody of the present invention. Included also within the scope of the invention is any nucleotide sequence that encodes the amino acid sequence of 11E12, 34D03 or 19D07 or peptides thereof.

In some embodiments, the invention provides an isolated nucleic acid including a nucleic acid sequence encoding at least one of the following:

a variable heavy ($V_H$) chain complementary determining region (CDR)1 having the amino acid sequence YYDIN (SEQ ID NO: 1; 11E12-VH-CDR1), SYDMS (SEQ ID NO: 2; 19D07-VH-CDR1), or NYGMS (SEQ ID NO: 3; 34D03-VH-CDR1);

a variable heavy chain CDR2 having the amino acid sequence WIFPGDGGTKYNETFKG (SEQ ID NO: 4; 11E12-VH-CDR2), TITSGGGYTYSADSVKG (SEQ ID NO: 5; 19D07-VH-CDR2), or TISYGGSYTYYPD-NIKG (SEQ ID NO: 6; 34D03-VH-CDR2);

a variable heavy chain CDR3 having the amino acid sequence ARGGTSVIRDAMDY (SEQ ID NO: 7; 11E12-VH-CDR3), ARQNWVVVGLAY (SEQ ID NO: 8; 19D07-VH-CDR3), or VRGYGYDTMDY (SEQ ID NO: 9; 34D03-VH-CDR3); and a variant thereof having one or more conservative amino acid substitutions in at least one of CDR1, CDR2, or CDR3.

In further embodiments, the isolated nucleic acid described above may further include a nucleic acid sequence encoding at least one of the following:

a variable light ($V_L$) chain comprising a complementary determining (CDR) 1 having the amino acid sequence RASESVDNYGISFMH (SEQ ID NO: 10; 11E12-VL-CDR1), KSSQSLLNSGNQKNYLA (SEQ ID NO: 11; 19D07-VL-CDR1), or KASQSVSFAGTGLMH (SEQ ID NO: 12; 34D03-VL-CDR1);

a variable light chain CDR2 having the amino acid sequence RASNLES (SEQ ID NO: 13; 11E12-VL-CDR2), GASTRES (SEQ ID NO: 14; 19D07-VL-CDR2), or RASNLEA (SEQ ID NO: 15; 34D03-VL-CDR2);

a variable light chain CDR3 having the amino acid sequence QQSNKDPLT (SEQ ID NO: 16; 11E12-VL-CDR3), QNDYSYPYT (SEQ ID NO: 17; 19D07-VL-CDR3), or QQSREYPWT (SEQ ID NO: 18; 34D03-VL-CDR3); and a variant thereof having one or more conservative amino acid substitutions in at least one of CDR1, CDR2, or CDR3.

The present invention further provides a vector including at least one of the nucleic acids described above.

Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-IL-31 antibody or portion. Such "codon usage rules" are disclosed by Lathe, et al., 183 J. Molec. Biol. 1-12 (1985). Using the "codon usage rules" of Lathe, a single nucleotide sequence, or a set of nucleotide sequences, that contains a theoretical "most probable" nucleotide sequence capable of encoding anti-IL-31 sequences can be identified. It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-IL-31 antibodies or peptides.

For example, one class of substitutions is conservative amino acid substitutions. Such substitutions are those that substitute a given amino acid in an anti-IL-31 antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant or agonist anti-IL-31 antibodies or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W.H. Freeman & Co., NY, 1993). Many detailed reviews are available on this subject, such as by Wold, Post-translational Covalent Modification of proteins, 1-12 (Johnson, ed., Academic Press, NY, 1983); Seifter et al. 182 Meth. Enzymol. 626-46 (1990); and Rattan et al. 663 Ann. NY Acad. Sci. 48-62 (1992).

Accordingly, the antibodies and peptides of the present invention also encompass derivatives or analogs in which a substituted amino acid residue is not one encoded by the genetic code.

Similarly, the additions and substitutions in the amino acid sequence as well as variations, and modifications just described may be equally applicable to the amino acid sequence of the IL-31 antigen and/or epitope or peptides thereof, and are thus encompassed by the present invention. As mentioned above, the genes encoding a monoclonal antibody according to the present invention is specifically effective in the recognition of IL-31.

Antibody Derivatives

Included within the scope of this invention are antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine ($^{125}$I,$^{131}$I) carbon ($^{14}$C), sulfur ($^{35}$S), indium ($^{111}$In), tritium ($^3$H) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegilation), and are well-known in the art. See U.S. Patent. Appl. Pub. No. 20030031671.

Recombinant Expression of Antibodies

In some embodiments, the nucleic acids encoding a subject monoclonal antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing.

Traditionally, monoclonal antibodies have been produced as native molecules in murine hybridoma lines. In addition to that technology, the present invention provides for recombinant DNA expression of monoclonal antibodies. This allows the production of caninized and felinized antibodies, as well as a spectrum of antibody derivatives and fusion proteins in a host species of choice.

A nucleic acid sequence encoding at least one anti-IL-31 antibody, portion or polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, NY, 1982 and 1989), and Ausubel et al. 1993 supra, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-IL-31 peptides or antibody portions in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an anti-IL-31 antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

In one embodiment, the introduced nucleotide sequence will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli* (such as, for example, pBR322, ColE1, pSC101, pACYC184, .pi.VX). Such plasmids are, for example, disclosed by Maniatis et al., 1989 supra; Ausubel et al, 1993 supra. *Bacillus* plasmids include pC194, pC221, pT127, etc. Such plasmids are disclosed by Gryczan, in THE MOLEC. BIO. OF THE BACILLI 307-329 (Academic Press, NY, 1982). Suitable *Streptomyces* plasmids include pIJ101 (Kendall et al., 169 J. Bacteriol. 4177-83 (1987)), and *Streptomyces* bacteriophages such as .phi.C31 (Chater et al., in SIXTH INT'L SYMPOSIUM ON ACTINOMYCETALES BIO. 45-54 (Akademiai Kaido, Budapest, Hungary 1986). *Pseudomonas* plasmids are reviewed in John et al., 8 Rev. Infect. Dis. 693-704 (1986); Izaki, 33 Jpn. J. Bacteriol. 729-42 (1978); and Ausubel et al., 1993 supra.

Alternatively, gene expression elements useful for the expression of cDNA encoding anti-IL-31 antibodies or peptides include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 Proc. Natl. Acad. Sci., USA 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with an anti-IL-31 peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-IL-31 peptide or chimeric H and L chains, or portions thereof are assembled in separate expression vectors that are then used to co-transfect a recipient cell. Alternatively the fused genes encoding the chimeric H and L chains can be assembled on the same expression vector.

For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric, caninized or felinized antibody construct or anti-IL-31 polypeptide of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988).

Yeast can provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of anti-IL-31 peptides, antibody and assembled murine and chimeric, heterochimeric, caninized, or felinized antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.) IRL Press, Oxford, UK 1985).

Bacterial strains can also be utilized as hosts for the production of antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine, chimeric, heterochimeric, caninized or felinized antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, N.Y. (1994-2001); Colligan et al., eds. Current Protocols in Protein Science, John Wiley & Sons, NY, N.Y. (1997-2001).

Host mammalian cells may be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells.

Many vector systems are available for the expression of cloned anti-IL-31 peptides H and L chain genes in mammalian cells (see Glover, 1985 supra). Different approaches can be followed to obtain complete $H_2L_2$ antibodies. It is possible to co-express H and L chains in the same cells to achieve intracellular association and linkage of H and L chains into complete tetrameric $H_2L_2$ antibodies and/or anti-IL-31 peptides. The co-expression can occur by using either the same or different plasmids in the same host. Genes for both H and L chains and/or anti-IL-31 peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-IL-31 peptides and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical Applications

The anti-IL-31 antibodies or peptides of the present invention can be used for example in the treatment of pruritic and/or allergic conditions in companion animals, such as dogs and cats. More specifically, the invention further provides for a pharmaceutical composition comprising a pharmaceutically acceptable carrier or diluent and, as active ingredient, an antibody or peptide according to the invention. The antibody can be a chimeric, heterochimeric, caninized, or felinized antibody according to the present invention. Intact immunoglobulins or their binding fragments, such as Fab, are also envisioned. The antibody and pharmaceutical compositions thereof of this invention are useful for parenteral administration, e.g., subcutaneously, intramuscularly or intravenously.

Anti-IL-31 antibodies and/or peptides of the present invention can be administered either as individual therapeutic agents or in combination with other therapeutic agents. They can be administered alone, but are generally administered with a pharmaceutical carrier selected on the basis of the chosen route of administration and standard pharmaceutical practice.

Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (e.g., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be, for example, in the form of an ingestable liquid or solid formulation.

In some desired embodiments, the antibodies are administered by parenteral injection. For parenteral administration, anti-IL-31 antibodies or peptides can be formulated as a solution, suspension, emulsion or lyophilized powder in association with a pharmaceutically acceptable parenteral vehicle. For example the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques.

Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

The compositions containing the present antibodies or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art.

In therapeutic application, compositions are administered to a subject already suffering from a disease, in an amount sufficient to cure or at least partially arrest or alleviate the disease and its complications. An amount adequate to accomplish this is defined as a "therapeutically effective dose" or a "therapeutically effective amount". Amounts effective for this use will depend upon the severity of the disease and the general state of the subject's own immune system, but generally range from about 0.1 mg antibody per kg body weight to about 10 mg antibody per kg body weight, preferably about 0.3 mg antibody per kg of body weight to about 5 mg of antibody per kg of body weight. In view of the minimization of extraneous substances and the lower probability of "foreign substance" rejections which are achieved by the present canine-like and feline-like antibodies of this invention, it may be possible to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of IL-31-related pathologies in dogs or cats can be provided as a biweekly or monthly dosage of anti-IL-31 antibodies of the present invention in the dosage range described above.

Example antibodies for canine or feline therapeutic use are high affinity (these may also be high avidity) antibodies, and fragments, regions and derivatives thereof having potent in vivo anti-IL-31 activity, according to the present invention.

Single or multiple administrations of the compositions can be carried out with dose levels and pattern being selected by the treating veterinarian. In any event, the pharmaceutical formulations should provide a quantity of the antibody(ies) of this invention sufficient to effectively treat the subject.

Diagnostic Applications

The present invention also provides the above anti-IL-31 antibodies and peptides for use in diagnostic methods for detecting IL-31 in companion animals known to be or suspected of having a puritic and/or allergic condition.

Anti-IL-31 antibodies and/or peptides of the present invention are useful for immunoassays which detect or quantitate IL-31, or anti-IL-31 antibodies, in a sample. An immunoassay for IL-31 typically comprises incubating a clinical or biological sample in the presence of a detectably labeled high affinity (or high avidity) anti-IL-31 antibody or polypeptide of the present invention capable of selectively binding to IL-31, and detecting the labeled peptide or antibody which is bound in a sample. Various clinical assay procedures are well known in the art. See, e.g., IMMUNOASSAYS FOR THE 80'S (Voller et al., eds., Univ. Park, 1981). Such samples include tissue biopsy, blood, serum, and fecal samples, or liquids collected from animal subjects and subjected to ELISA analysis as described below.

In some embodiments, the binding of antigen to antibody is detected without the use of a solid support. For example, the binding of antigen to antibody can be detected in a liquid format.

In other embodiments, an anti-IL-31 antibody or polypeptide can, for example, be fixed to nitrocellulose, or another solid support which is capable of immobilizing cells, cell particles or soluble proteins. The support can then be washed with suitable buffers followed by treatment with the detectably labeled IL-31-specific peptide or antibody. The solid phase support can then be washed with the buffer a second time to remove unbound peptide or antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to IL-31 or an anti-IL-31 antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation.

Well known method steps can determine binding activity of a given lot of anti-IL-31 peptide and/or antibody. Those skilled in the art can determine operative and optimal assay conditions by routine experimentation.

Detectably labeling an IL-31-specific peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the IL-31-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the IL-31-specific antibodies, it is possible to detect IL-31 through the use of a radioimmunoassay (RIA). See Work et al., LAB. TECHNIQUES & BIOCHEM. 1N MOLEC. Bio. (No. Holland Pub. Co., NY, 1978). The radioactive isotope can be detected by such means as the use of a gamma counter or a scintillation counter or by autoradiography. Isotopes which are particularly useful for the purpose of the present invention include: $^{3}H$, $^{125}I$, $^{131}I$, $^{35}S$, $^{14}C$, and $^{125}I$.

It is also possible to label the IL-31-specific antibodies with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The IL-31-specific antibodies can also be delectably labeled using fluorescence-emitting metals such a $^{125}Eu$, or others of the lanthanide series. These metals can be attached to the IL-31-specific antibody using such metal chelating groups as diethylenetriaminepentaacetic acid (DTPA) or ethylenediamine-tetraacetic acid (EDTA).

The IL-31-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the IL-31-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the IL-31-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the IL-31 which is detected by the above assays can be present in a biological sample. Any sample containing IL-31 may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject, and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of IL-31 but also the distribution of IL-31 in the examined tissue. Using the present invention, those of ordinary skill will readily perceive that any of a wide variety of histological methods (such as staining techniques) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid-phase antibody, antigen, and labeled antibody.

The antibodies may be used to quantitatively or qualitatively detect the IL-31 in a sample or to detect presence of cells that express the IL-31. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the antibody, such as antibodies specific for canine or feline immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art.

In one embodiment, the diagnostic method for detecting IL-31 is a lateral flow immunoassay test. This is also known as the immunochromatographic assay, Rapid ImmunoMigration (RIM™) or strip test. Lateral flow immunoassays are essentially immunoassays adapted to operate along a single axis to suit the test strip format. A number of variations of the technology have been developed into commercial products, but they all operate according to the same basic principle. A typical test strip consists of the following components: (1) sample pad—an absorbent pad onto which the test sample is applied; (2) conjugate or reagent pad—this contains antibodies specific to the target analyte conjugated to colored particles (usually colloidal gold particles, or latex microspheres); (3) reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies); and (4) wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones.

There are two main types of lateral flow immunoassay used in microbiological testing: double antibody sandwich assays and competitive assays. In the double antibody sandwich format, the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Competitive assays differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed.

Importantly, the antibodies of the present invention may be helpful in diagnosing a pruritic and/or allergic in dogs or cats. More specifically, the antibody of the present invention may identify the overexpression of IL-31 in companion animals. Thus, the antibody of the present invention may provide an important immunohistochemistry tool.

The antibodies of the present invention may be used on antibody arrays, highly suitable for measuring gene expression profiles.

Kits

Also included within the scope of the present invention are kits for practicing the subject methods. The kits at least include one or more of the antibodies of the present invention, a nucleic acid encoding the same, or a cell containing the same. In one embodiment, an antibody of the present invention may be provided, usually in a lyophilized form, in a container. The antibodies, which may be conjugated to a label or toxin, or unconjugated, are typically included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

In one embodiment, a kit according to the present invention is a test strip kit (lateral flow immunoassay kit) useful for detecting canine or feline IL-31 protein in a sample. Such a test strip will typically include a sample pad onto which the test sample is applied; a conjugate or reagent pad containing an antibody specific to canine or feline IL-31, wherein the antibody is conjugated to colored particles (usually colloidal gold particles); a reaction membrane onto which anti-IL-31 antibodies are immobilized in a line across the membrane as a capture zone or test line (a control zone may also be present, containing antibodies specific for the conjugate antibodies); and a further absorbent pad designed to draw the sample across the reaction membrane by capillary action and collect it. The test strip kit will generally also include directions for use.

The invention will now be described further by the non-limiting examples below.

EXAMPLES

Example 1

Identification of Mouse Monoclonal Antibodies Recognizing Canine Interleukin 31 (IL-31)

Recombinant canine IL-31 was created in CHO cells using the CHROMOS ACE (Artificial Chromosome Expression) system (Chromos Molecular Systems, Inc., Burnaby, British Columbia) to generate the secreted canine IL-31 protein having the sequence of SEQ ID NO: 32. This protein is encoded by the nucleotide sequence of SEQ ID NO: 33. Conditioned medium from 400 ml of cell culture (CHO cell line) was obtained and dialyzed against 10 volumes of QA buffer (20 mM Tris pH 8.0, 20 mM NaCl) for 4.5 hours. Dialyzed medium was 0.2 um filtered and loaded at 1 ml/min onto a SOURCE™ Q column (GE Healthcare, Uppsala, Sweden) pre-equilibrated with QA buffer. Protein was eluted using a multi step linear gradient. The majority of IL-31 remained in the flow through (FT) fraction, a small amount of IL-31 eluted early in the gradient. Identity of the protein was previously confirmed by Western immunoblotting, and Mass-Spectro (MS) analysis of a tryptic digest. Protein in the FT fraction was concentrated 4-5 fold and dialyzed overnight against Phosphate Buffered Saline (PBS) at 4° C. Stability of the protein was checked following dialysis into PBS. No precipitation was observed, and no proteolysis was observed after several days at 4° C. De-glycosylation experiments using N-glycosidase F resulted in the protein condensing down to a single band of ~15 kDa on SDS-PAGE. Protein concentration was determined using a bicinchoninic assay (BCA assay) with Bovine Serum Albumin (BSA) as a standard (ThermoFisher Scientific, Inc., Rockford, Ill.). The protein solution was split into aliquots, snap frozen (liquid $N_2$) and stored at −80° C.

Mouse monoclonal antibodies were identified using standard immunizations of female CF-1 mice with recombinant canine IL-31 produced in CHO cells. Titers from immunized mice were determined using an enzyme linked immunosorbent assay (ELISA). Canine IL-31 (50 ng/well) was immobilized to polystyrene microplates and used as a capture antigen. Serum from immunized mice was diluted in phosphate buffered saline with 0.05% tween-20 (PBST). The presence of mouse anti-canine IL-31 antibodies was detected with a Horse Radish Peroxidase (HRP)-conjugated goat anti-mouse secondary antibody (Kirkegard & Perry Laboratories, Inc. (KPL, Inc.), Gaithersburg, Md.). Following addition of a chromogenic substrate (SureBlue Reserve TMB 1-Component Microwell Peroxidase Substrate, KPL, Inc., Gaithersburg, Md.) and a ten minute incubation at room temperature (RT) the reaction was stopped with the addition of 100 μL of 0.1 N HCl. The absorbance of each well was determined at an optical density (OD) of 450 nm. FIG. 6 summarizes the antibody response of individual mice immunized with canine IL-31. A pool of donor splenocytes from mice 3 and 4 were used for fusion. Following fusion and screening for anti IL-31 binding via direct ELISA, 100 wells were chosen for expansion and secondary screening of anti IL-31 activity. Secondary screening confirmed that 81 fusions retained the ability to produce anti IL-31 antibodies. Frozen cell stocks and supernatants from these 81 candidates were preserved for further evaluation.

To identify candidates with inhibitory activity, all 81 supernatants were assessed for their ability to affect IL-31-mediated pSTAT signaling in a cell-based assay. This cell-based assay measures pSTAT signaling in canine DH-82 monocyte cells pre-treated for 24 hours with canine gamma interferon (R&D Systems, Minneapolis, Minn.) at 10 ng/mL and serum starved for 2 hours prior to IL-31 treatment to increase IL-31 receptor expression. Following this pre-treatment, recombinant canine IL-31 is added at 1 μg/mL for 5 minutes and STAT phosphorylation is evaluated using the Alpha Screen technology (Perkin Elmer, Waltham, Mass.). Since antibody concentrations and purity are unknown in hybridoma supernatants, these supernatants were qualitatively measured for their ability to inhibit STAT phosphorylation following a 1 hour co-incubation with 1 μg/ml IL-31 using 1:2 or 1:20 dilutions of the supernatants. This experiment identified 31 supernatants that inhibited >50% of the STAT phosphorylation relative to untreated wells thereby justifying purification and further characterization.

Following purification and quantitation of each monoclonal antibody (mAb), the $IC_{50}$ values of all 31 antibodies were evaluated in the DH-82 cell assay. Based on the resulting $IC_{50}$ values and competitive ELISAs to define antibody classes based on epitope bins, three antibodies described in Table 1 were moved forward for further characterization, 11E12, 19D07, and 34D03.

TABLE 1

| Antibody | HC isotype | LC isotype |
|---|---|---|
| 11E12 | G1/2b | kappa |
| 19D07 | 2b | kappa |
| 34D03 | G1 | kappa |

Example 2

DNA Sequences Encoding 11E12, 19D07 and 34D03 Antibodies

Ribonucleic acid (RNA) was isolated from hybridoma cells 11E12, 19D07, and 34D03 using the Rneasy—mini kit (Qiagen, Inc., Germantown, Md.) as described by the manufacturer. One million frozen cells from each hybridoma were harvested by centrifugation and RNA was purified from cell lysates using the Rneasy spin column according to method described in the protocol. RNA was eluted from each column and used immediately for quantitation and cDNA preparation. The RNA was analyzed for yield and purity by measuring it's absorbance at 260 nm and 280 nm using a GeneQuant pro spectrophotometer (GE Healthcare, Uppsala, Sweden). Following isolation, the remaining RNA was stored at −80° C. for further use.

Oligonucletide primers designed for amplification of the mouse immunoglobulin (Ig) variable domains were used according to the manufacturer's instructions (EMD Chemicals, Inc., Gibbstown, N.J.). cDNA was prepared from total hybridoma RNA by reverse transcription (RD) using the thermoscript RT kit (Invitrogen Corp., Carlsbad, Calif.) according to the manufacturers instructions. 200-400 ng of RNA from each hybridoma was added to an individual reaction tube containing a 3' Ig constant region primer. The 3' constant Ig primer is positioned proximal to the variable Ig region and will transcribe first strand cDNA representing the variable region of the mouse antibody. For each hybridoma RNA, an individual RT reaction was performed using a 3' constant heavy chain and 3' constant kappa light chain primer.

cDNA from each hybridoma were used as a template in a polymerase chain reaction (PCR) to amplify the variable IgG heavy and kappa light chain cDNA for the purpose of sequence determination. Multiple reactions were performed for each PCR using a degenerate 5' primer or primer pools designed to anneal to the signal sequence-coding regions of the mouse Ig variable domain. Separate PCR reactions were performed with a degenerate primer or primer pools for amplification of murine variable heavy and variable light chain regions (FIG. 7). PCR was performed with 1 μl of the cDNA reaction using the Expand High Fidelity DNA polymerase kit (Roche Diagnostics Corp., Indianapolis, Ind.) according to the manufacturers protocol. Thermocycling parameters for the PCR were as follows; 94° C. for 2 min., 35 cycles (94° C. 15 sec., 55° C. 30 sec., 72° C. 1 min.), 72° C. 7 min. Fragments amplified from the PCR were separated by gel electrophoresis on a 1% agarose gel and purified using Qiagen gel extraction kit (Qiagen, Inc., Germantown, Md.).

Forward primers for the heavy and light chain variable region incorporate EcoRI or SalI (New England Biolabs (NEB), Inc., Ipswich, Mass.) sites and reverse heavy and light chain variable, HindIII (NEB Inc., Ipswich, Mass.) to facilitate cloning into the pUC19 plasmid. Purified PCR fragments and pUC19 plasmid were digested with the above, restriction endonucleases at 37° C. for 1-2 hrs. Following digestion, PCR fragments were purified using a Qiaquick PCR cleanup kit (Qiagen, Inc., Germantown, Md.). Digested plasmid was separated by gel electrophoresis on a 1% agarose gel and purified using Qiagen gel extraction kit. Purified PCR fragments representing variable IgG heavy and kappa light chain DNA were ligated into pUC19 plasmid using T4 DNA ligase and ligation buffer (NEB, Inc., Ipswich, Mass.) at 4° C. overnight. 3 µl of each ligation reaction was used to transform *E. coli* TOP10 cells (Invitrogen Corp., Carlsbad, Calif.).

Plasmids were isolated from positive clones representing the variable regions of each hybridoma using a Qiagen mini prep kit (Qiagen 27106) according to the manufacturer's protocol. M13 forward and reverse primers were used to amplify DNA sequence for each cloned insert using the Big Dye sequencing reaction (Applied Biosystems by Life Technologies Corp., Carlsbad, Calif.) according to manufacturer's protocol. Sequencing reactions were purified using a 96 well purification kit (Zymo Research, Irvine, Calif.) according to the manufacturer's protocol. Samples were loaded onto an ABI-3730 capillary sequencer and resulting sequence traces were analyzed using Sequencher (GeneCodes v. 4.2) for presence of complete open reading frames. The murine anti canine IL-31 variable sequences determined for each antibody are as follows, 11E12 variable light chain (Seq ID NO:19 MU-11E12-VL, the corresponding nucleotide sequence for which is SEQ ID NO: 34), 11E12 variable heavy chain (Seq ID NO: 26 MU-11E12-VH, the corresponding nucleotide sequence for which is SEQ ID NO: 35), 19D07 variable light chain (Seq ID NO:22 MU-19D07-VL, the corresponding nucleotide sequence for which is SEQ ID NO: 36), 19D07 variable heavy chain (Seq ID NO: 28 MU-19D07-VH, the corresponding nucleotide sequence for which is SEQ ID NO: 37), 34D03 variable light chain (Seq ID NO:24 MU-34D03-VL, the corresponding nucleotide sequence for which is SEQ ID NO: 38), and 34D03 variable heavy chain (Seq ID NO:30 MU-34D03-VH, the corresponding nucleotide sequence for which is SEQ ID NO: 39).

To confirm the validity of cDNA sequence derived from each antibodies variable heavy and light chains, N-terminal sequence analysis was carried out on purified mAb protein using Edman degradation on an Applied Biosystems model 494 gas phase protein sequencer. Table 2 below describes the confirmation of variable light chain sequences for antibodies 11E12 and 34D03 and the variable heavy sequence of 34D03. The N-terminal amino acid of the variable heavy chain of antibody 11E12, derived by translation of the cDNA sequence, was determined to be glutamine. Glutamine, as amino terminal residue of a protein, can spontaneously undergo cyclization to pyroglutamic acid preventing sequence determination by Edman degradation (Chelius et al., Anal Chem. 2006 78(7):2370-6).

TABLE 2*

| Antibody | Translated cDNA Sequence | N-terminal Sequence |
|---|---|---|
| Variable Light Chain | | |
| 11E12 | DIVLT | DIVLT |
| 19D07 | DIVMS | not tested |
| 34D03 | DILLT | DILLT |
| Variable Heavy Chain | | |
| 11E12 | QVQLQ | blocked |
| 19D07 | EVKLV | not tested |
| 34D03 | EVQLV | EVQLV |

*In Table 2, "DIVLT" corresponds to residues 1-5 of SEQ ID NO: 19, "DIVMS" corresponds to residues 1-5 of SEQ ID NO: 22, "DILLT" corresponds to residues 1-5 of SEQ ID NO: 24, "QVQLQ" corresponds to residues 1-5 of SEQ ID NO: 26, "EVKLV" corresponds to residues 1-5 of SEQ ID NO: 28, and "EVQLV" corresponds to residues 1-5 of SEQ ID NO: 30.

Example 3

Construction of 11E12, 19D07 and 34D03 Chimeric Antibodies

As described above, antibodies are composed of a homodimer pairing of two heterodimeric proteins. Each protein chain (one heavy and one light) of the heterodimer consists of a variable domain and a constant domain. Each variable domain contains three complementary determining regions (CDRs) which contribute to antigen binding. CDRs are separated in the variable domain by framework regions which provide a scaffold for proper spatial presentation of the binding sites on the antibody. Together, the CDR and framework regions contribute to the antibodies ability to bind its cognate antigen (FIG. 2).

As further described above, a chimeric antibody consists of the variable sequence (both CDR and framework) from the mouse antibody (as determined from the above sequence analysis) grafted onto the respective heavy and light constant regions of a canine IgG molecule (FIG. 3). As the variable domain is responsible for antigen binding, grafting of the fully mouse variable domain onto canine constant region is expected to have little or no impact on the antibody's ability to bind the IL-31 immunogen.

To simultaneously confirm that the correct sequence of the heavy and light chain variable regions were identified and to produce recombinant, homogenous material, expression vectors to produce the chimeric antibodies in mammalian expression systems were generated. Forward and reverse primers were designed to amplify the mouse heavy and light chain variable region of antibody sequence derived from hybridomas 11E12, 19D07, and 34D03. A unique restriction endonuclease site, Kozak consensus sequence and, secretion leader sequence were incorporated into each forward primer to facilitate expression and secretion of the recombinant antibody from a mammalian cell line. Each reverse primer was designed to amplify each respective variable heavy and light chain and included a unique restriction site to facilitate cloning. PCR was performed to amplify each heavy and light chain using cloned hybridoma variable chain antibody DNA as a template for each reaction. Each PCR product was cloned into a mammalian expression plasmid containing either the canine IgG heavy (referred to herein as HC-64 or HC-65) or light chain (referred to herein as kappa) constant regions based on sequences from GenBank accession numbers AF354264 or AF354265 and XP_532962 respectively. The amino acid and nucleotide sequences of HC-64 are represented by SEQ ID NOs: 40 and 41, respectively. The amino acid and nucleotide sequences of HC-65 are represented by SEQ ID NOs: 42 and 43, respectively. The amino acid and nucleotide sequences of kappa are represented by SEQ ID NOs: 44 and 45, respectively. The plasmids encoding each heavy and light chain, under the control of the CMV promoter, were co-transfected into HEK 293 cells using standard lipofectamine methods. Following six days of expression, chimeric mAbs were purified from 30 ml of transiently transfected HEK293FS cell supernatants using MabSelect SuRe protein A resin (GE Healthcare, Uppsala, Sweden) according to standard methods for protein purification. Eluted fractions were pooled, concentrated to ~500 ul using a 10,000 nominal MW cutoff Nanosep Omega centrifugal device (Pall Corp., Port Washington, N.Y.), dialyzed overnight at 4° C. in 1×PBS, pH7.2 and stored at 4° C. for further use.

Expression of chimeric canine IgG was assessed using SDS polyacrylamide electrophoresis (SDS PAGE) under native and denaturing conditions. Monoclonal antibodies (mAbs) from each transfection were separated on a 4-12% Bis Tris gel using SDS MES running buffer according to the manufacturers protocol (Invitrogen Corp., Carlsbad, Calif.). Following electrophoresis, proteins were visualized with Simply Blue Coomassie Stain (Invitrogen Corp., Carlsbad, Calif.) to ensure proper pairing had occurred and provide a crude assessment of protein homogeneity. To evaluate whether the recombinant mAbs retained the ability to bind canine IL-31, mAbs were assessed for their ability to bind canine IL-31 via Western Blots. Protein standards and recombinant canine IL-31 (800 ng) were resolved on SDS PAGE transferred to a nitrocellulose membrane using the Invitrogen iBlot device (Invitrogen Corp., Carlsbad, Calif.). Following transfer, membranes were washed with distilled deionized water and blocked with 5% nonfat dried milk (NFDM) in phosphate buffered saline containing 0.05% tween-20 (PBST) for 1 hour at room temperature (RT). Following blocking, membranes were washed in PBST and incubated with either diluted supernatant from the transient expression or purified chimeric antibodies. Binding of the chimeric antibodies was evaluated using Goat anti-Dog IgG antibody-peroxidase conjugated (Bethyl Laboratories Inc., Montgomery, Tex. or Rockland, Immunochemicals, Inc., Gilbertsville, Pa.) at a 1:5000 dilution in PBST for 1 hour at RT. Confirmation of IL-31 binding was determined by the presence of a colorimetric band (apparent molecular weight 15 kDa) corresponding to the glycosylated form of canine IL-31 following addition of TMB substrate to the blot (KPL, Inc., Gaithersburg, Md.).

Chimeric mAbs showing expression from HEK 293 cells and binding to the recombinant canine IL-31 immunogen by Western blot were further analyzed for affinity and functionality. To characterize the affinity with which candidate mAbs bind IL-31, surface plasmon resonance (SPR) was evaluated using a Biacore system (Biocore Life Sciences (GE Healthcare), Uppsala, Sweden). To avoid affinity differences associated with differential surface preparation that can occur when immobilizing antibodies to surfaces; a strategy was employed where IL-31 was directly conjugated to the surface. Immobilization was obtained by amine coupling 5 μg/mL IL-31 using N-hydroxysuccinimide (NHS)/1-Ethyl-3-(3-dimethylaminopropyl)carbodiimide (EDC) chemistry. Chips were quenched with ethanolamine and the affinity with which all candidate mAbs bound to the immobilized IL-31 was evaluated. All curves were fit to a 1:1 model. Affinities <E-11 are below the lower limit of quantitation of detection for the instrument.

All candidate mAbs were also evaluated for their ability to inhibit IL-31 signaling in the cell-based assay in two independent formats. In the co-incubation format, mAb:IL-31 complexes were pre-incubated for one hour to ensure complex formation prior to cell addition. To increase the potential for differentiation between mAbs, a second set of experiments were performed that lacked co-incubation and mAbs were added directly to cells for 5 minutes followed by IL-31 addition. In both cases, IL-31 stimulation occurred for 5 minutes. As outlined in table 3 below, conversion of mouse monoclonals 11E12, 19D07 and 34D03 to a canine chimeric form, had little impact on their ability to bind IL-31 or inhibit cell-mediated signaling. The results also verify the correct variable heavy and variable light chain sequences derived from each mouse hybridoma.

TABLE 3

| Antibody | DH82 pSTAT Assay | | Biacore |
|---|---|---|---|
| | Co-incubation $IC_{50}$ μg/ml | Pre-treatment $IC_{50}$ μg/ml | Affinity $K_D$ (M) |
| Mouse 11E12 | 1.61 | 2.28 | 8.93E-13 |
| *Chimeric 11E12 | 1.48 | 1.57 | 2.68E-13 |
| Mouse 19D07 | 1.76 | 3.46 | 7.24E-12 |
| ×Chimeric 19D07 | 1.92 | 1.33 | 5.15E-13 |
| Mouse 34D03 | 1.73 | 2.28 | 1.01E-12 |
| □Chimeric 34D03 | 1.28 | 1.08 | 4.65E-12 |

*Chimeric 11E12-for the heavy chain, MU-11E12-VH was paired with HC-64, and for the light chain, MU-11E12-VL was paired with kappa.
×Chimeric 19D07-for the heavy chain, MU-19D07-VH was paired with HC-64, and for the light chain, MU-19D07-VL was paired with kappa.
□Chimeric 34D03-for the heavy chain, MU-34D03-VH was paired with HC-64, and for the light chain, MU-34D03-VL was paired with kappa.

Example 4

In vivo Evaluation of Chimeric mAbs

To confirm that the inhibition of IL-31-mediated cell signaling, observed in the DH-82 assay, correlates with inhibition of IL-31-mediated pruritus in the dog, the chimeric 11E12 monoclonal antibody described above in Table 3 (Chimeric 11E12-64) was evaluated in the IL-31 dog pruritus model. In this model, canine IL-31, when given intravenously (IV) at a dose of 1 to 1.5 μg/kg, produces a fast onset consistent pruritic response that can be quantitated over a two hour period of observation. To evaluate pruritic responses, dogs were placed in single housed pens and pruritic activity measurements were performed using video surveillance. Following an acclimation period of ≥1 hour, pruritic baseline scores were determined for each dog using real-time video surveillance using a categorical scoring system. Specifically, at consecutive 1 minute intervals, "yes/no" decisions were made in regards to whether pruritic behavior was displayed by each dog. Display of pruritic behavior such actions as licking/chewing of paws, flank, and/or anal regions, scratching of flanks, neck, and/or flooring, head-shaking, and scooting of their bottom across the cage flooring was sufficient to elicit a "yes" response over the designated time interval. At the end of this period, the numbers of yes determinations were added together to come up with a cumulative Pruritic Score Index (PSI). Pruritic scores were determined twice for each animal, with the first measurement being a 30 minute baseline score measured immediately prior to the start of the test-article treatment period. After completion of each scheduled observation period, the dogs were returned to their normal housing locations.

To evaluate whether subcutaneous (SC) administration of chimeric 11E12-64 can inhibit IL-31-mediated pruritus, a pilot study (76A03) was performed that included both a treated and a placebo group (N=4/group). In this study, baseline responses were performed with all 8 dogs and dogs were randomized into groups and housed based on their PSI. Importantly, each group consisted of two high responders (PSI>55) and two moderate responders (PSI=30 to 55). These dogs were then administered chimeric 11E12-64 on day 7 and IL-31 challenges were performed at day 8, 14 and 22. The results of this study are presented in FIG. 8. These results demonstrate that the administration of chimeric 11E12-64 resulted in a greater than 75% reduction in mean PSI for day 8 and 14, relative to day 1, for chimeric 11E12-64 treated animals. This is in contrast to a 37-51% increase in PSI scores for untreated animals. The PSI had returned to baseline two weeks following mAb treatment, suggesting a duration of efficacy between one and two weeks for the 0.3 mg/kg dose administered.

A particular challenge when assessing PSI is the day to day variation associated with dog pruritic behavior. To help control for this variation, the 30 minute baseline PSI was determined for each dog, on each day prior to IL-31 challenge. FIG. 9 shows the individual pruritic scores from doges enrolled in this study (76A60). The data in FIG. 9 illustrates that the day 8 and day 14 baseline PSI was approximately 25% of the post IL-31 challenge in the chimeric 11E12-64 treated group. This observation is consistent with a complete abrogation of IL-31 related pruritus since the baseline observation time period (0.5 h) is 25% of the post IL-31 observation time period (2h). Taken together, these in vivo data provide very strong evidence that; 1) the chimeric 11E12 monoclonal can neutralize the ability of IL-31 to induce pruritus in dogs, 2) inhibition of IL-31 mediated signaling in the cell based assay correlates with in vivo efficacy and 3) the parameters necessary to utilize this IL-31 model for mAb evaluation are established for the evaluation of other candidate antibodies.

Example 5

Caninization Strategy

The generation of anti-drug antibodies (ADAs) can been associated with loss of efficacy for any biotherapeutic protein including monoclonal antibodies. Comprehensive evaluation of the literature has shown that speciation of monoclonal antibodies can reduce the propensity for mAbs to be immunogenic although examples of immunogenic fully human mAbs and non-immunogenic chimeric mAbs can be found. To help mitigate risks associated with ADA formation for the mouse anti IL-31 monoclonal antibodies provided herein, a caninization strategy was employed. This caninization strategy is based on identifying the most appropriate canine germline antibody sequence for CDR grafting (FIG. 4). Following extensive analysis of all available canine germline sequences for both the heavy and light chain, germline candidates were selected based on their homology to the mouse mAbs, and the CDRs from the mouse progenitor mAbs were used to replace native canine CDRs. The objective was to retain high affinity and cell-based activity using fully canine frameworks to minimize the potential of immunogenicity in vivo. Caninized mAbs were expressed and characterized for their ability to bind IL-31 via Western blotting. These results are described below in Example 8. Only mAbs that retained the ability to bind IL-31 following caninization were advanced for further characterization. Those mAbs that lost the ability to bind IL-31 were systematically dissected to identify; 1) the chain responsible for the loss of function, 2) the framework responsible for the loss of function and 3) the amino acid(s) responsible for the loss function.

Example 6

Caninization of 11E12, 19D07, and 34D03 Antibodies

Synthetic nucleotide constructs representing the caninized variable heavy and light chains of mAbs 11E12, 19D07, and 34D03 were made. Following subcloning of each variable chain into plasmids containing the respective canine heavy or kappa constant region, plasmids were co-transfected for antibody expression in HEK 293 cells. In summary, both the 19D07 and 34D03 mAbs retained IL-31 binding upon caninization. The caninized anti-canine IL-31 variable sequences determined for each antibody are as follows, 19D07 variable light chain (Seq ID NO: 23 CAN-19D07-VL-998-1, the corresponding nucleotide sequence for which is SEQ ID NO: 46), 19D07 variable heavy chain (Seq ID NO: 29 CAN-19D07-VH-400-1, the corresponding nucleotide sequence for which is SEQ ID NO: 47), 34D03 variable light chain (Seq ID NO: 25 CAN-34D03-VL-998-1, the corresponding nucleotide sequence for which is SEQ ID NO: 48), and 34D03 variable heavy chain (Seq ID NO: 31 CAN-34D03-VH-568-1, the corresponding nucleotide sequence for which is SEQ ID No: 49).

Figure 10:
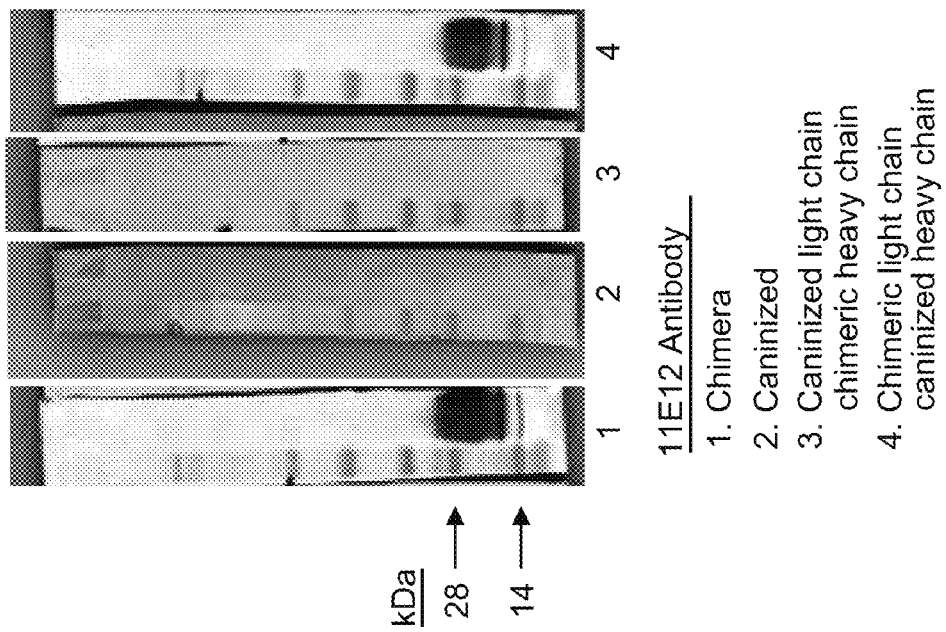
FIG. 10 is of Western blots showing binding of chimeric (Blot #1), caninized (Blot#2), and heterochimeric (Blots #3 and 4) versions of 11E12 to canine IL-31. The heterochimera in Blot #3 has a caninized light chain paired with a chimeric heavy chain. The heterochimera in Blot #4 has the chimeric light chain paired with the caninized heavy chain. Each nitrocellulose blot contains-left lane, pre-stained protein standards (Seeblue plus 2, Invitrogen Corp., Carlsbad, Calif.) and right lane, 800 ng of canine IL-31.

In contrast, the germline sequences used for the 11E12 caninization efforts resulted in certain non-functional mAbs. With reference to FIG. 10, chimeric, heterochimeric, and caninized versions of mAb 11E12 were expressed and characterized for their ability to bind canine IL-31 via Western blotting. These results demonstrated that the caninized 11E12 antibody did not bind canine IL-31 (Blot #2). Also, with respect to the heterochimeras, the chimeric heavy chain paired with the caninized light lost IL-31 binding (Blot #3), while the caninized heavy chain paired with the chimeric light retained IL-31 binding activity (Blot #4). Based on the results obtained from the heterochimeras, it was deduced that the caninized light chain was responsible for the loss of activity.

In an effort to restore the binding of caninized versions of 11E12 to canine IL-31, the caninized light chain was modified by swapping framework sequences. FIG. 11 provides an overview of the 11E12 light chain framework substitution work. This work identified an antibody replacing the canine framework II (FWII) with mouse framework II and restoring binding to canine IL-31 (11E12 variable light chain (Seq ID NO: 20 CAN-11E12-VL-cUn-FW2, the corresponding nucleotide sequence for which is SEQ ID NO: 50), 11E12 variable heavy chain (Seq ID NO: 27 CAN-11E12-VH-415-1, the corresponding nucleotide sequence for which is SEQ ID NO: 51)).

Figure 12:
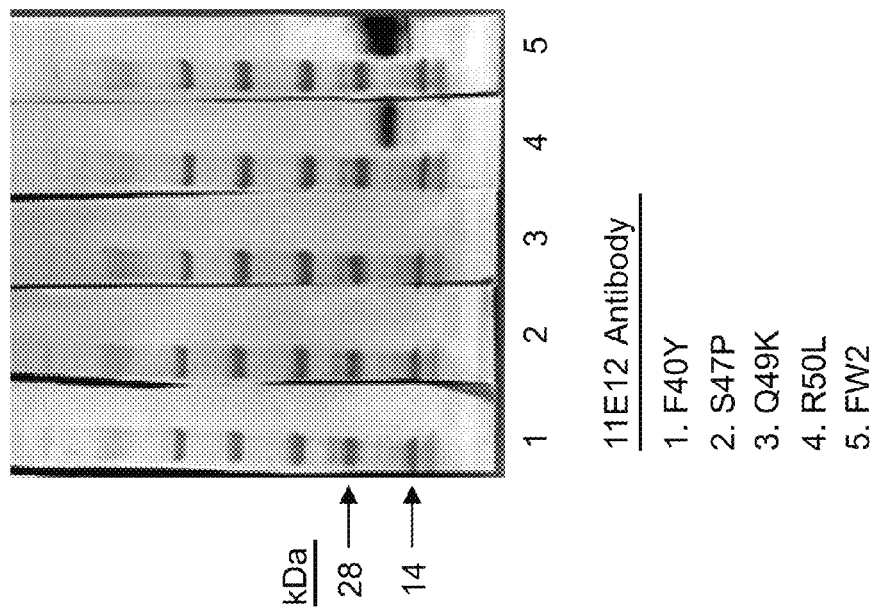
FIG. 12 is of Western blots showing binding of caninized versions of 11E12 with single backmutations to mouse framework 2 light chain residues. Each nitrocellulose blot contains—left lane, pre-stained protein standards (Seeblue plus 2, Invitrogen Corp., Carlsbad, Calif.) and right lane, 800 ng of canine IL-31.

Further refinement of these back mutations identified an antibody with a single arginine to leucine back mutation (R50L) in framework II could restore IL-31 binding via Western blot analysis (11E12 variable light chain (Seq ID NO: 21 CAN-11E12-VL-cUn-13, the corresponding nucleotide sequence for which is SEQ ID NO: 52), 11E12 variable heavy chain (Seq ID NO: 27 CAN-11E12-VH-415-1)) (FIG. 12). Once 'caninized' versions of each potential candidate were identified the mAbs were purified and dialyzed into PBS for further evaluation.

Table 4 summarizes the results of both the affinity measurements and cell-based inhibition data. These data demonstrate that the caninized derivatives of both 11E12 and 34D03 both retain excellent inhibitory activity in the cell based assay and affinity to IL-31 as measured by Biacore. Also worth noting is the observation that while the original caninized 19D7 molecule retains excellent potency as measured by Biacore, the ability to inhibit cell based IL-31 signaling appears compromised relative to its mouse progenitor. Little to no affinity loss was incurred when converting mAbs from their mouse isotype to the canine derivative.

TABLE 4

| Antibody | DH82 pSTAT Assay | | Biacore |
| --- | --- | --- | --- |
| | Co-incubation IC$_{50}$ µg/ml | Pre-treatment IC$_{50}$ µg/ml | Affinity K$_D$ (M) |
| Mouse 11E12 | 1.61 | 2.28 | 8.93E-13 |
| Caninized 11E12 | not active | not active | 5.06E-07 |
| 11E12 Heterochimera | 2.67 | 3.35 | 4.97E-12 |
| Caninized 11E12 FW2 | 2.7 | 5.31 | 1.47E-10 |
| Caninized 11E12 13 | 5.49 | 5.18 | 5.16E-12 |
| Mouse 19D07 | 1.76 | 3.46 | 7.24E-12 |
| Caninized 19D07 | inc. curve | inc. curve | 9.23E-10 |
| Mouse 34D03 | 1.73 | 2.28 | 1.01E-12 |
| Caninized 34D03 | 2.42 | 2.25 | 2.91E-11 |

| | Variable Chain | |
| --- | --- | --- |
| Antibody | Heavy | Light |
| Caninized 11E12 | CAN-11E12-VH-415-1 | CAN-11E12-VL-cUn-1 |
| 11E12 Heterochimera | CAN-11E12-VH-415-1 | Chimeric 11E12 |
| Caninized 11E12 FW2 | CAN-11E12-VH-415-1 | CAN-11E12-VL-cUn-FW2 |
| Caninized 11E12 13 | CAN-11E12-VH-415-1 | CAN-11E12-VL-cUn-13 |
| Caninized 19D07 | CAN-19D07-VH-400-1 | CAN-19D07-VL-998-1 |
| Caninized 34D03 | CAN-34D03-VH-568-1 | CAN-34D03-VL-998-1 |

Heavy chains: All Caninized and heterochimeric forms of 11E12 included the V$_H$ sequence of CAN-11E12-VH-415-1 (SEQ ID NO: 27) and the constant region termed HC-64 (SEQ ID NO: 40); Caninized 19D07 included the V$_H$ sequence of CAN-19D07-VH-400-1 (SEQ ID NO: 29) and HC-64; Caninized 34D03 included the V$_H$ sequence of CAN-34D03-VH-568-1 (SEQ ID NO: 31) and HC-64.
Light Chains: Caninized 11E12 included the V$_L$ sequence of CAN-11E12-VL-cUn-1 (SEQ ID NO: 53) and the constant region termed kappa (SEQ ID NO: 44); Heterochimeric 11E12 included the V$_L$ sequence of MU-11E12-VL (SEQ ID NO: 19) and kappa; Caninized 11E12 FW2 included the V$_L$ sequence of CAN-11E12-VL-cUn-FW2 (SEQ ID NO: 20) and kappa; Caninized 11E12 13 included the V$_L$ sequence of CAN-11E12-VL-cUn-13 (SEQ ID NO: 21) and kappa; Caninized 19D07 included the V$_L$ sequence of CAN-19D07-VL-998-1 (SEQ ID NO: 23) and kappa; Caninized 34D03 included the V$_L$ sequence of CAN-34D03-VL-998-1 (SEQ ID NO: 25) and kappa.

Example 7

Characterization of Canine IL-31 Binding to Antibodies 11E12 and 34D03

Figure 13:
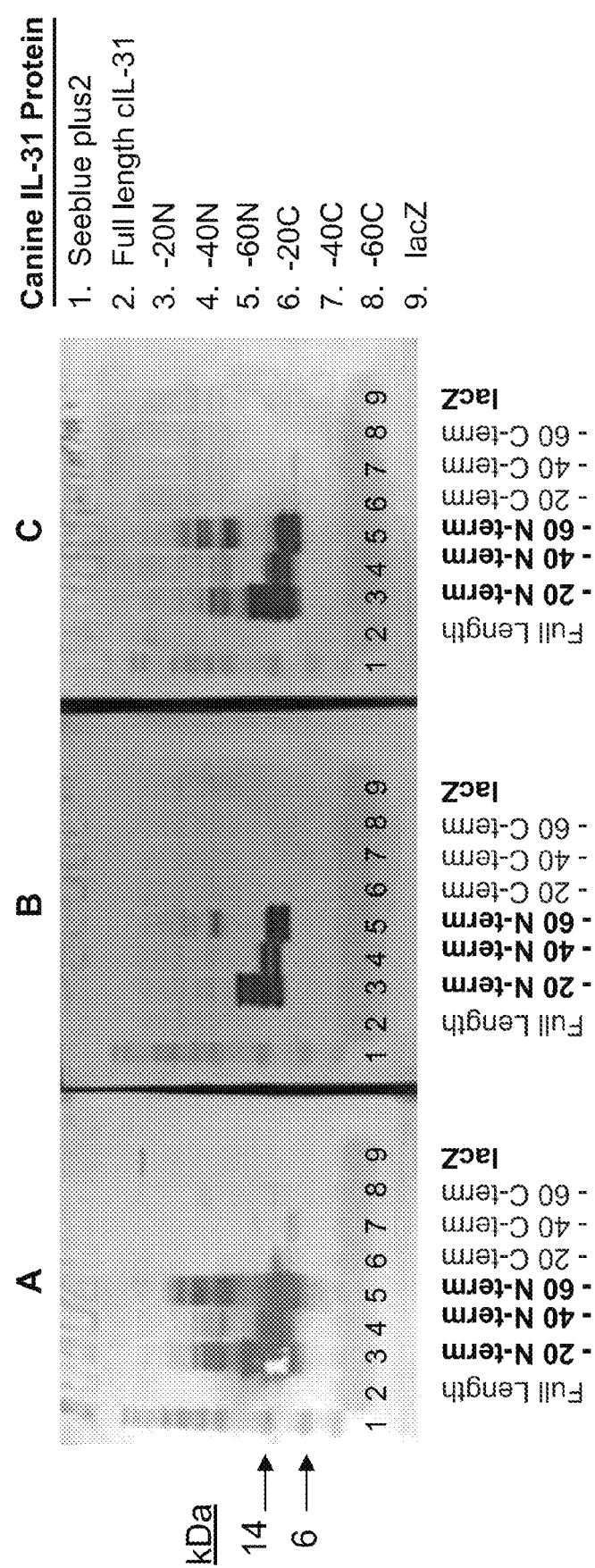
FIG. 13 is of Western blots with full length and truncated canine IL-31 proteins. Individual nitrocellulose blots were probed with A) anti-His B) 34D03 and C) 11E12 antibodies. Lanes 1-9 of the blots correspond to the following: Lane 1-pre-stained protein standards (Seeblue plus 2, Invitrogen Corp., Carlsbad, Calif.); Lane 2-full-length canine IL-31; Lane 3-N-terminal truncation –20N; Lane 4-N-terminal truncation –40N; Lane 5-N-terminal truncation –60N; Lane 6-C-terminal truncation –20C; Lane 7-C-terminal truncation –40C; Lane 8-C-terminal truncation –60C; and Lane 9-beta-galactosidase (lacZ). Note: full length IL-31 and proteins with C-terminal truncations (–20, –40 C., and –60 C.) showed no detectable expression under these conditions.

To determine the amino acid residues involved with binding of canine IL-31 to antibodies 11E12 and 34D03, a mutational strategy was used that involved 1) truncation of the IL-31 protein from both the N and C terminus and 2) replacement of individual amino acids with alanine (ala scan) to determine the impact on mAb binding. PCR primers were designed to amplify a canine IL-31 gene that was codon optimized for expression in an *E. coli* host. The sequence of this codon-optimized canine IL-31 full-length construct for *E. coli* expression is represented by SEQ ID NO: 55, the corresponding nucleotide sequence for which is SEQ ID NO: 56. Primers were designed to amplify the full length gene and to create 20 amino acid truncations of the protein moving inward from the N and C termini. For the purpose of these N-terminal truncations, position 1 corresponded to the glycine residue immediately following the N-terminal 6-His tag in the codon-optimized construct. PCR amplification products were cloned into pET101D (Invitrogen Corp., Carlsbad, Calif.) according to the manufacturers protocol. The pET101D plasmid allows fusion of the recombinant protein to an N-terminal 6-His epitope tag for confirmation of expression. Sequence confirmed plasmids were used to transform BL21 Star TOP10 *E. coli* cells (Invitrogen Corp., Carlsbad, Calif.) and expression of the recombinant protein was induced using 1 mM Isopropyl β-D-1-thiogalactopyranoside (IPTG) under standard culture conditions. Following inductions, cells were pelleted and lysed using Bacterial Protein Extraction Reagents (abbreviated B-PER, ThermoFisher Scientific Inc., Rockford, Ill.). Crude lysates were subjected to SDS-PAGE and Western blotting was carried out as described previously. All Western blotting for mutational analysis was performed using the mouse versions of 11E12 and 34D03 due to the availability of necessary purified antibodies and reagents. Each antibody was tested for its ability to bind the crude protein lysate blot representing full length and truncated IL-31. Control blots were also probed with the anti-His mAb to confirm expression of each protein. Proteins with an N-terminal truncation (−20N, −40N, and −60N) all showed robust expression in *E. coli* and were capable of binding to 11E12 and 34D03 (FIG. 13). The amino acid and nucleotide sequences corresponding to the −20N construct are SEQ ID NOs: 57 and 58, respectively. The amino acid and nucleotide sequences corresponding to the −40N construct are SEQ ID NOs: 59 and 60, respectively. The amino acid and nucleotide sequences corresponding to the −60N construct are SEQ ID NOs: 61 and 62, respectively. However, full length IL-31 and proteins with C-terminal truncations (−20 C., −40 C., and −60 C.) failed to express under these conditions.

Figure 14:
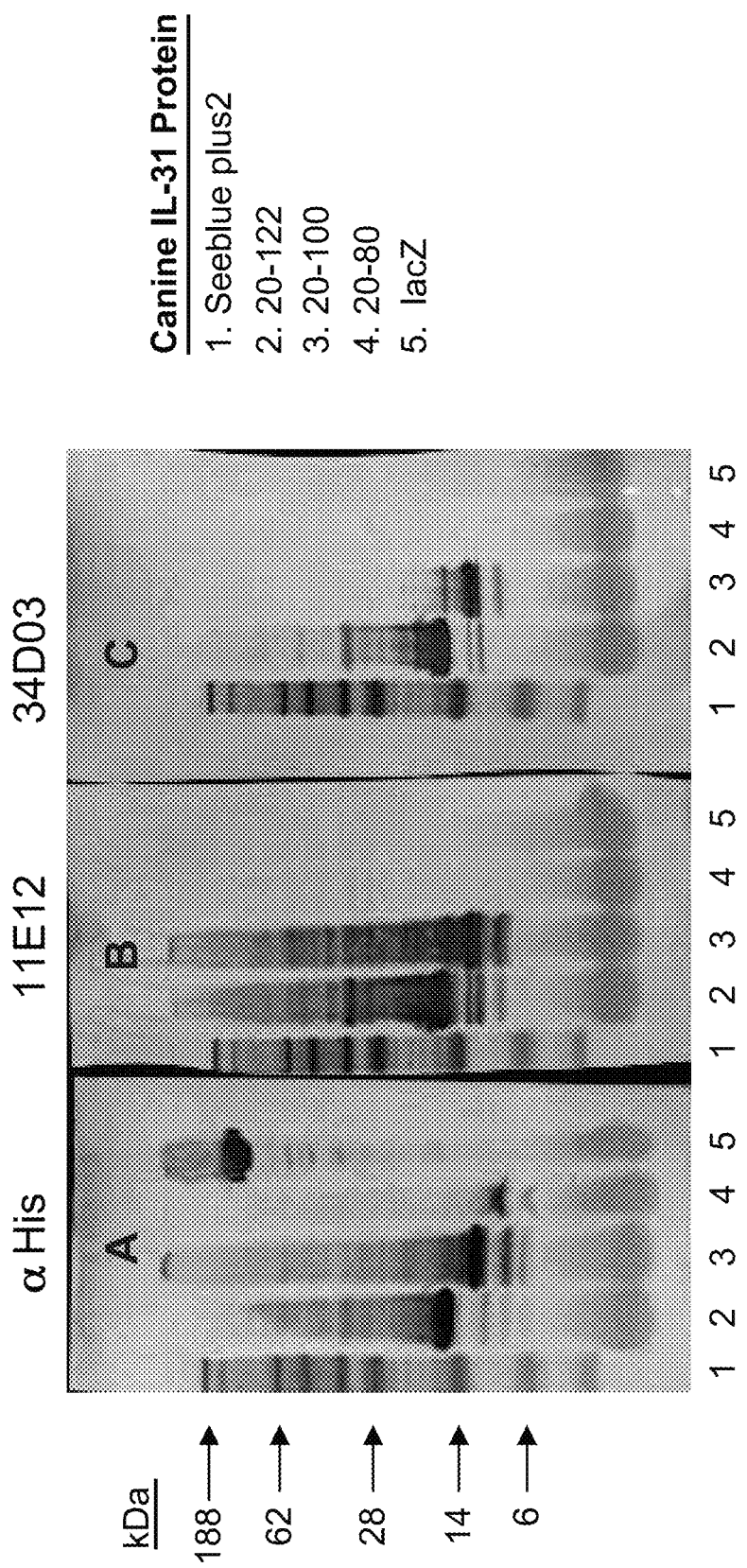
FIG. 14 is of Western blots with truncated canine IL-31 proteins. Individual nitrocellulose blots were probed with A) anti-His B) 11E12 and C) 34D03 antibodies. Lanes 1-5 of the blots correspond to the following: Lane 1-pre-stained protein standards (Seeblue plus 2, Invitrogen Corp., Carlsbad, Calif.); Lane 2-C-terminal truncations at positions 20-122; Lane 3-C-terminal truncations at positions 20-100; Lane 4-C-terminal truncations at positions 20-80; and Lane 5-beta-galactosidase (lacZ).

It was observed that the full length IL-31 protein was expressed very poorly. However, the construct with the first 20 amino acids removed (−20N) from the N-terminus showed robust expression. Antibodies 11E12 and 34D03 all bound to the −20N protein. Therefore, further work was carried out using this −20 N construct. Constructs representing C-terminal truncations at positions 20-122 (MW 15.3 with his tag), 20-100 (MW 12.9 with his tag), and 20-80 (MW 10.4 with his tag), were made to assess mAb binding to these areas on the IL-31 protein. The amino acid and nucleotide sequences corresponding to the 20-122 construct are SEQ ID NOs: 63 and 64, respectively. The amino acid and nucleotide sequences corresponding to the 20-100 construct are SEQ ID NOs: 65 and 66, respectively. The amino acid and nucleotide sequences corresponding to the 20-80 construct are SEQ ID NOs: 67 and 68, respectively. FIG. 14 shows Western blots of crude protein lysates of these truncated proteins that were probed with mAbs 11E12 (Blot B) and 34D03 (Blot C). As shown in this Figure, mAbs 11E12 and 34D03 bound to IL-31 truncated proteins 20-122 and 20-100, but failed to bind to 20-80. These results indicated that amino acids between positions 80 and 100 of the canine IL-31 full-length construct of SEQ ID NO: 55 (using "SSHMA" as the N-terminus) were involved with binding of these antibodies. This region corresponds to amino acid Nos. between amino acid residues 102 and 122 of the canine IL-31 full-length protein sequence of SEQ ID NO: 32. A control blot using the anti-His mAb (Blot A) showed that all truncated proteins were being expressed. In addition, the pET101D-lacZ protein was used as a control to confirm the lack of non-specific binding of mAbs to host proteins.

Figure 15:
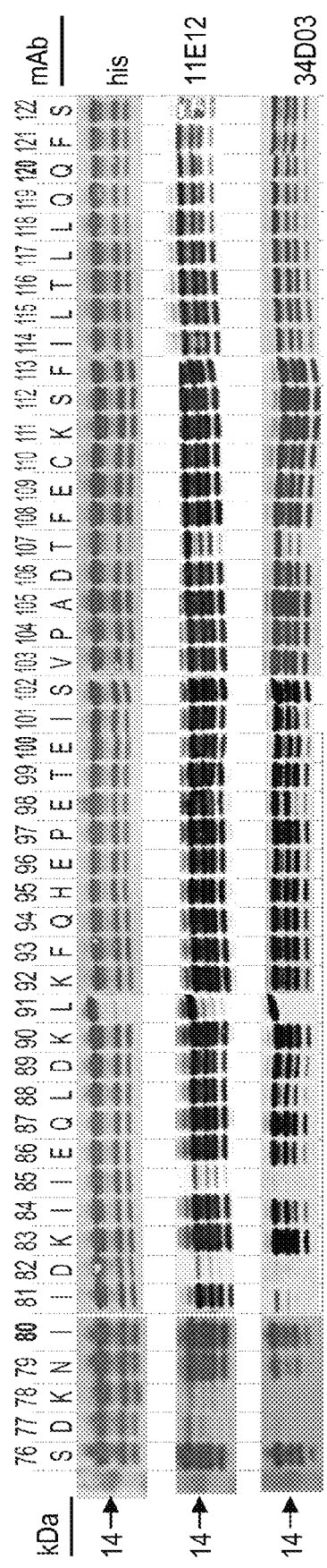
FIG. 15 is a section of Western blots with lysates of *E. coli* strains expressing canine IL-31 with alanine substituted for each amino acid position (76-122). Individual nitrocellulose blots were probed with anti-His, 11E12 and, 34D03 antibodies, as shown in the Figure.

To further identify the amino acids in canine IL-31 involved with binding to mAbs 11E12 and 34D03, alanine-scanning mutagenesis was performed according to known methods. Individual constructs were made (in the −20N plasmid) substituting alanine for each position on canine IL-31 from amino acids 76 through 122. Following sequence confirmation, protein expression was carried out and crude protein lysates were subjected to Western blot analysis. FIG. 15 shows a summary of results indicating positions on canine IL-31 that, when mutated to alanine, impact binding by mAbs 11E12 and 34D03. As shown in this Figure, positions 77, 78, 81 and 85 of the full-length IL-31 construct all impact binding of 11E12 or 34D03 antibodies. These correspond to amino acid residues 99, 100, 103 and 107, respectively, of the canine IL-31 full-length protein sequence of SEQ ID NO: 32.

Figure 16:
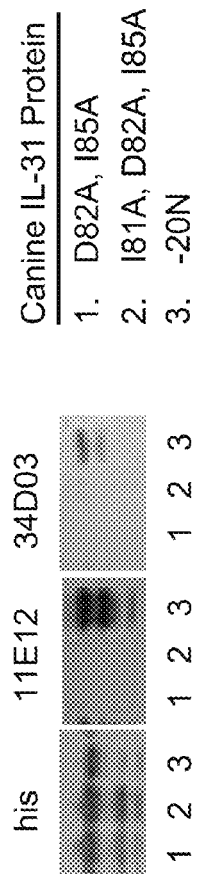
FIG. 16 is a section of Western blots with double and triple mutations in canine IL-31. –20N protein lysate was run as a positive control.
Figure 17:
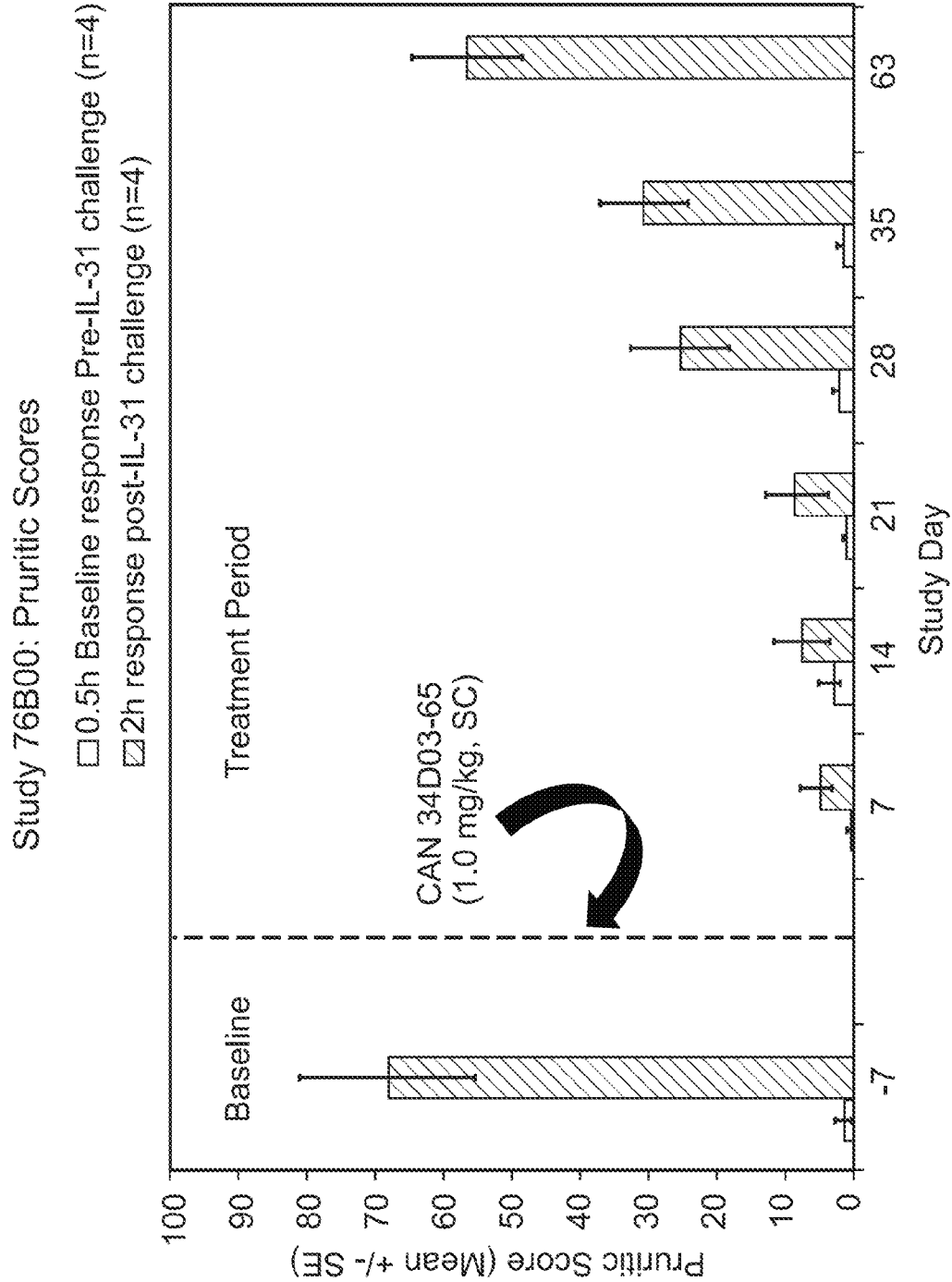
FIG. 17 is a graph showing the pruritic scores for dogs injected subcutaneously with caninized 34D03 antibody (1.0 mg/kg). Pruritic scores were measured on each study day prior to (baseline response) and following (2 h response) challenge with 1.5 µg/kg canine IL-31.
Figure 18:
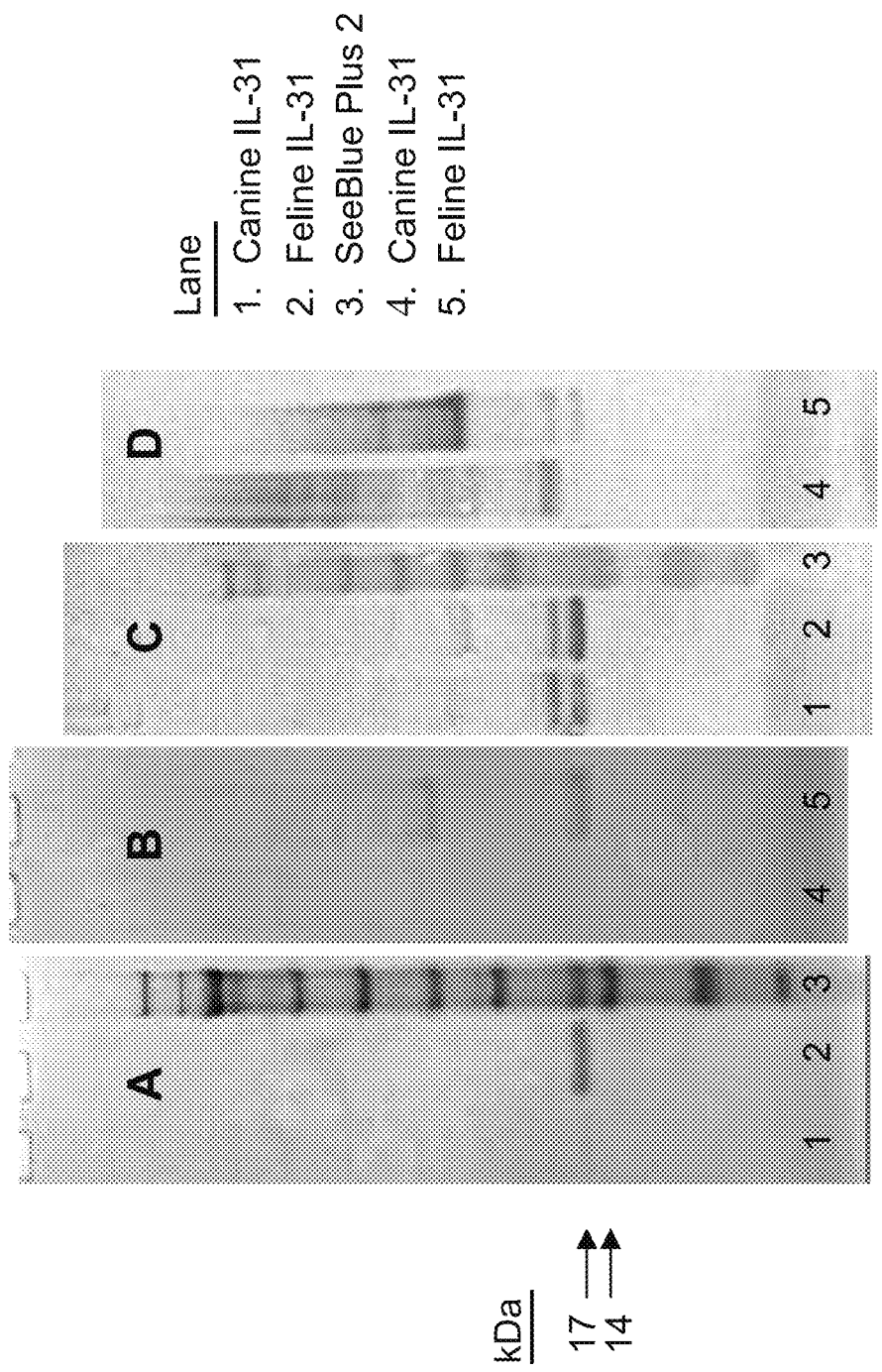
FIG. 18 is a 4-12% Bis Tris SDS PAGE with purified canine and feline IL-31 proteins. Panel A shows coomassie staining of proteins run under reducing conditions. Panel B shows coomassie staining of proteins run under non-reducing conditions Panels. Panels C and D are the Western blots of gels identical to A and B respectively, probed with an anti-His antibody. Lane 1-canine IL-31; Lane 2-feline IL-31; Lane 3-pre-stained protein standards (Seeblue plus 2, Invitrogen Corp., Carlsbad, Calif.); Lane 4-canine IL-31; and Lane 5-feline IL-31.
Figure 19:
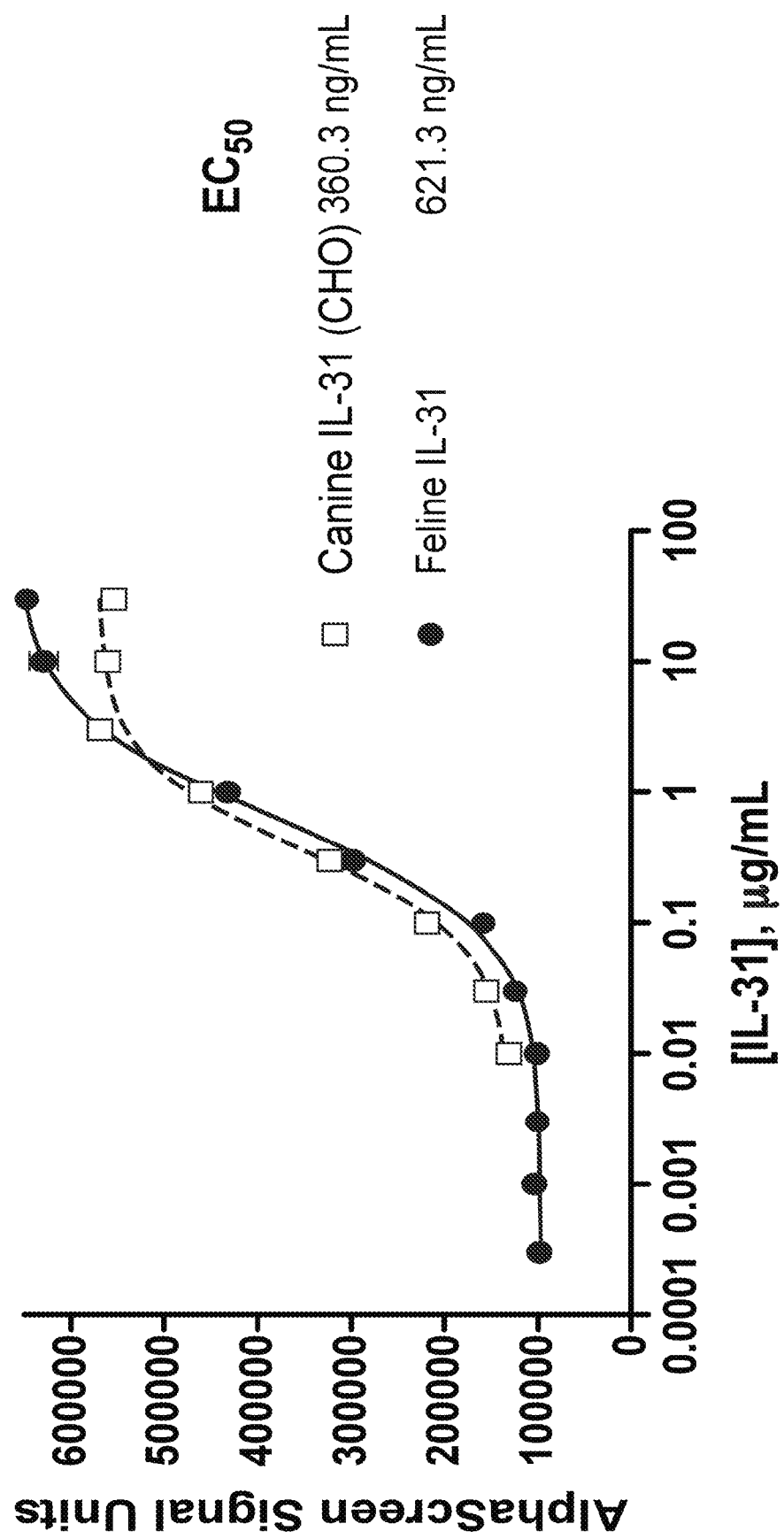
FIG. 19 is a graph of pSTAT signaling in canine DH-82 monocytes induced by canine and feline IL-31 produced in *E. coli*. Canine IL-31 (CHO) is the reference protein used for all previous cell-based assays, dog pruritus model, and as the immunogen for initial identification of antibodies.

To examine the impact of multiple mutations in the region of IL-31 important for binding to the 11E12 and 34D03 antibodies, expression plasmids were constructed with double (D82A, I85A) and triple (I81A, D82A, I85A) alanine substitutions. E. coli lysates expressing canine IL-31 with these double and triple mutations in addition to the –20N control were blotted with 11E12 and 34D03 antibodies (FIG. 16). It is apparent that these three amino acids on canine IL-31 are involved with recognition of 11E12 and 34D03 as complete abrogation of binding is observed when these sites are changed to alanine. These three amino acids correspond to amino acid residues 103, 104 and 107 of the canine IL-31 full-length protein sequence of SEQ ID NO: 32.

In summary, truncation analysis of canine IL-31 revealed amino acid residues (annotated in FIG. 15 between positions 80 and 122) are involved in binding 11E12 and 34D03 antibodies. Further, fine mutational analysis using alanine scanning revealed that ASP77, LYS78, ILE81, ASP82, and ILE85 of the full-length IL-31 construct all impact binding of 11E12 or 34D03 indicating this region most likely defines the epitope responsible for recognition by these antibodies. Interestingly, this region of the human IL-31 protein was shown to be involved with binding to the GPL subunit of its co-receptor (Le Saux S et al. Biol. Chem. 2010 Jan. 29; 285(5):3470-7. Epub 2009 Nov. 17). These observations, along with the ability of mAbs 11E12 and 34D03 to neutralize IL-31 mediated pSTAT activity in monocytes, support the hypothesis that these mAbs bind to residues on canine IL-31 that are essential for binding of this cytokine to its receptor, thereby inhibiting its ability to induce signaling.

Example 8

Production of Caninized 34D03 Antibodies from Glutamine Synthetase (GS) Plasmids The genes encoding the caninized 34D03 mAb (heavy and light chains, Table 4 above) were cloned into GS plasmids pEE 6.4 and pEE 12.4, respectively (Lonza, Basel, Switzerland). The resulting plasmids were digested according to the manufacturer's protocol and ligated together to form a single mammalian expression plasmid. Each plasmid was used to transfect HEK 293 cells and expression was carried out in 20L of culture media. Protein was isolated from conditioned HEK medium using Protein A affinity chromatography according to standard protein purification methods. Medium was loaded onto chromatographic resin and eluted by pH shift. Eluted protein was pH adjusted, dialyzed, and sterile filtered prior to use. The resulting antibody was greater than 99 percent monomeric by analytical size exclusion chromatography with no high molecular weight aggregates observed. This antibody was subsequently used for evaluation in the dog pruritus model to evaluate in vivo efficacy.

Example 9

Evaluation of the Caninized 34D03 Antibody in the Dog Pruritus Model

The anti-pruritic activity of caninized 34D03 (CAN 34D03-65 represented by SEQ ID NO 31 (VH) paired with SEQ ID NO 25 (VL) on SEQ ID NO 42 (HC-65) and SEQ ID NO 44 (LC-Kappa)) was evaluated using a canine model of IL-31-induced pruritus. With this model, a 1.5 μg/kg intravenous challenge dose of recombinant canine IL-31 known to induce a transient period of pruritic behavior in beagle dogs (IL-31 challenge, pruritus duration <24 hour) was repeatedly delivered to animals before and up to 63 days after a single 1.0 mg/kg SC dose of CAN 34D03-65. At each IL-31 challenge period, real-time video surveillance was used to obtain a measure of pruritic behavior for 0.5 hours prior to cytokine delivery (pre-IL-31 baseline period) followed by a similar 2 hour measurement beginning 20 minutes after cytokine injection (2 h post-IL-31 challenge period). Pruritic scores were generated at each time period under evaluation by making "yes/no" determinations as to whether a pruritic behavior was displayed over consecutive 1 minute time-intervals (maximal pruritic score=30 for each baseline period; 120 for the post-IL-31 challenge period). FIG. 17 summarizes the pruritic scores obtained before and after CAN 34 D03-65 treatment, which was given on day 0 of the study. Seven days prior to mAb treatment, the mean post-IL-31 challenge pruritic score of the dogs was 68±13 (S.E., n=4). By comparison, on study days 7, 14, 21, the mean post-IL-31 challenge pruritic scores had lowered to 5±2, 8±4, and 9±5, respectively. These changes in pruritic score between day −7 and days 7-21 represent a ≥85% decrease in overall pruritic reactivity to IL-31. The degree of inhibition of IL-31-induced pruritus may actually have been closer to 100% over this time-frame if one considers that between days 0 and 21, the 0.5 h pre-IL-31 baseline scores averaged 1.6±0.6—a level that would extrapolate to a pruritic score of 6-7 over a 2 h period. The pruritic reactivity of the treated dogs to exogenous IL-31 did gradually recover over time. By day 63 post-CAN D03-65 treatment, the mean 2 h post-IL-31 challenge pruritic score had increased to 57±8 or roughly 84% of the pre-mAb IL-31 challenge responses observed on day −7. Thus, in a model of IL-31-induced pruritus, a single bolus SC injection of CAN 34D03-65 did provide weeks of anti-pruritic protection to treated dogs.

Example 10

Characterization of Feline IL-31

The sequence of feline IL-31 was identified by a similarity searching of the feline genome with canine IL-31 using the NCBIs genome resources (www.ncbi.nlm.nih.gov). The gene representing feline IL-31 was synthesized for optimal expression in *E. coli*. Expression constructs were created with full length canine and feline IL-31 genes containing an N-terminal 6-His tag for detection and purification. The feline full-length construct used for expression in *E. coli* is represented by the nucleotide sequence of SEQ ID NO: 69 and the protein sequence of SEQ ID NO: 70. Sequence confirmed plasmids were used to transform *E. coli* BL21 Star™ (Invitrogen Corp., Carlsbad, Calif.) and expression was carried out at 30 C for 5 hours. Following lysis of cell pellets immunoreactive reactive protein was found to be highly enriched in the insoluble lysate. These cell pellets were solubilized in 6M urea and purification of the recombinant proteins was carried out under denaturing conditions using a nickel cobalt resin (Thermo Fisher Scientific Inc., Rockford, Ill.). Pooled eluted fractions, shown to be positive for the presence of the His tag, were step dialyzed against 0.8 M urea PBS followed by PBS, and analyzed by SDS PAGE (FIG. 18). As was previously observed, the yield of recombinant canine IL-31 from *E. coli* induction was low. However, protein was recovered post purification that migrated according to expected molecular mass via SDS-PAGE.

To examine the biological activity of canine and feline IL-31 produced from *E. coli*, each protein was analyzed for its ability to induce pSTAT signaling in the DH82 cell assay. As recombinant IL-31 from mammalian cells (canine IL-31 (CHO)) is highly glycosylated, it was unclear whether the unglycosylated form would retain biological activity. FIG. 19 shows that feline IL-31 has comparable bioactivity to the reference reference IL-31 produced in CHO cells.

Figure 20:
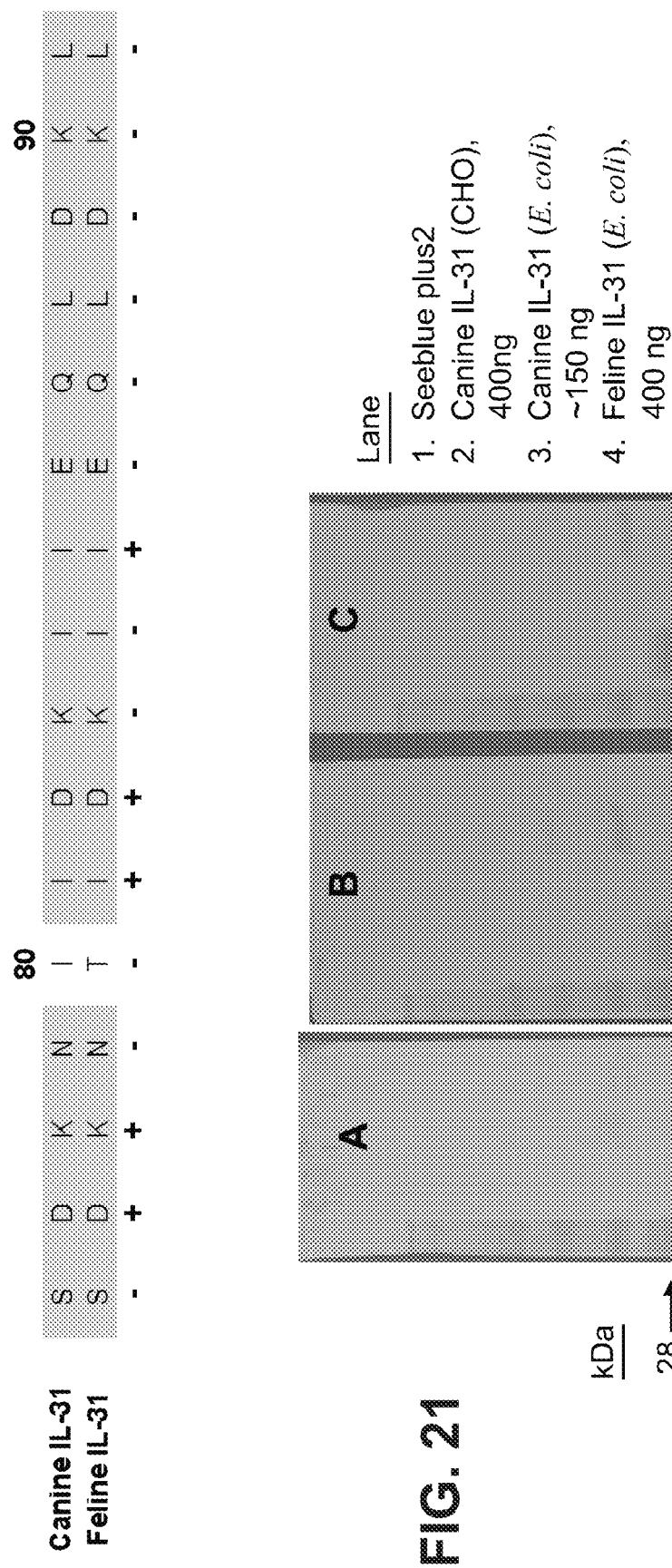
FIG. 20 is an alignment showing the sequence conservation between feline and canine IL-31 in the region of the protein involved in binding of 11E12 and 34D03 antibodies (annotated with a plus sign). The canine IL-31 sequence corresponds to amino acid residues 98 to 113 of SEQ ID NO:32; and the feline IL-31 sequence corresponds to amino acid residues 87 to 102 of SEQ ID NO: 70.

Alanine-scanning mutagenesis of canine IL-31 defined a region within the protein that is necessary for binding to the 11E12 and 34D03 antibodies. It was hypothesized, due to sequence conservation in this region (FIG. 20), that these mAbs would cross-react with feline IL-31.

Figure 21:
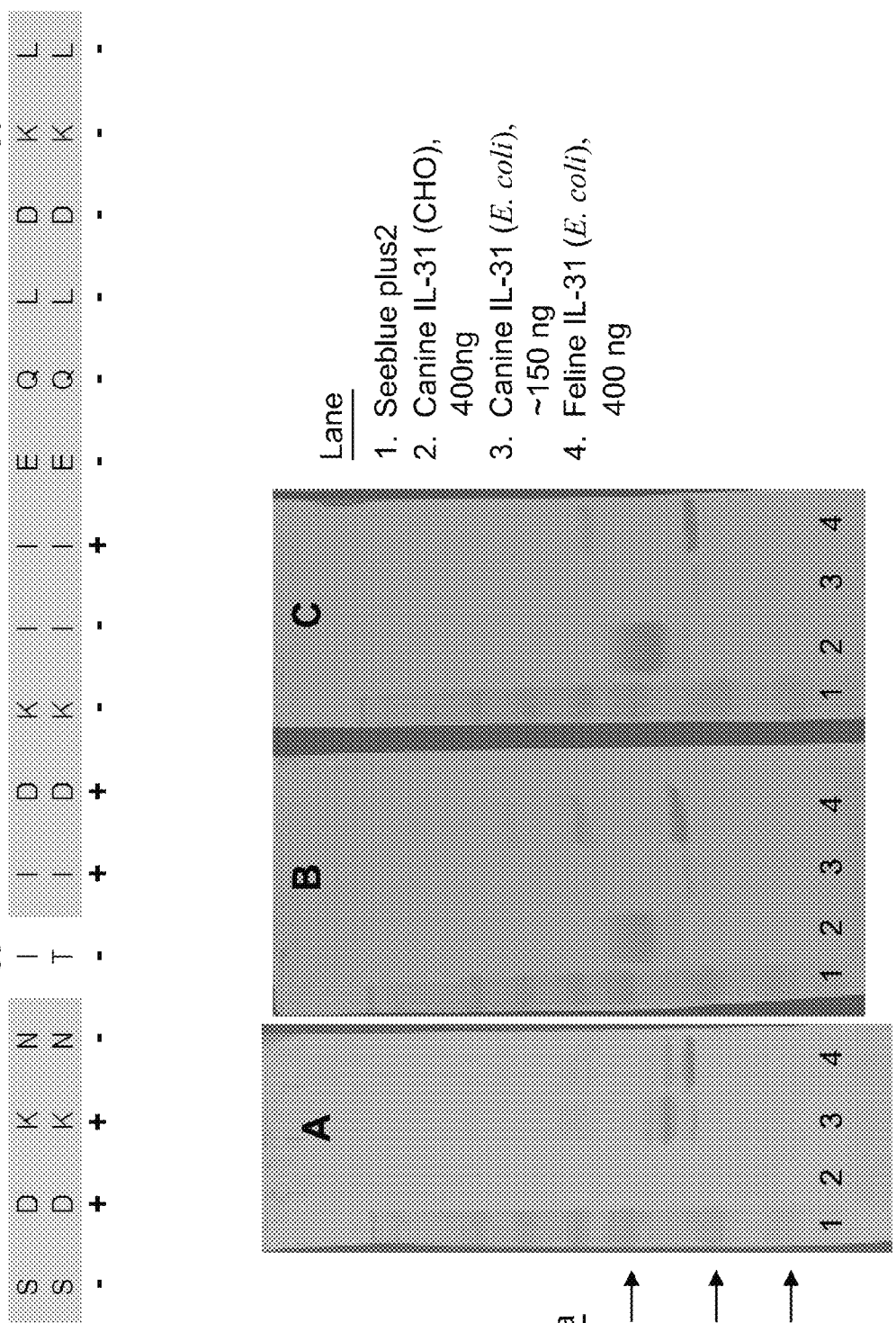
FIG. 21 is of Western blots with IL-31 proteins. Individual nitrocellulose blots were probed with A) anti-His B) 11E12 and C) 34D03 antibodies. Note—Canine IL-31 (CHO) does not contain a 6-His tag.

FIG. 21 shows that mAbs 11E12 and 34D03 are capable of binding to canine IL-31 (*E. coli*) and are also capable of cross-reacting with the feline IL-31 protein. Based on these data, speciation of the 34D03 antibody to feline (felinization) was pursued.

Example 11

Felinization on Antibody 34D03

Figure 22:
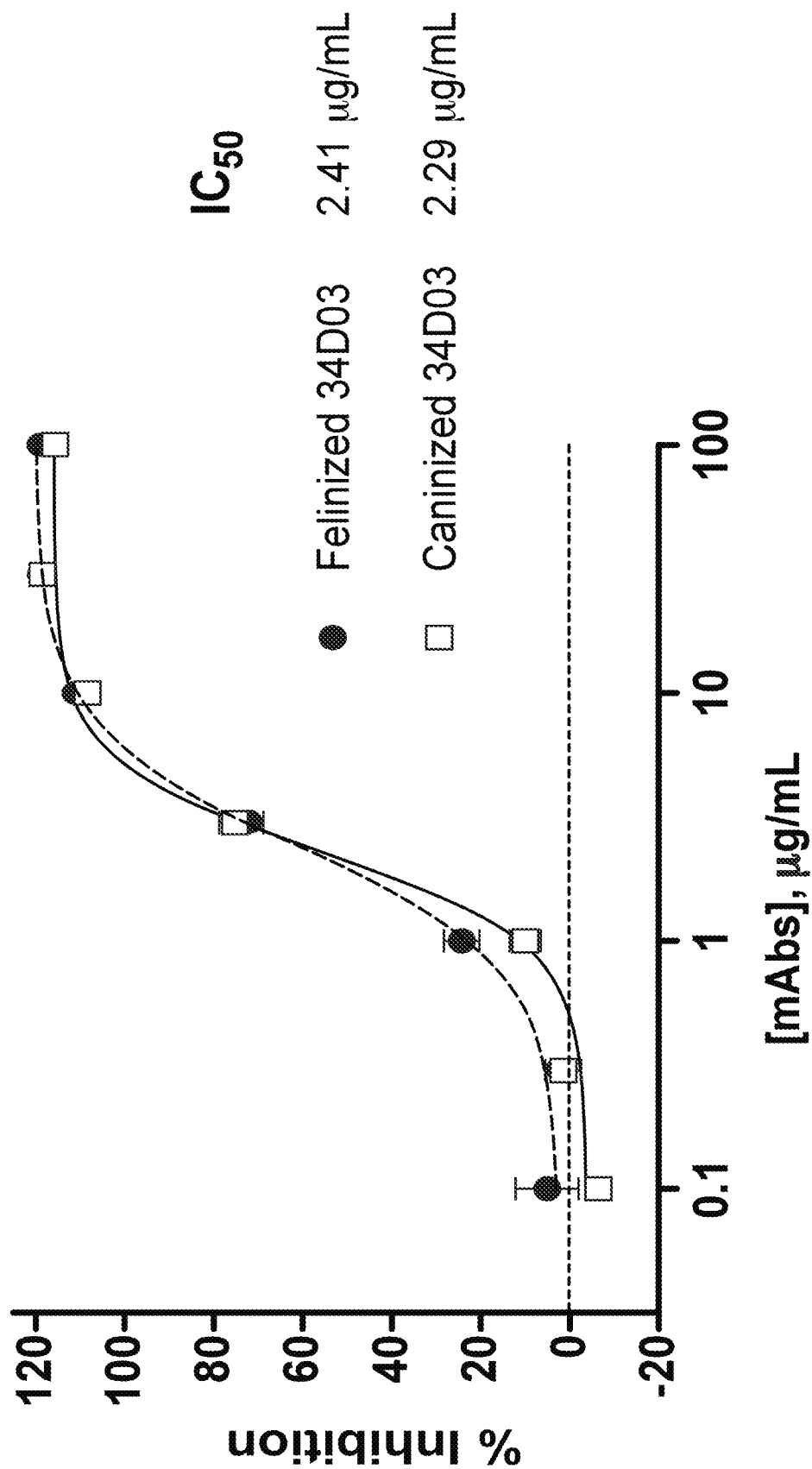
FIG. 22 is a graph showing the inhibition of canine IL-31 induced pSTAT signaling in canine DH82 monocytes comparing felinized and caninized antibody 34D03.

Similar to the caninization strategy described, appropriate germline antibody sequences were identified from all available feline sequences for CDR grafting from mAb 34D03. Variable light chain (SEQ ID NO: 71 FEL-34D03-VL-021-1, the corresponding nucleotide sequence for which is SEQ ID NO: 72) and variable heavy chain (SEQ ID NO: 73 FEL-34D03-VH-035-1, the corresponding nucleotide sequence for which is SEQ ID NO: 74) were selected based on the highest homology to their respective canine frameworks in caninized 34D03. Recombinant felinized 34D03 was produced using the selected variable regions joined to their respective constant heavy IgG1 (SEQ ID NO: 75 HC-A Feline, the corresponding nucleotide sequence for which is SEQ ID NO: 76 GenBank accession No. AB016710.1) and kappa constant light (SEQ ID NO: 77 LC-Kappa Feline, the corresponding nucleotide sequence for which is SEQ ID NO: 78 GenBank accession No. AF198257.1) chain sequence. Antibody was produced from HEK cells and purified as previously described. FIG. 22 shows the ability of feline 34D03 to neutralize pSTAT signaling with a comparable IC50 to the canine version.

Felinized 34D03 was assessed for its ability to bind both feline and canine IL-31. FIG. 23 shows Western blots with felinized 34D03 using purified protein from both mammalian and *E. coli* sources. Conclusive binding was observed to both canine and feline proteins indicating full cross-reactivity of the felinized form of 34D03 and verification of binding to the feline protein. Taken together, these results suggest a conserved epitope on feline IL-31 may be a suitable target for inhibition of this cytokine in cats.

Example 12

Detection of IL-31 Cytokine in Dogs with Naturally Occurring Atopic Dermatitis

In the present example, the level of IL-31 protein in serum collected from populations of dogs, including those with atopic dermatitis, was evaluated using a quantitative immunoassay technique.

Serum was collected from the following populations of dogs and frozen prior to IL-31 serum measurements.
1) Twenty four purpose bred beagles (Marshall BioResources, North Rose, N.Y.) prior to and after sensitization to house dust mite allergen (*Dermatophagoides farina*, Greer Labs). All animals were approximately 9 months in age. The two sexes were represented approximately equally.
2) Thirty flea allergic dogs (Youngs Veterinary Research Services, Turlock, Calif.) prior to flea infestation or approximately one week after infestation with adult cat fleas (*Ctenocephalides felis*). The majority of the dogs in this colony were of mixed breed. The average age was approximately 10.5 years. The two sexes were represented approximately equally.
3) Eighty seven client-owned dogs with sub-clinical periodontal disease but otherwise determined to be in good health. Samples were collected across 18 US veterinary clinics. Animals were representative of the US canine population in terms of gender and breed and were between the age of two and five years.
4) Two hundred and twenty four client-owned animals diagnosed with chronic, non-seasonal atopic dermatitis of at least 1-year duration (based on modified Willemse's criteria, and Prelaud (Willemse T. *J small Anim Pract* 1986; 27:771-778 and Prelaud et al. *Revue de Medecine Veterinaire* 1998; 149: 1057-1064) with a minimum of "moderate itching" as assessed by the Owner, and a minimum skin lesion score of 25 on the CADESI-02) as assessed by a veterinarian. Samples were collected from 14 US veterinary practices with expertise in veterinary dermatology. Approximately 75% of the dogs were purebred and ~25% of the total population were retrievers (Labrador (17.3%) and Golden (8.2%)). Dogs tended to be middle-aged (~6 years old). The two sexes were represented approximately equally.

A sandwich immunoassay was used to quantitate cIL-31 levels in canine serum. Serum samples were diluted 1:2 in Rexxip buffer (Gyrolab, Warren, N.J.) and run on Bioaffy 1000 nL CDs (Gyrolab) using the Gyrolab xP workstation. cIL-31 was captured with a biotin-labeled anti-IL-31 monoclonal antibody according to the present invention and detected with an Alexaflour 647 labeled anti-IL-31 monoclonal antibody according to the present invention. Sample concentrations of cIL-31 were extrapolated from an 8-point standard curve with a dynamic range of 0.013-250 ng/mL using a 5-parmameter fit model with Gyrolab Evaluator software.

Levels of cIL-31 were detectable in serum samples of 57% of dogs with naturally occurring atopic dermatitis (≥13 pg/mL) but were not detectable (<13 pg/mL) in the serum from purpose-bred beagles +/−sensitized to HDM, mixed breed dogs +/−flea infestation, or client-owned dogs with periodontal disease but otherwise considered in good health, regardless of breed. In the dogs with naturally occurring atopic dermatitis, 53% of the samples analyzed showed serum IL-31 levels between 13-1000 pg/mL, and 4% showed levels above 1000 pg/mL (Table 5).

TABLE 5

Serum IL-31 Levels in Various Canine Populations

| Canine Populations | Number of Animals Evaluated | Number of Animals with Detectable IL-31 in Serum[a] | Percent of Animals with Detectable IL-31 in Serum |
|---|---|---|---|
| Purpose-bred beagles | 24 | 0 | 0% |
| Purpose-bred beagles sensitized to HDM | 24 | 0 | 0% |
| Mixed breed dogs - no fleas | 30 | 0 | 0% |
| Mixed breed dogs - infested with fleas | 30 | 0 | 0% |
| Healthy client owned animals - multiple breeds | 87 | 0 | 0% |
| Naturally occurring atopic dermatitis in client owned animals - multiple breeds | 224 | 128 | 57% |

[a]Less than 13 pg/mL is below limits of quantitiation.

The results of the present example demonstrate that IL-31 protein is elevated in a significant number of dogs with canine atopic dermatitis. Without wishing to be bound by any one theory, it is believed that the IL-31 pathway plays a role in the pathobiology of pruritic allergic skin conditions such as, but not limited to, canine atopic dermatitis and represents a novel pathway for therapeutic intervention with an IL-31 antagonist, such as including, but not limited to, olacitnib and/or an anti-IL-31 antibody that specifically binds to canine IL-31.

What is claimed is:

1. An isolated antibody, or antigen-binding portion thereof comprising at least one of the following combinations of complementary determining region (CDR) sequences:
   1) 11E12: variable heavy (VH)-CDR1 of SEQ ID NO: 1, VH-CDR2 of SEQ ID NO: 4, VH-CDR3 of SEQ ID NO: 7, variable light (VL)-CDR1 of SEQ ID NO: 10, VL-CDR2 of SEQ ID NO: 13, and VL-CDR3 of SEQ ID NO: 16;
   2) 19D07: VH-CDR1 of SEQ ID NO: 2, VH-CDR2 of SEQ ID NO: 5, VH-CDR3 of SEQ ID NO: 8, VL-CDR1 of SEQ ID NO: 11, VL-CDR2 of SEQ ID NO: 14, and VL-CDR3 of SEQ ID NO 17; or
   3) 34D03: VH-CDR1 of SEQ ID NO: 3, VH-CDR2 of SEQ ID NO: 6, VH-CDR3 of SEQ ID NO: 9, VL-CDR1 of SEQ ID NO: 12, VL-CDR2 of SEQ ID NO: 15, and VL-CDR3 of SEQ ID NO: 18.

2. The antibody of claim 1, wherein said antibody reduces, inhibits, or neutralizes an IL-31-mediated pruritic or allergic condition.

3. The antibody of claim 1, wherein said antibody is a monoclonal antibody.

4. The antibody of claim 3, wherein the antibody is chimeric.

5. The antibody of claim 3, wherein the antibody is caninized or felinized.

6. The antibody of claim 1, wherein said antibody reduces, inhibits, or neutralizes IL-31 activity in a dog or cat.

7. The antibody of claim 1 comprising at least one of the group consisting of:
   a) a variable light chain comprising

```
                                                  (SEQ ID NO: 19; MU-11E12-VL)
DIVLTQSPASLAVSLGQRATISCRASESVDNYGISFMHWYQQKPGQPPKLLIYRASNLESGIPAR

FSGSGSRTDFTLTINPVETDDVATYYCQQSNKDPLTFGAGTKLELK, (SEQ ID NO: 20; CAN-11E12-VL-cUn-FW2)
DIVMTQTPLSLSVSPGEPASISCRASESVDNYGISFMHWYQQKPGQPPKLLIYRASNLESGVPD

RFSGSGSGTDFTLRISRVEADDAGVYYCQQSNKOPLTFGAGTKLEIK, (SEQ ID NO; 21; CAN-11E12-VL-cUn-13)
DIVMTQTPLSLSVSPGEPASISCRASESVDNYGISFMHWFQQKPGQSPQLLIYRASNLESGVPD

RFSGSGSGTDFTLRISRVEADDAGVYYCQQSNKDPLTFGAGTKLEIK, (SEQ ID NO: 22; MU-19D07-VL)
DIVMSQSPSSLSVSAGDKVTMSCKSSQSLLNSGNQKNYLAWYQQKPWQPPKLLIYGASTRES

GVPDRFTGSGSGTDFTLTISSVQAEDLAVYYCQNDYSYPYTFGGGTKLEIK, (SEQ ID NO: 23; CAN-19D07-VL-998-1)
EIVMTQSPASLSLSQEEKVTITCKSSQSLLNSGNQKNYLAWYQQKPGQAPKLLIYGASTRESGV

PSRFSGSGSGTDFSFTISSLEPEDVAVYYCQNDYSYPYTFGQGTKLEIK, (SEQ ID NO: 24; MU-34D03-VL)
DILLTQSPASLAVSLGQRAIISCKASQSVSFAGTGLMHWYQQKPGQQPKLLIYRASNLEAGVPT

RFSGSGSRTDFTLNIHPVEEEDAATYFCQQSREYPWTFGGGTKLEIK,
or
```

-continued (SEQ ID NO: 25; CAN-34D03-VL-998-1)
EIVMTQSPASLSLSQEEKVTITCKASQSVSFAGTGLMHWYQQKPGQAPKLLIYRASNLEAGVPS

RFSGSGSGTDFSFTISSLEPEDVAVYYCQQSREYPWTFGQGTKLEIK;

and b) a variable heavy chain comprising (SEQ ID NO: 26; MU-11E12-VH)
QVQLQQSGAELVKPGASVKLSCKASGYTFKYYDINWVRQRPEQGLEWIG

WIFPGDGGTKYNETFKGKATLTTDKSSSTAYMQLSRLTSEDSAVYFCAR

GGTSVIRDAMDYWGQGTSVTVSS, (SEQ ID NO: 27; CAN-11E12-VH-415-1)
EVQLVQSGAEVKKPGASVKVSCKTSGYTFKYYDINWVRQAPGAGLDWM

GWIFPGDGGTKYNETFKGRVTLTADTSTSTAYMELSSLRAGDIAVYYC

ARGGTSVIRDAMDYWGQGTLVTVSS, (SEQ ID NO: 28; MU-19D07-VH)
EVKLVESGGGLVKPGGSLKLSCAASGFAFSSYDMSWVRQIPEKRLEWVA

TITSGGGYTYSADSVKGRFTISRDNARNTLYLQMSSLRSEDTAVYYCAR

QNWVVGLAYWGQGTLVTVSA, (SEQ ID NO: 29; CAN-19D07-VH-400-1)
EVQLVESGGDLVKPGGSLRLSCVASGFTFSSYDMSWVRQAPGKGLQWVA

TITSGGGYTYSADSVKGRFTISRDNARNTLYLQMNSLRSEDTAVYYCAR

QNWVVGLAYWGQGTLVTVSS, (SEQ ID NO: 30; MU-34D03-VH)
EVQLVESGGDLVKPGGSLKLSCAASGFSFSNYGMSWVRQTPDKRLEWVA

TISYGGSYTYYPDNIKGRFTISRDNAKNTLYLQMSSLKSEDTAMYYCVR

GYGYDTMDYWGQGTSVTVSS,
or (SEQ ID NO: 31; CAN-34D03-VH-568-1)
EVQLVESGGDLVKPGGSLRLSCVASGFTFSNYGMSWVRQAPGKGLQWVA

TISYGGSYTYYPDNIKGRFTISRDNAKNTLYLQMNSLRAEDTAMYYCVR

GYGYDTMDYWGQGTLVTVSS.

8. A veterinary composition comprising a therapeutically effective amount of the antibody of claim 1.

9. A monoclonal antibody that specifically binds to a region between about amino acid residues 95 and 125 of the canine IL-31 amino acid sequence of SEQ ID NO: 32 or a corresponding region in feline IL-31.

10. The antibody of claim 9, wherein the antibody specifically binds to a region between about amino acid residues 102 and 122 of the canine IL-31 sequence of SEQ ID NO: 32 or a corresponding region in feline IL-31.

11. The antibody of claim 9, wherein the antibody specifically binds to a region between about amino acid residues 95 and 125 of the canine IL-31 amino acid sequence of SEQ ID NO: 32.

12. The antibody of claim 9, wherein the antibody is chimeric.

13. The antibody of claim 9, wherein the antibody is caninized or felinized.

14. The antibody of claim 9, wherein said antibody reduces, inhibits, or neutralizes an IL-31-mediated pruritic or allergic condition.

15. A method of treating an IL-31-mediated pruritic or allergic condition in a subject, comprising administering a therapeutically effective amount of the antibody of claim 14 to the subject.

16. The method of claim 15, wherein the IL-31-mediated pruritic or allergic condition is a pruritic condition selected from the group consisting of atopic dermatitis, eczema, psoriasis, scleroderma, and pruritis.

17. The method of claim 15, wherein the IL-31-mediated pruritic or allergic condition is an allergic condition is selected from the group consisting of allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity.

18. The method of claim 15, wherein the antibody is administered biweekly or monthly.

19. The method of claim 15, wherein the antibody is administered subcutaneously at 1.0 mg/kg of body weight.

20. The antibody of claim 9, wherein said antibody reduces, inhibits, or neutralizes IL-31 activity in a dog or cat.

21. A method of inhibiting IL-31 activity in a dog or cat comprising administering an antibody according to claim 20 to the dog or cat.

22. The method of claim 21, wherein the antibody is administered biweekly or monthly.

23. The method of claim 21, wherein the antibody is administered subcutaneously at 1.0 mg/kg of body weight.

24. A veterinary composition comprising a therapeutically effective amount of the antibody of claim 9.

25. A method of detecting IL-31 comprising:
 (a) incubating a sample comprising IL-31 in the presence of an antibody according to claim 9; and
 (b) detecting the antibody which is bound to IL-31 in the sample.

26. The method of claim 25, wherein the antibody comprises a label.

27. The method of claim 25, further comprising detecting the antibody with a second antibody comprising a label.

28. The method of claim 25, further comprising quantitating the IL-31 in the sample.

* * * * *